(12) United States Patent
Teutsch et al.

(10) Patent No.: US 9,662,453 B2
(45) Date of Patent: *May 30, 2017

(54) DOSING UNIT FOR AN AMBULATORY INFUSION DEVICE

(71) Applicant: Roche Diagnostics International AG, Rotkreuz (CH)

(72) Inventors: David Teutsch, Schuepfen (CH); Martin Wyss, Rotkreuz (CH); Ulrich Haueter, Grosshoechstetten (CH); Simon Scheurer, Bern (CH)

(73) Assignee: Roche Diagnostics International AG, Rotkreuz (CH)

( * ) Notice: Subject to any disclaimer, the term of this patent is extended or adjusted under 35 U.S.C. 154(b) by 95 days.

This patent is subject to a terminal disclaimer.

(21) Appl. No.: 14/192,946

(22) Filed: Feb. 28, 2014

(65) Prior Publication Data

US 2015/0065958 A1 Mar. 5, 2015

Related U.S. Application Data

(63) Continuation of application No. PCT/EP2012/065971, filed on Aug. 15, 2012, and a
(Continued)

(51) Int. Cl.
*A61M 5/315* (2006.01)
*A61M 5/142* (2006.01)
(Continued)

(52) U.S. Cl.
CPC ...... *A61M 5/31528* (2013.01); *A61M 5/1454* (2013.01); *A61M 5/14216* (2013.01);
(Continued)

(58) Field of Classification Search
CPC .......... A61M 5/31528; A61M 5/31511; A61M 5/31563; A61M 5/1454; A61M 5/14244; A61M 5/14216; A61M 2205/103; A61M 5/1456; A61M 5/14566; F04B 53/14; F04B 13/00; F04B 9/02
See application file for complete search history.

(56) References Cited

FOREIGN PATENT DOCUMENTS

EP 1970677 A1 9/2008
EP 2163273 A1 * 3/2010 ........ A61M 5/14216

* cited by examiner

*Primary Examiner* — Kevin C Sirmons
*Assistant Examiner* — Amber Stiles
(74) *Attorney, Agent, or Firm* — Woodward, Emhardt, Moriarty, McNett & Henry LLP

(57) ABSTRACT

At least one dosing unit for an infusion pump is disclosed having a piston pump with a pump cylinder, a plunger arranged within said cylinder, and a plunger driving part provided for transmitting rotational torque from a driving unit to the plunger without itself being linearly displaced. The cylinder, the plunger and the plunger coupling element are coaxially arranged along a longitudinal axis and rotatable around said axis in regard to static parts of the dosing unit. The plunger and cylinder each having threads which engage with each other in such a way that a rotational movement of the plunger around the longitudinal axis results in a linear displacement of the plunger along the longitudinal axis. The dosing unit also having first coupling parts associated with the cylinder and second coupling parts associated with the plunger.

26 Claims, 32 Drawing Sheets

Related U.S. Application Data continuation of application No. PCT/EP2011/065243, filed on Sep. 2, 2011.

(51) Int. Cl.
    *F04B 9/02*       (2006.01)
    *F04B 13/00*     (2006.01)
    *F04B 53/14*     (2006.01)
    *A61M 5/145*    (2006.01)

(52) U.S. Cl.
    CPC .... *A61M 5/14244* (2013.01); *A61M 5/31511* (2013.01); *A61M 5/31563* (2013.01); *F04B 9/02* (2013.01); *F04B 13/00* (2013.01); *F04B 53/14* (2013.01); *A61M 5/1456* (2013.01); *A61M 5/14566* (2013.01); *A61M 2205/103* (2013.01)

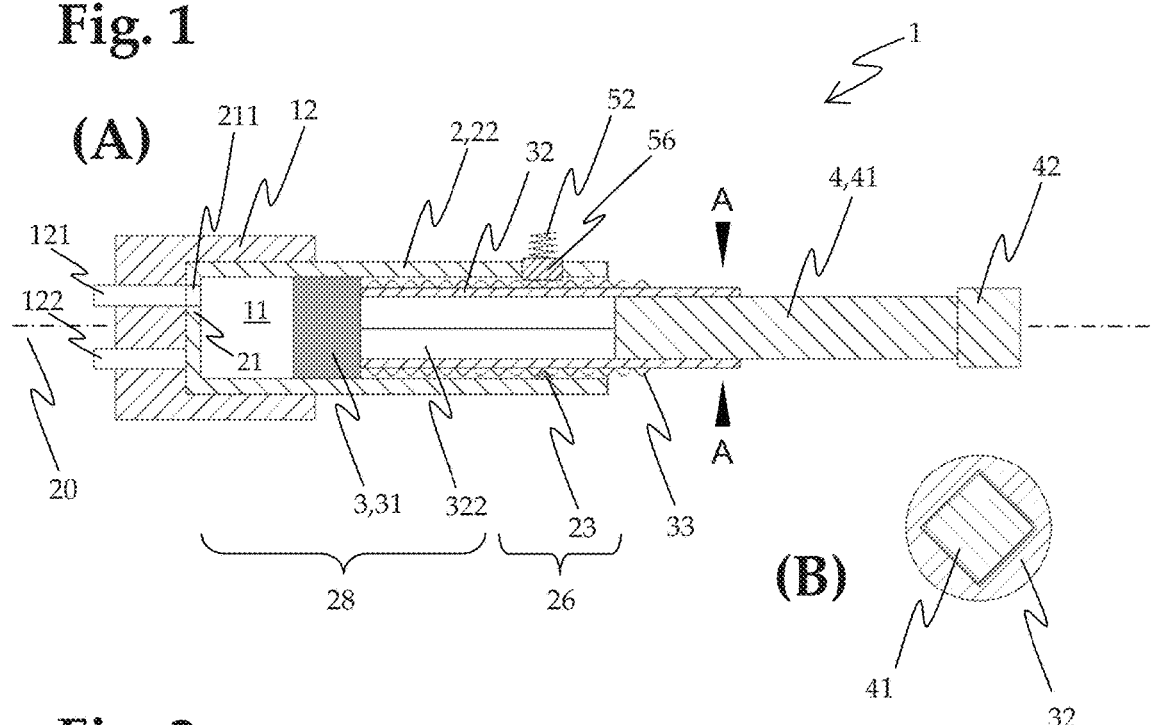
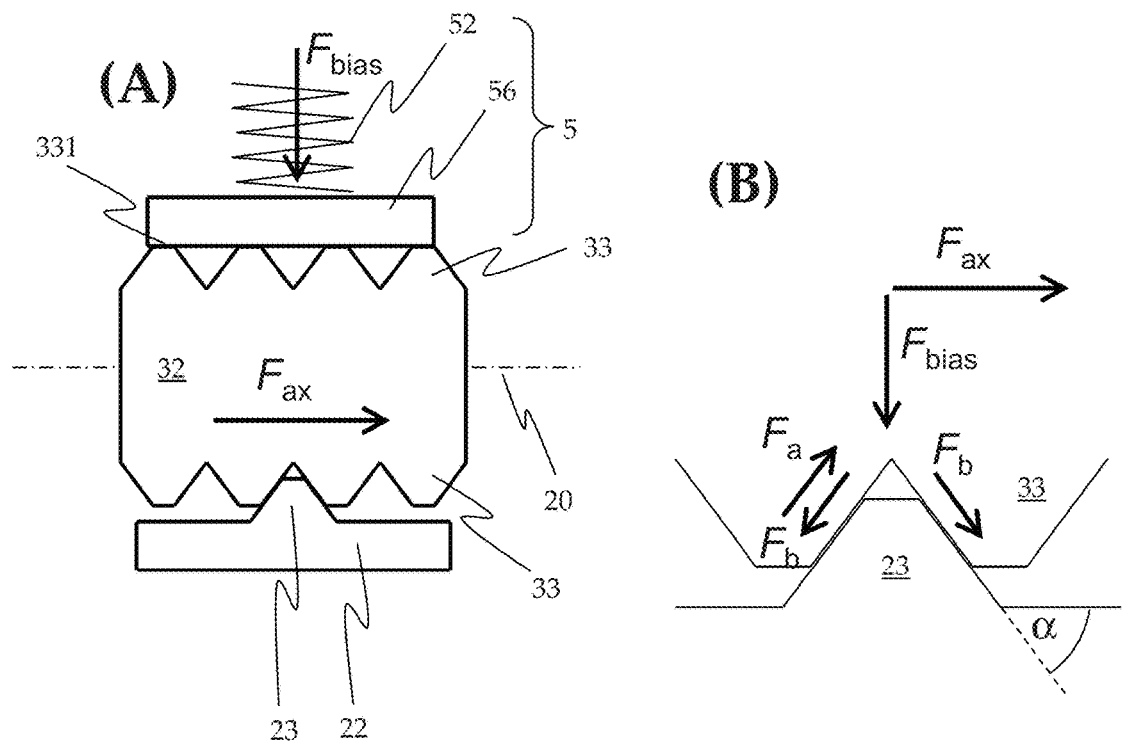

Fig. 3
(A) 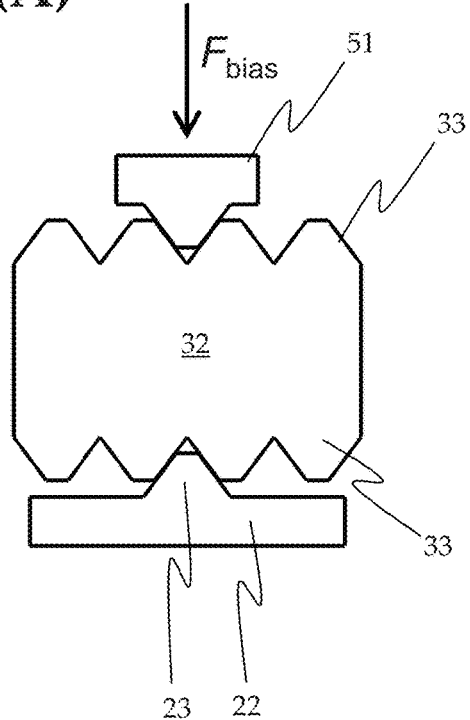
(B) 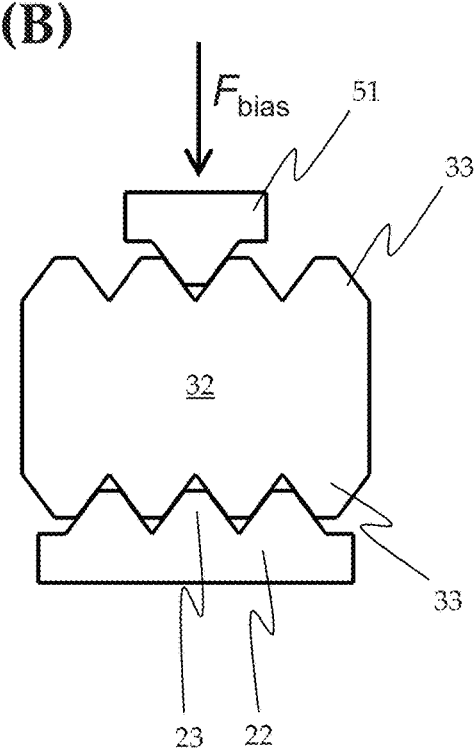
Fig. 6
(A) 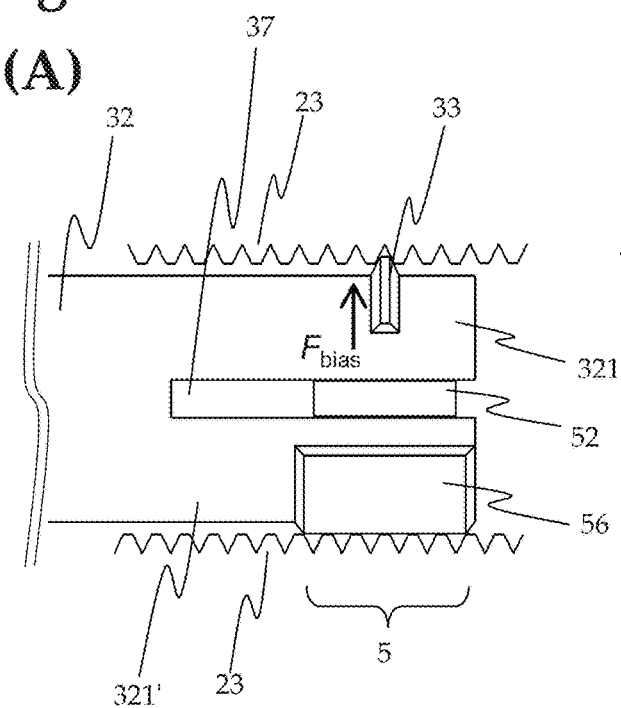
(B) 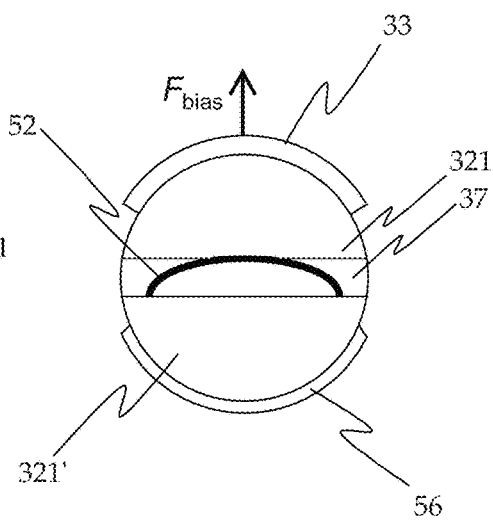

Fig. 5
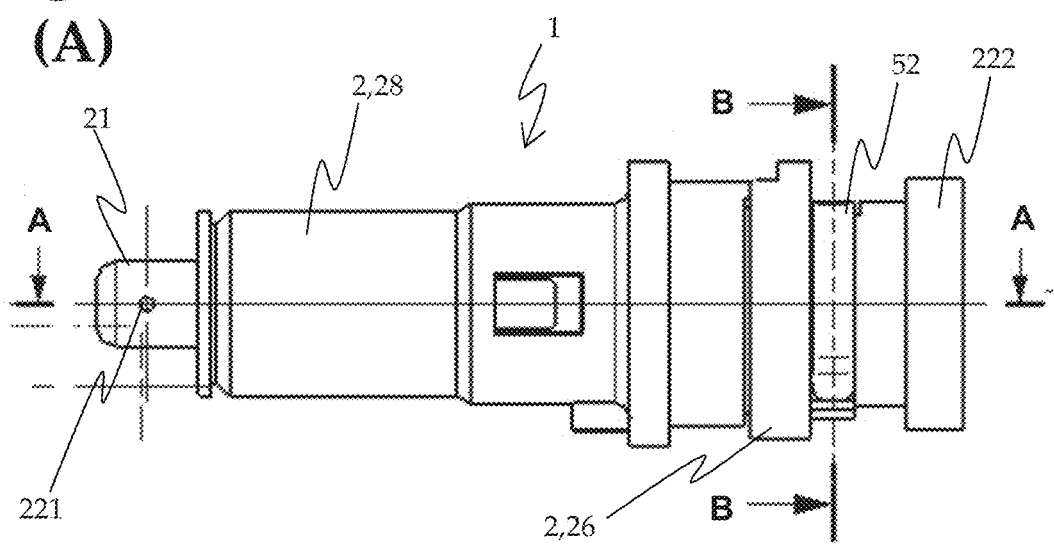
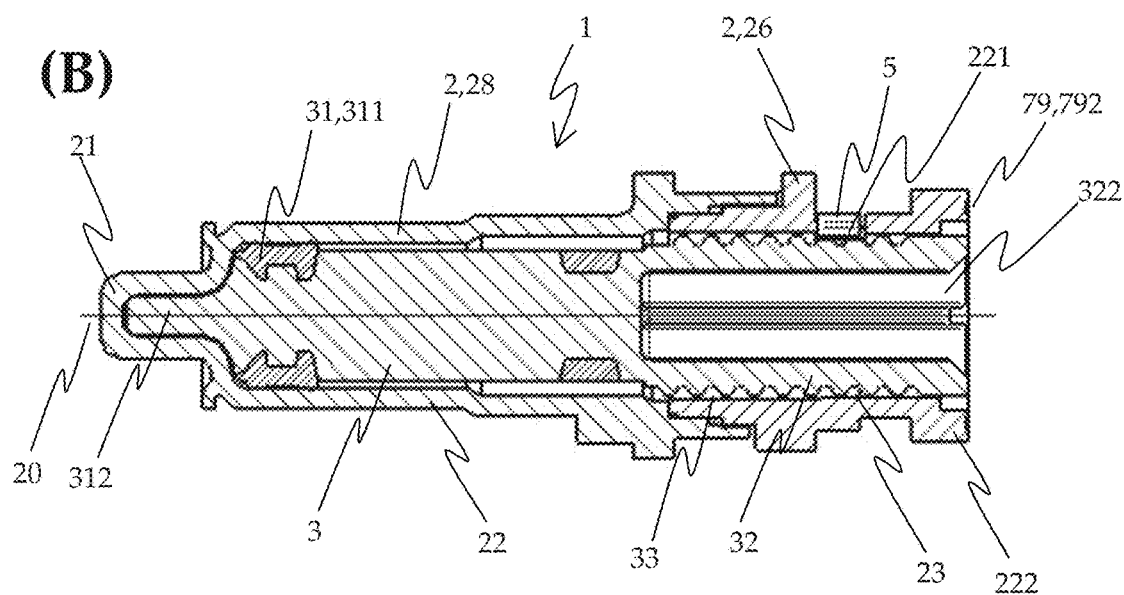
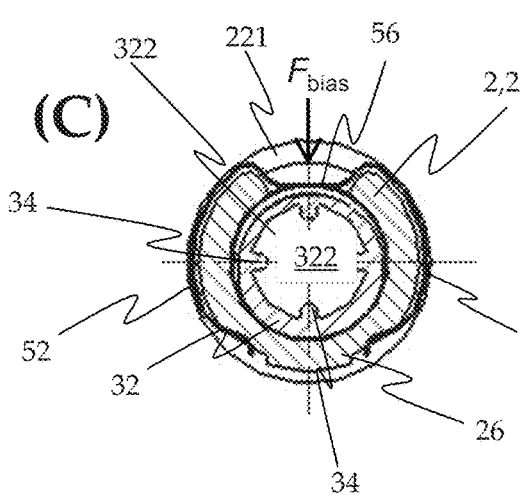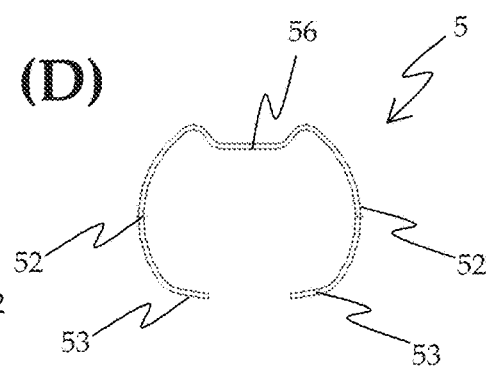

Fig. 8
(A) 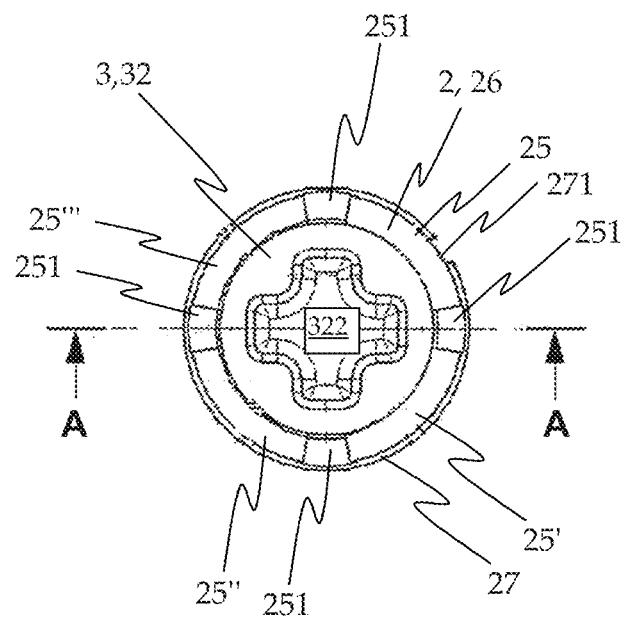
(B) 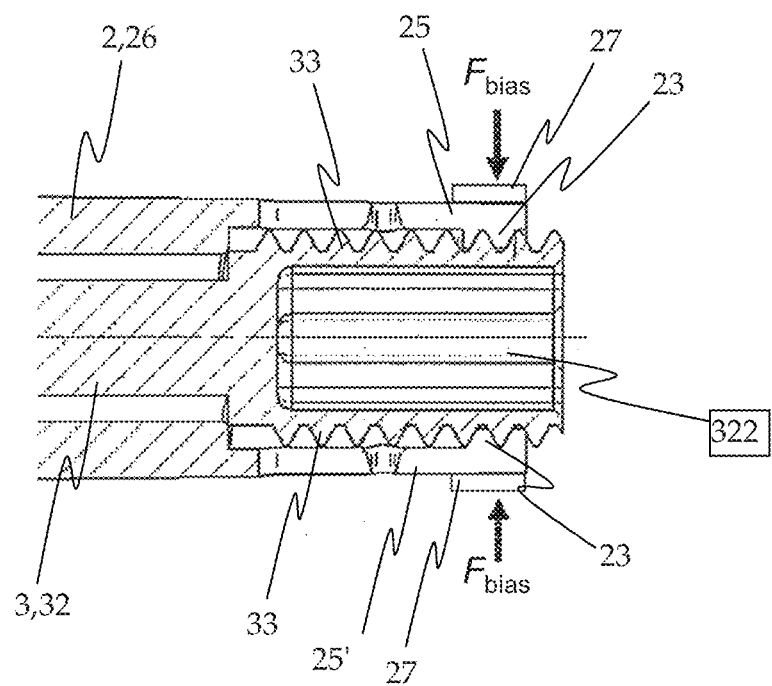

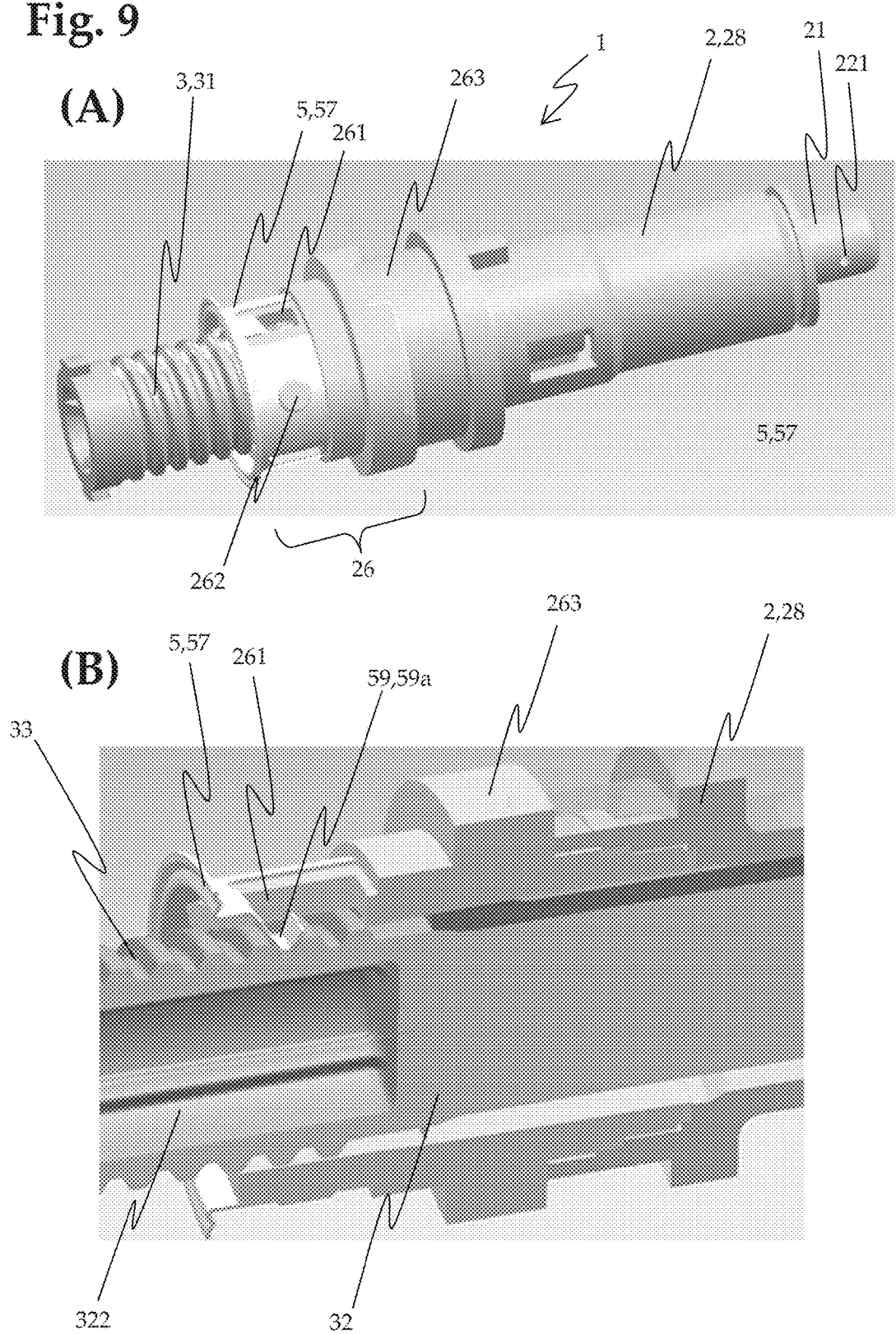

Fig. 11
(A)
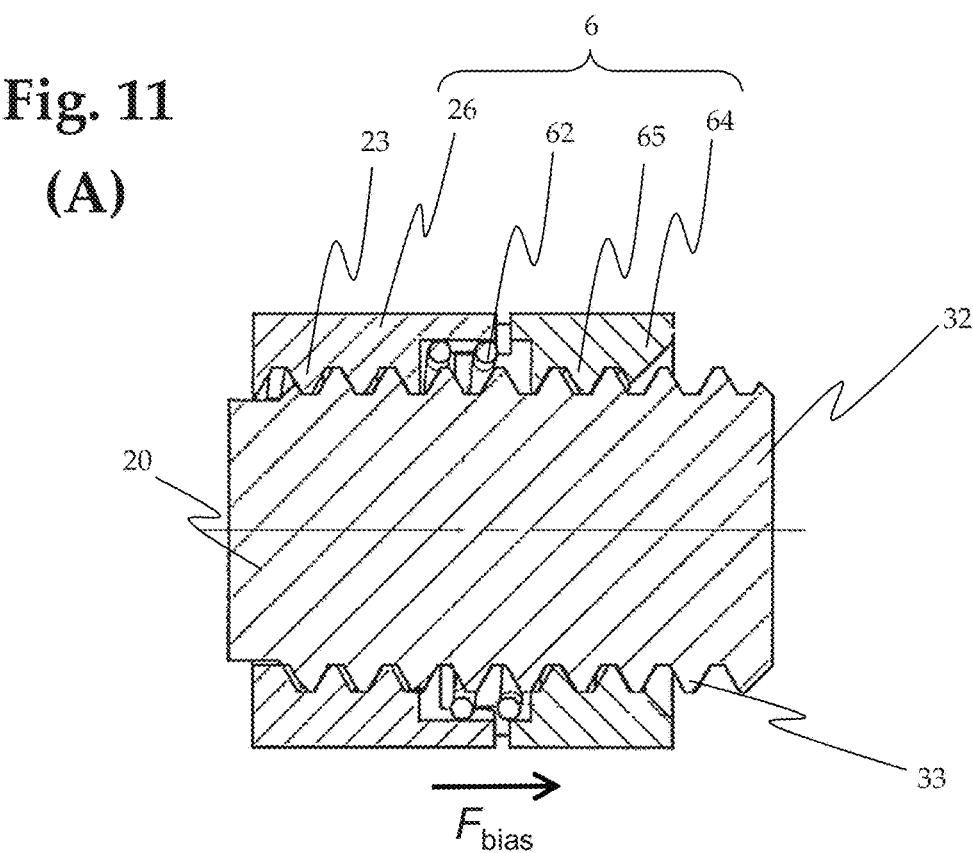
(B)
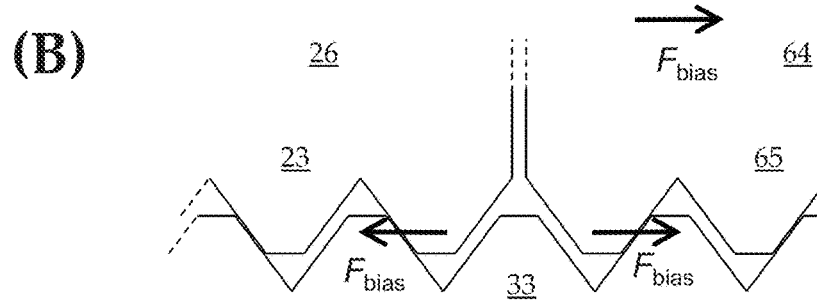
(C)
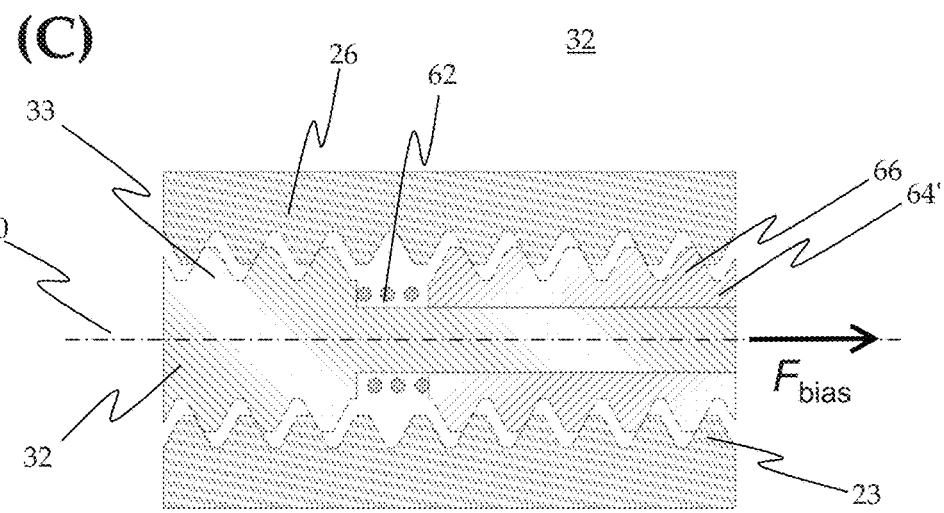

Fig. 12
(D)
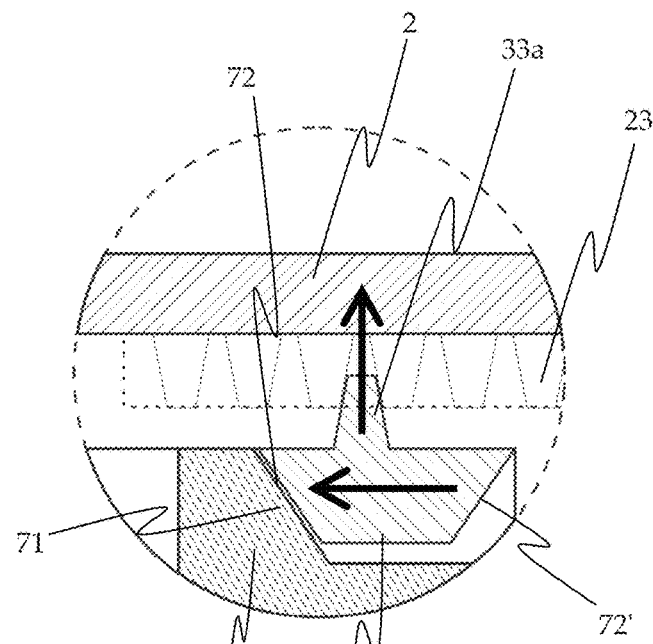
Fig. 13
(A)
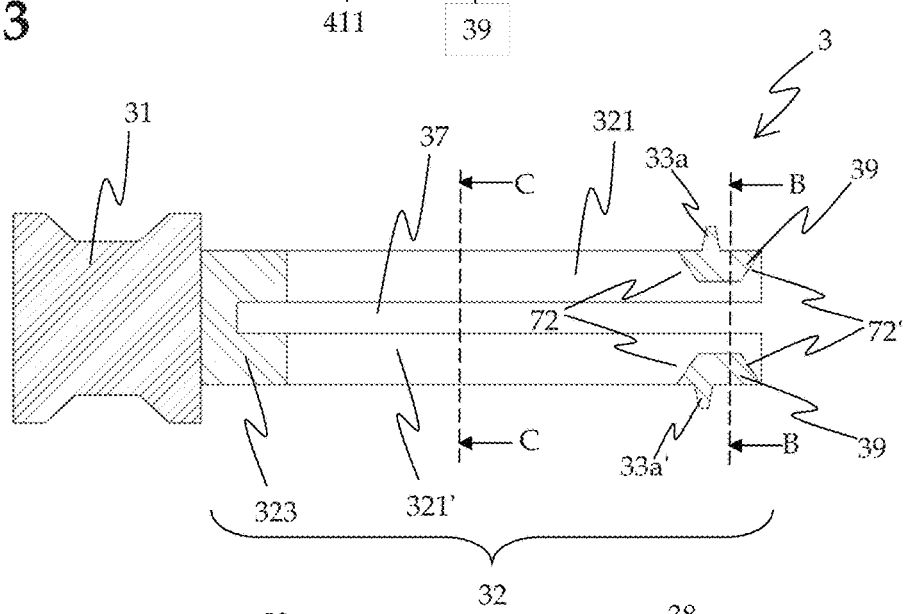
(B) 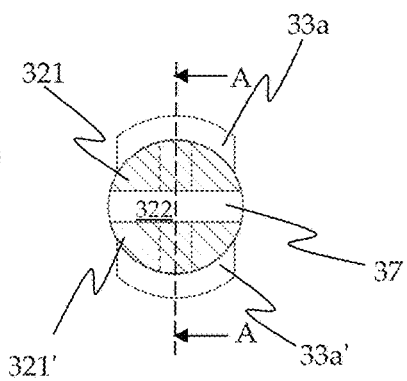
(C) 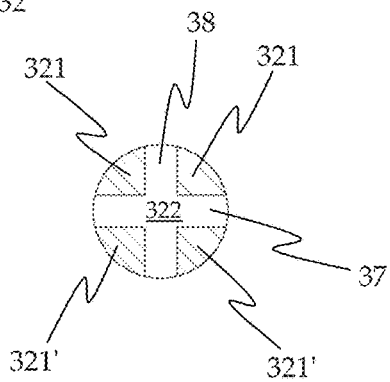

Fig. 14
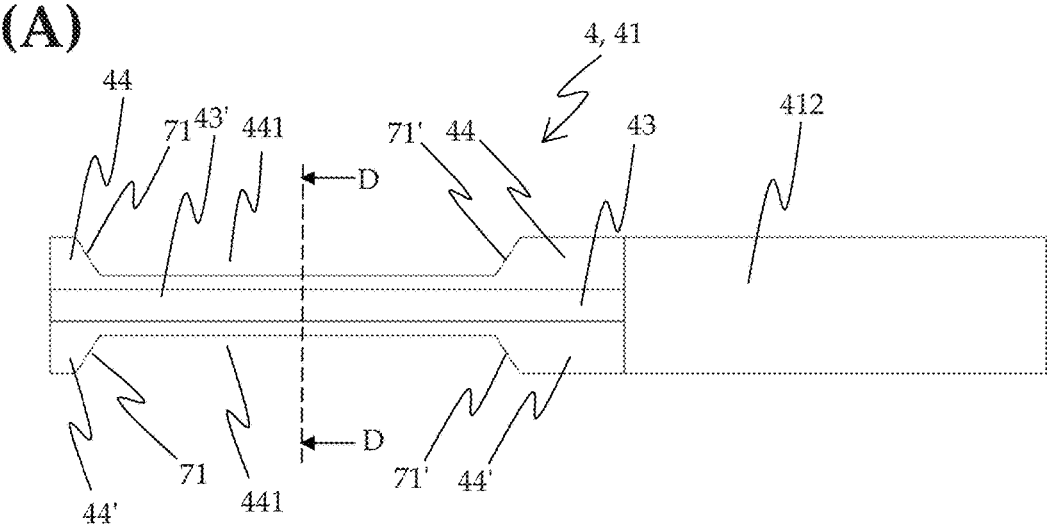
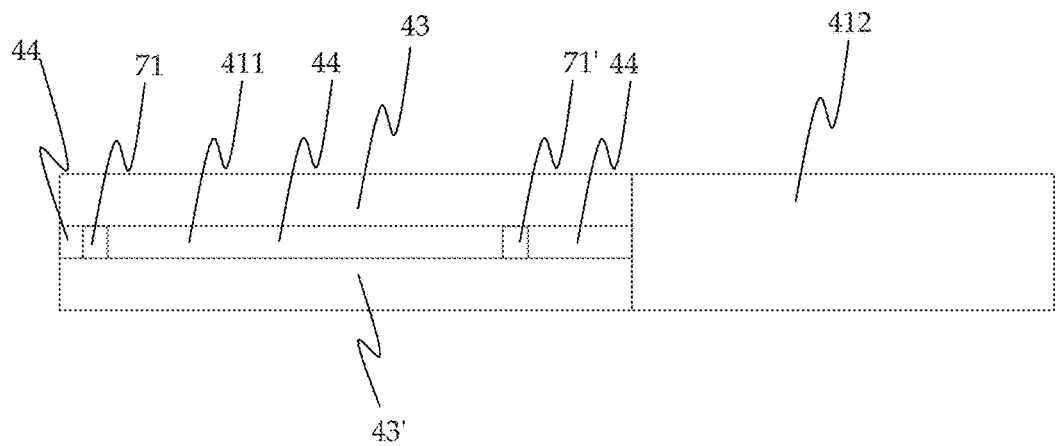
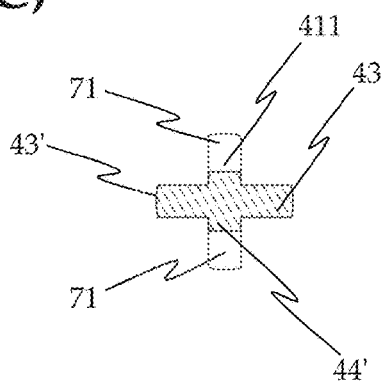

Fig. 16
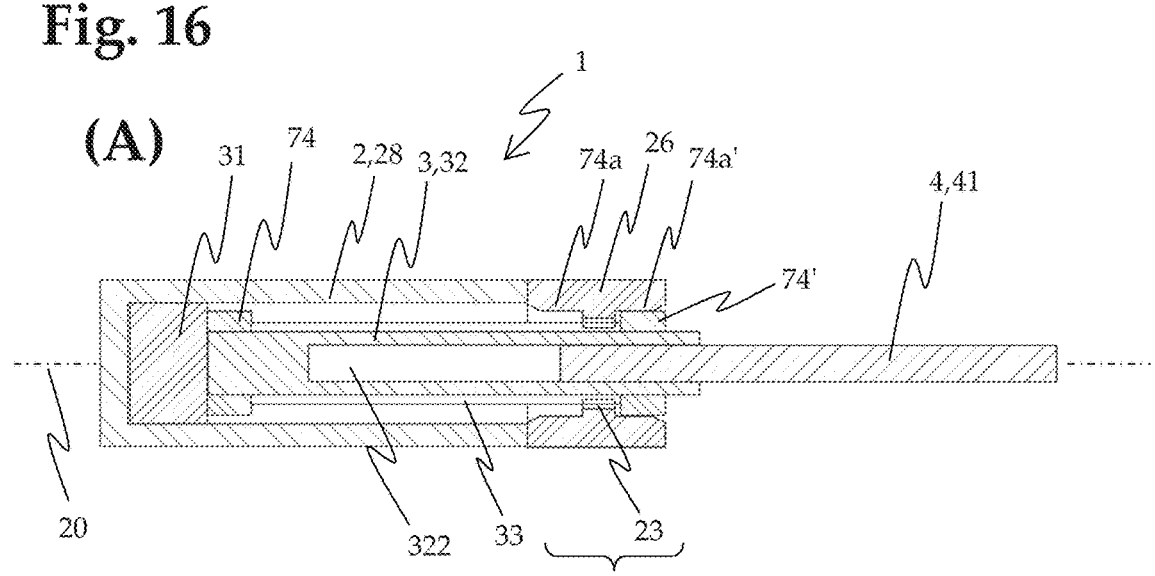
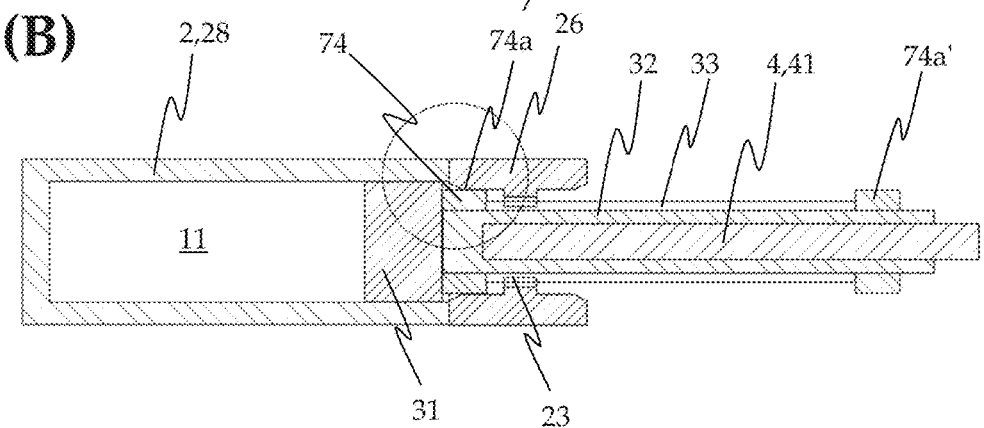
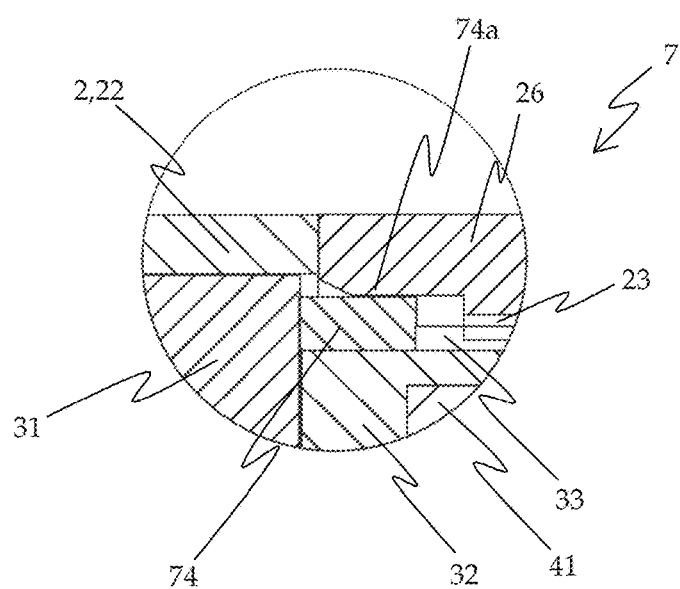

Fig. 18
(A)
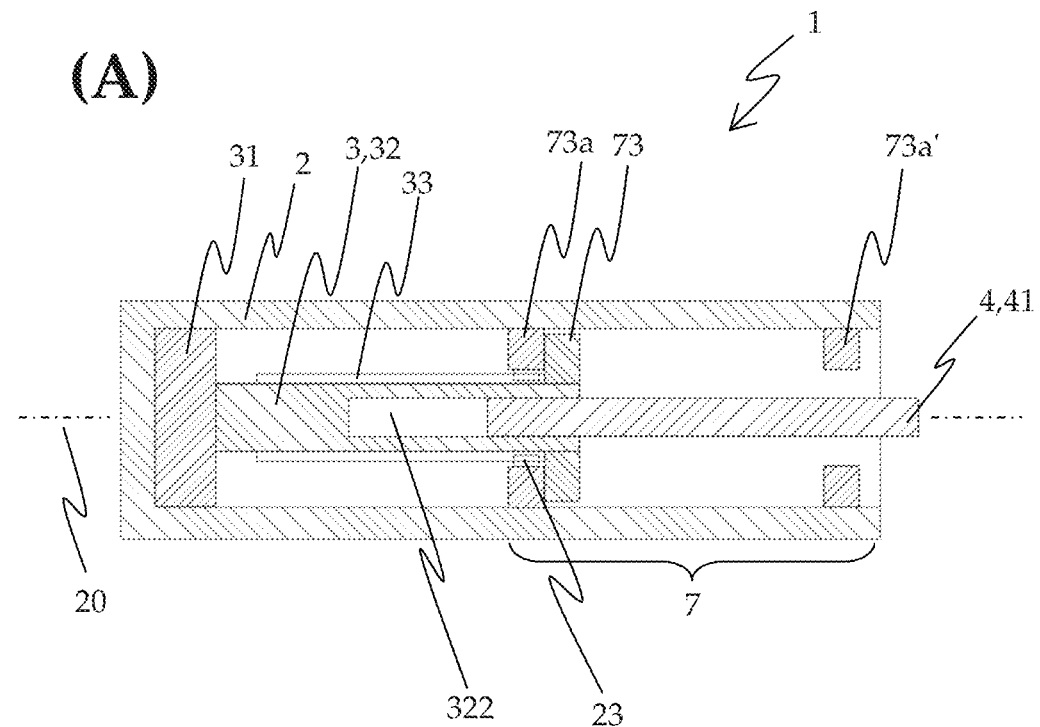
(B)
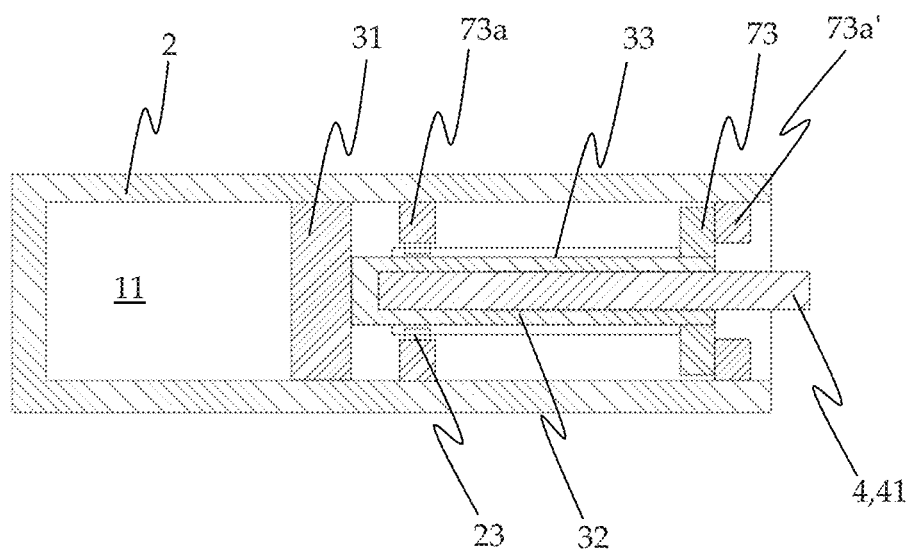

Fig. 20
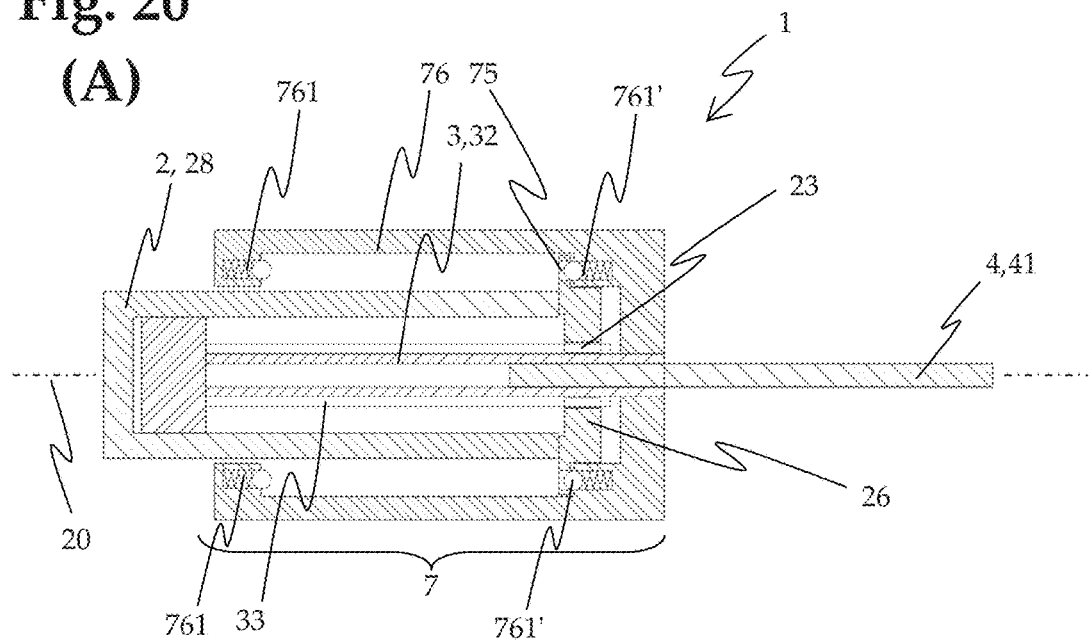
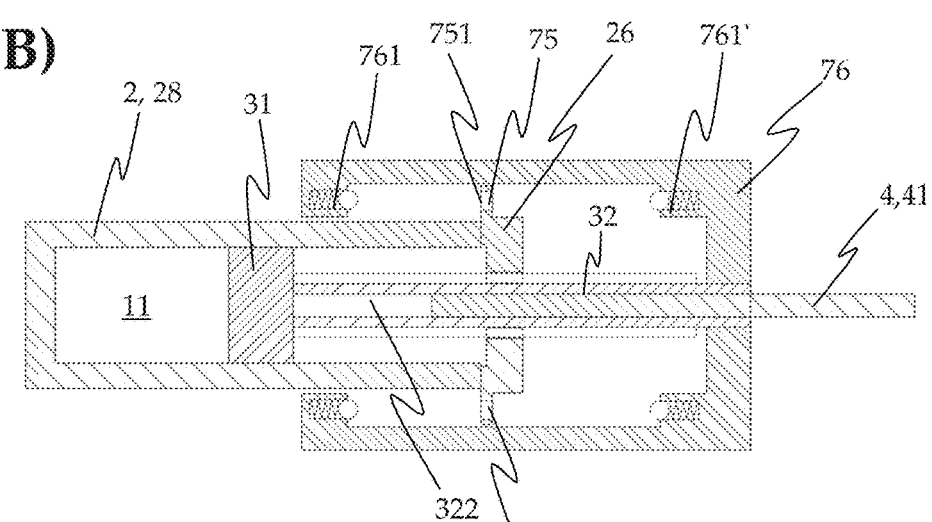
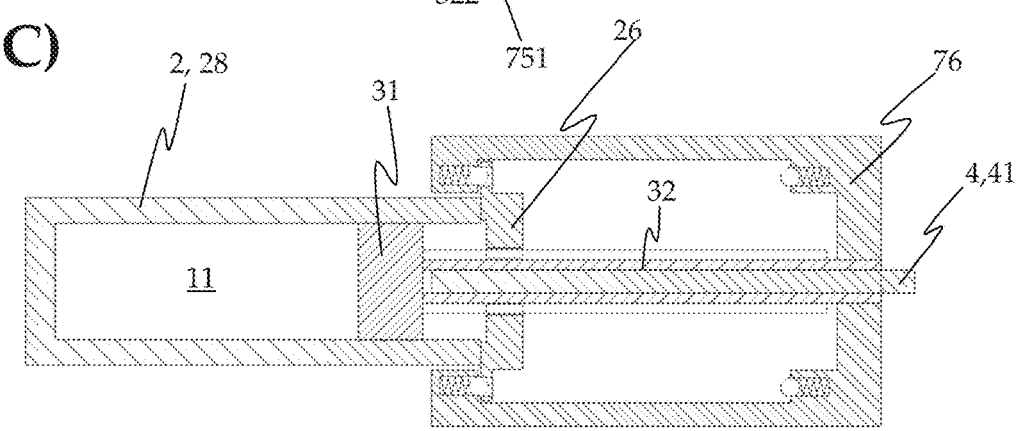

(M)

Fig. 23
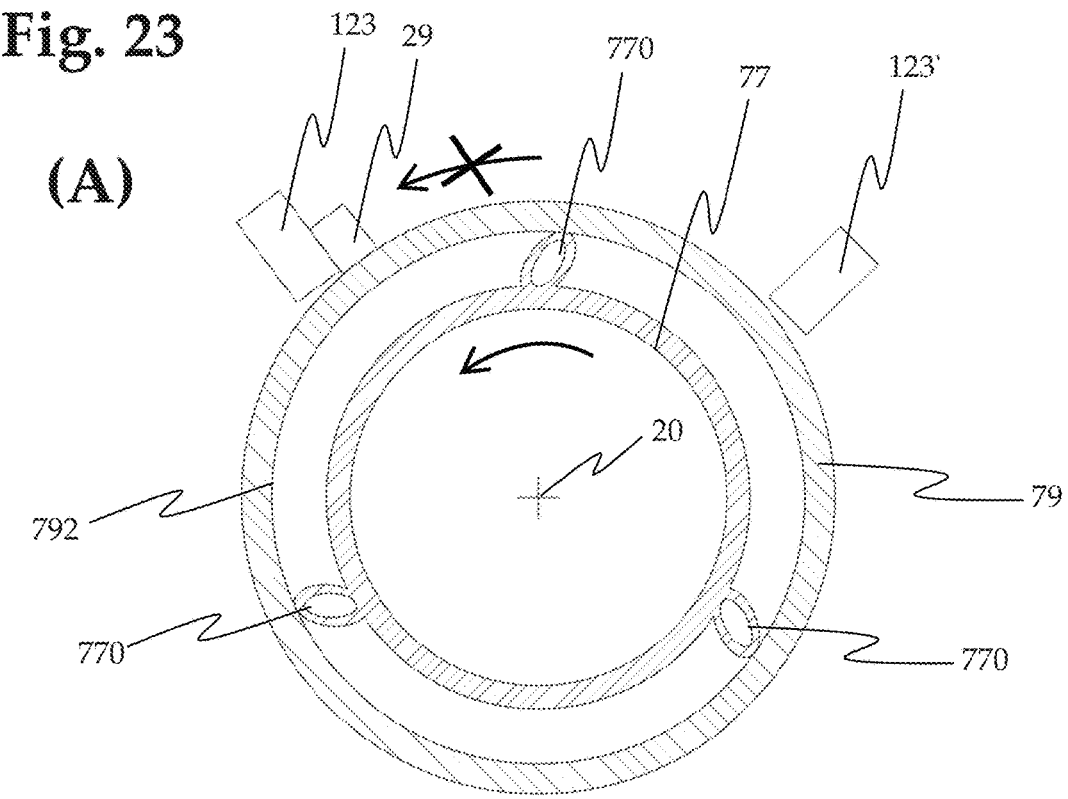
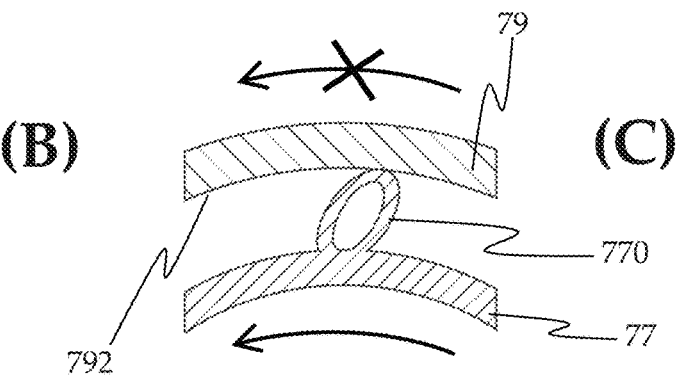
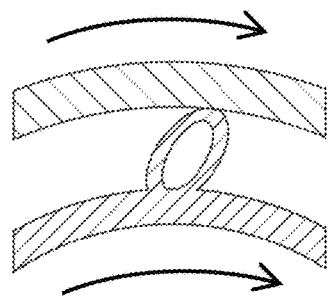
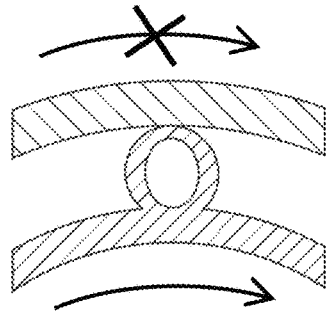
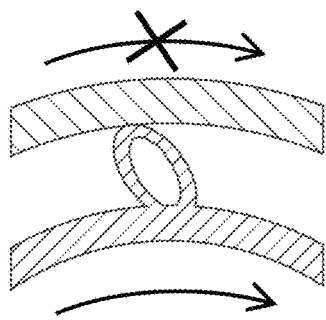

Fig. 24
(D)
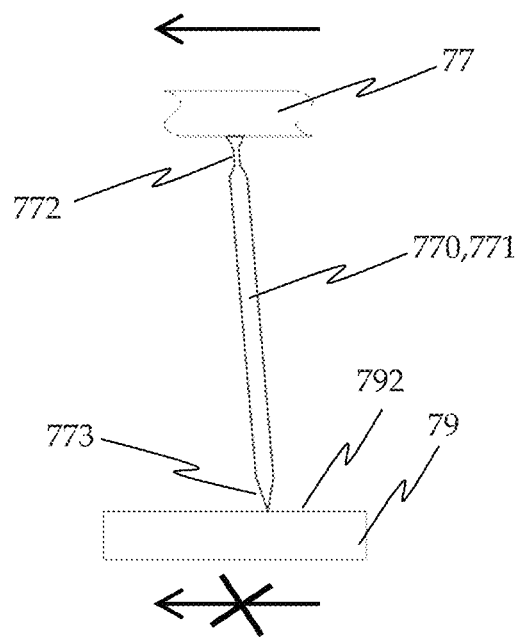
(E)
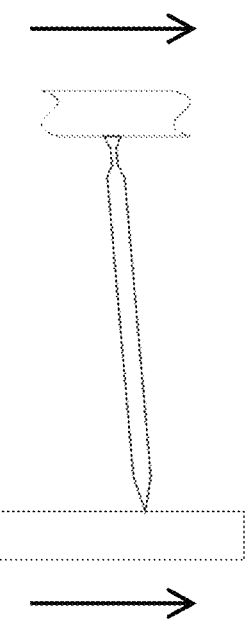
(F)
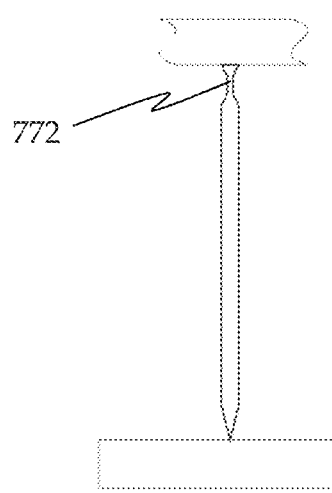
(G)
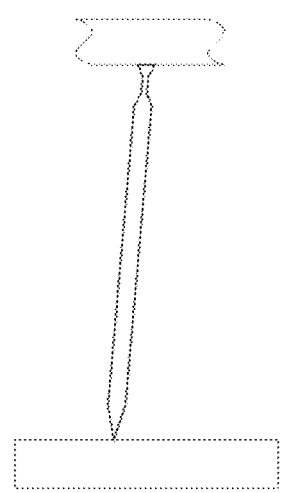

(D)

(E)

(F)

(J)

(K)

(L)

Fig. 29
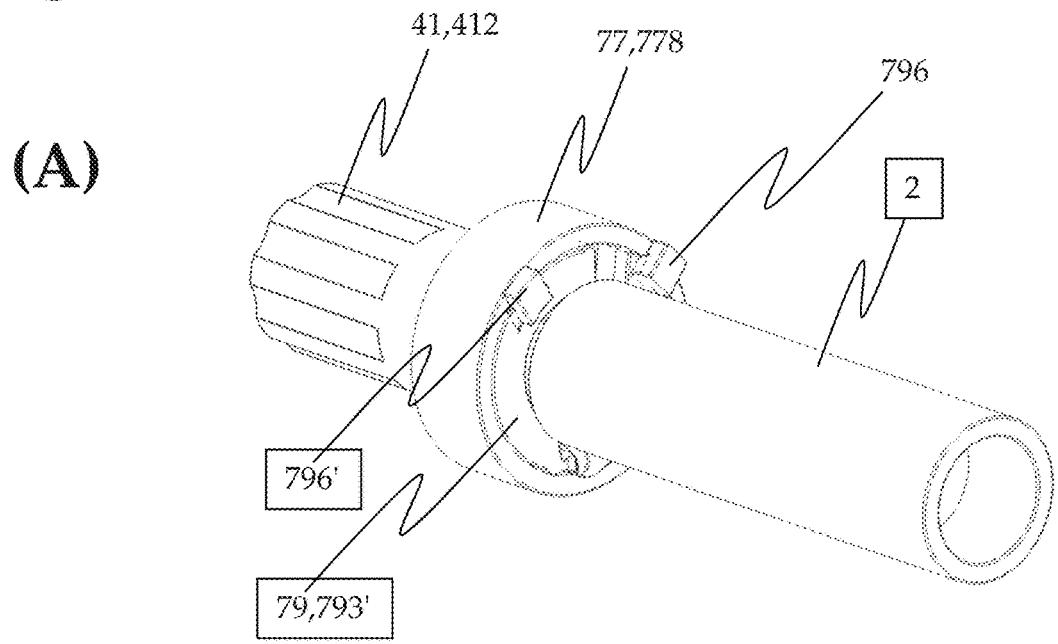
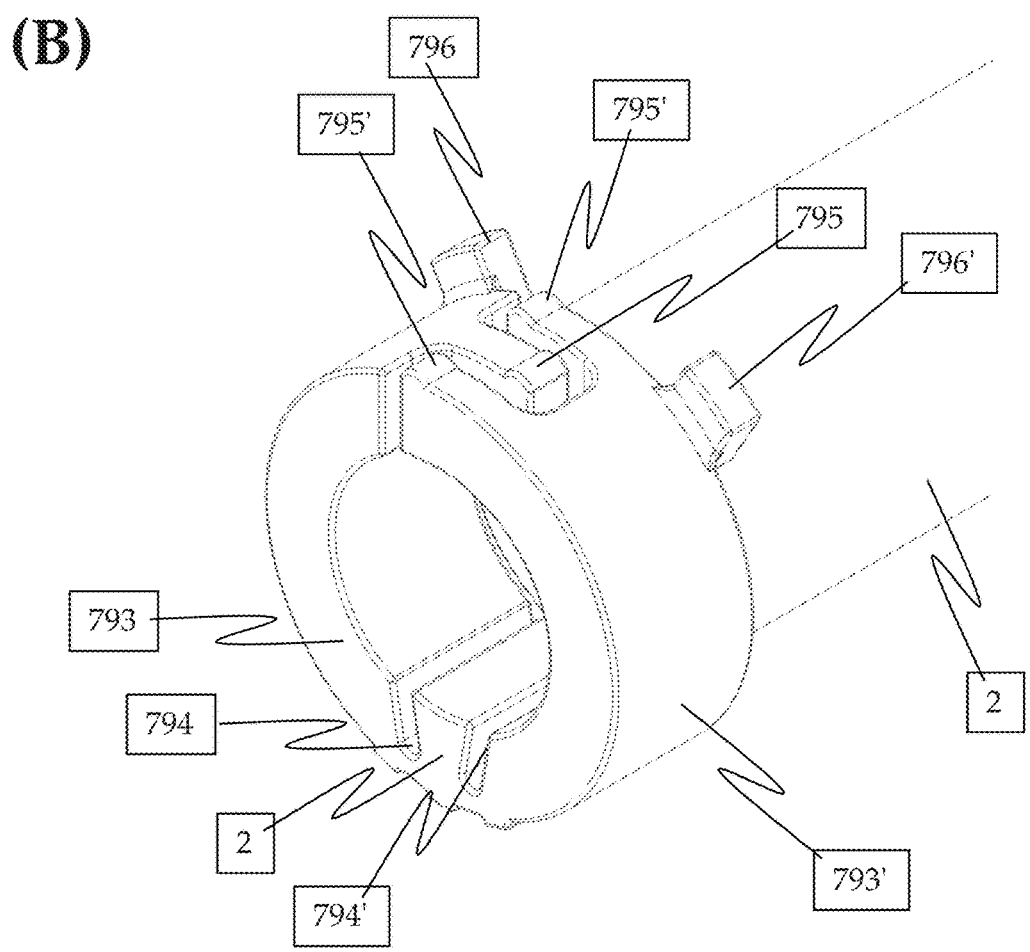

DOSING UNIT FOR AN AMBULATORY INFUSION DEVICE

CROSS REFERENCE TO RELATED APPLICATIONS

This application is a continuation of International Application No. PCT/EP2012/065972 filed Aug. 15, 2012, which claims priority to International Application No. PCT/EP2011/065242 filed Sep. 2, 2011. The contents of each of these applications are hereby incorporated by reference in their entirety into this disclosure.

TECHNICAL FIELD

The invention relates to dosing units for infusion pump devices, and infusion pump devices with such a dosing unit.

BACKGROUND

Devices for the automated release of liquid medicaments are normally used with patients who have a continuous and in the course of the day varying need of a liquid medicine which can be administered by infusion. Specific applications are, for example, certain pain therapies, cancer therapies and the treatment of diabetes mellitus, in which computer controlled infusion pump devices are used. Such devices are particularly useful for ambulatory therapy, and are generally carried attached on or near the body of a patient. The medicine reservoir often comprises medicine supply sufficient for one or several days. The liquid medicament is supplied to the patient's body from the medicine reservoir through an infusion cannula or an injection needle.

Ambulatory infusion pump devices are typically of the syringe driver type, where the liquid medicament to be administered to the patient is stored in a cylindrical glass cartridge or ampoule acting as the liquid medicament reservoir, and is conveyed to the body of the patient by displacing a plunger within the cylinder. An example of such an infusion pump device is disclosed for example in WO 01/83008 A1. A cylinder of the dosing unit comprises the complete reservoir of liquid medicament of the infusion pump device. A plunger plug arranged in the cylinder is unidirectionally displaced along the cylinder axis by a drive system via a shaft or threaded spindle.

EP 2163273 A1 of the applicants, the disclosure of which is hereby included by reference in its entirety, discloses a piston pump based dosing unit for an infusion pump device with a 4/3 or 3/3 way valve system arranged at a front end of the cylinder of the dosing unit. A plunger arranged in the cylinder of the dosing unit can be bidirectionally displaced along the cylinder axis by a spindle drive system. In one state of the valve, an inlet conduit fluidly connected to the primary reservoir is fluidly connected to the cylinder cavity, and an outlet conduit fluidly connected to the infusion tubing is disconnected from the dosing unit. This state of the valve is applied during the refill mode, when the dosing unit retracts the plunger and sucks liquid medicament from the primary reservoir into the pump cylinder/secondary reservoir. In a second state of the valve, the cylinder of the dosing unit is fluidly connected to the outlet conduit, thereby establishing a fluid connection to the body of the patient. The inlet conduit is disconnected from the dosing unit. This valve state is applied during the pump mode, when liquid medicament is conveyed from the secondary reservoir in the cylinder of the dosing unit to the subcutaneous tissue of the patient. The valve thus either allows the dosing unit to retrieve liquid from the primary reservoir, or to convey liquid from the secondary reservoir of the dosing unit toward the patient.

The valve is realized as a rotatable cylinder acting as a valve member, mounted in a fixed valve seat. The cylinder member of the valve is frictionally connected to the plunger. By rotating the plunger along the cylinder axis, the actuating means of the plunger indirectly actuate also the valve member, by rotating the cylinder/valve member within the stationary valve seat. Thus no separate actuator is needed for the valve. Furthermore the valve system and the piston pump are coupled such that in the pump mode, the valve will automatically be in the pump state, and in the refill mode, the valve will automatically be in the retrieving state. Thus also no additional control means is needed for the valve.

In order to rotate the cylinder and to switch the valve, the plunger has to exert a rotational torque on the cylinder member. At the same time the rotational torque exerted on the plunger by a drive unit has to be translated into a linear displacement of the plunger along the cylinder axis. For that purpose the plunger shaft is provided with an outer thread that interacts with an inner thread provided on the cylinder. The dosing unit is designed such that the static frictional force between plunger and cylinder member (including friction between plunger plug and cylinder wall and friction of the thread) is larger than the static friction between cylinder member and valve seat. When the drive unit rotates the shaft into one direction, the cylinder is frictionally coupled to the rotating plunger and rotates in the valve seat until finally reaching an end position, where its further rotation is mechanically blocked by a stopper. The plunger is now frictionally decoupled from the cylinder member, and any further rotation of the plunger is translated by the threads into a linear displacement along the cylinder axis. When the rotation of the plunger is reversed, the cylinder member is no longer rotationally blocked in the valve set, and plunger and cylinder member are frictionally coupled again. The cylinder member thus rotates in the valve seat in the reverse direction, actuated by the drive unit via the plunger, until a second stopper is reached, corresponding to the second valve state. The plunger is decoupled again from the blocked cylinder member, and is now linearly displaced along the cylinder axis in the opposite direction. The design of such a combined piston pump/valve system is named "valve before plunger" design, since the valve is actuated before the plunger is actuated.

In an infusion pump device as discussed above, all parts that come into contact with liquid medicament, as well as parts that are subject to friction, may be arranged in a disposable subunit. Prior to use of the infusion pump device, a fresh disposable subunit is coupled to a reusable subunit, comprising for example the electronics, the drive system, the battery, and all other parts that are not prone to contamination or wear, and can be used over a longer time period.

Since the spindle that actuates the plunger of the pump is typically made from a polymer material, and thus would be subject to wear if used over a long time period, it is advantageously also part of the disposable subunit. However, if a simple threaded rod coupled to the plunger would be used as the spindle of the spindle drive, the length of the disposable subunit would depend on the plunger position. Such a design would complicate the coupling of the disposable subunit to the reusable subunit, namely the coupling of the spindle to the drive motor.

In the dosing unit shown in EP 2163273 A1, the length of the disposable subunit is hold constant. The plunger spindle of the dosing unit comprises a plunger shaft attached to the plunger, and a coaxial plunger driving rod arranged in a longitudinal bore along its axis of the plunger shaft. The driving rod can be linearly shifted along the longitudinal bore. The cross-section of the driving rod and the longitudinal bore are chosen such that a rotational torque is effectively transmitted from the driving rod to the plunger shaft. The coupler element can be coupled to a driving unit of a reusable subunit. The linear displacement of the plunger during the spindle actuation is compensated by the two-part spindle. While the plunger shaft is linearly shifted together with the plunger, the driving rod remains on place in regard to the drive unit. The transmission of the rotational torque from the drive unit to the plunger shaft is effected by the rotational coupling between plunger shaft and driving rod.

A spindle drive, as it is also present in the above-referenced dosing unit, unavoidably has a certain thread lash. When spindle rotation is reversed, the flanks of the inner thread and the outer thread are slightly shifted in regard to each other along the longitudinal axis. In a standard single-reservoir syringe-type infusion pump, thread lash is not relevant, since the spindle drive in unidirectional. Thus after priming of the pump system there is no reversal of the spindle rotation direction. Thread lash can be potentially detrimental to metering precision for secondary-reservoir piston pump dosing units, where the rotation direction is repeatedly reversed after priming. After switching the rotational direction of the plunger, for a small rotation angle of the plunger the threads are not coupled, resulting in a rotation of the plunger without linear displacement. Furthermore the linear force exerted on the plunger may have to counteract an opposite force due to a pressure differential in the cylinder cavity. Depending on the circumstances this can lead to a small linear displacement of the plunger within the cylinder, without rotation. As a result, the metering precision of such a dosing unit may be restricted.

This precision reducing effect of the thread lash is particularly relevant when the rotation angle and/or the linear displacement of the plunger are used to determine the position of the plunger plug within the cavity and/or the volume of retrieved/conveyed liquid volume. Although such a metering measurement method is very precise, and can take into account various effects, it cannot counterbalance thread lash, since thread lash cannot be detected such a method.

Counter spindle drives are used to avoid thread lash in high precision linear motors, for example for machining devices such as lathes. However, such complex drives are not applicable for infusion pump devices, since they are too voluminous and complex.

SUMMARY

In at least one embodiment of the present disclosure, a dosing unit for an infusion pump device is disclosed. At least one embodiment of the dosing unit of the present disclosure comprises a piston pump with a pump cylinder, a plunger arranged within said cylinder, and a plunger driving part provided for transmitting rotational torque from a driving unit to the plunger without itself being linearly displaced. The cylinder, the plunger and the plunger driving part are coaxially arranged along a longitudinal axis and rotatable around said axis in regard to static parts of the dosing unit. The plunger has a shaft with a thread and the cylinder has a threaded sleeve part with a thread. One of the two threads is an outer thread and the other one is an inner thread, said two threads engaging with each other in such a way that a rotational movement of the plunger around the longitudinal axis results in an additional linear displacement of the plunger along said longitudinal axis. The plunger driving part has a driving rod that is arranged in a longitudinal bore of the plunger shaft, the driving rod being linearly displaceable within the longitudinal bore along the longitudinal axis, and being rotationally engaged with the plunger shaft. One or more first coupling parts are mounted to or are integral with the cylinder, and one or more second coupling parts are mounted to or are integral with the plunger driving part and/or the plunger. The first and second coupling parts interacting in such a way that:

the first and second coupling parts are bidirectionally switchable between a first state and a second state, by reversing the rotation direction of the plunger driving part;

the first and second coupling parts are unidirectionally switchable from the first state to the second state, by mechanically blocking cylinder rotation or actuating the first coupling part; and the cylinder is rotationally coupled to the plunger driving part in the first state of the first and second coupling parts; and not rotationally coupled in the second state.

In at least one embodiment of the present disclosure, the one or more first coupling parts are mounted to or are integral with the cylinder and/or the plunger driving part, and one or more second coupling parts are mounted to or are integral with the plunger driving part and/or the plunger; the first and second coupling parts interacting in such a way that the cylinder is rotationally coupled to the plunger on certain linear positions of the plunger in regard to the cylinder and is not rotationally coupled to the plunger on the other positions.

In at least one embodiment of the present disclosure, the one or more first coupling parts are mounted to or are integral with the cylinder, and one or more second coupling parts are mounted to or are integral with the plunger driving part; the first and second coupling parts interacting in such a way that the cylinder is rotationally decoupled from the plunger driving part on certain angular orientations of the cylinder in regard to static parts of the dosing unit, and is rotationally coupled on the other orientations.

In at least one embodiment of the dosing unit according to the disclosure the coupling parts are part of the plunger driving part and do a direct (selective) torque transmission from the plunger driving part to the cylinder. Alternatively the coupling parts are, at least partly, part of the plunger and do an indirect (selective) torque transmission from the plunger driving part to the cylinder, via the plunger. The plunger driving part is in at least one embodiment distinct from both cylinder and plunger.

A functional principle of the disclosed dosing unit is that the plunger driving part receives a rotational torque from some drive and provides that torque either to the plunger only (decoupled state) or to both plunger and cylinder (coupled state). The plunger driving part accordingly may fulfil the functions of transforming a pure rotational drive movement into a screw-like combined rotational and linear movement of the plunger, and selectively rotationally coupling the cylinder to the drive.

In at least one embodiment of a dosing unit of the present disclosure, the dosing unit has reduced energy consumption, since the cylinder can be decoupled from the drive unit, as long as the valve does not have to be switched.

In at least one embodiment of the dosing unit, a first coupling part is mounted to or is integral with the cylinder, and a second coupling part is mounted to or is integral with the plunger driving part. The first and/or the second coupling parts comprise one or more bistable elements that can be in a first configuration where the bistable elements rotationally couple the first and second coupling parts by static friction or positive locking when the plunger driving part rotates clockwise, and do not rotationally couple the first and second coupling parts when the plunger driving part rotates counter-clockwise. In a second configuration, the bistable elements rotationally couple the first and second coupling parts by static friction or positive locking when the plunger driving part rotates counter-clockwise, and do not rotationally couple the first and second coupling parts when the plunger driving part rotates clockwise.

In the at least one embodiment mentioned above, where the first and second coupling parts are unidirectionally switchable from a first state to a second state, by mechanically blocking cylinder rotation, such a change occurs, more generally spoken, if the torque for rotating the cylinder exceeds a maximum torque that can be transmitted via the coupling from the bistable friction elements to the cylinder. This change occurs in the mechanically blocked state, where the torque for further rotating the cylinder becomes essentially infinite.

In at least one embodiment of the present disclosure, the bistable elements are friction elements that are switchable between two configurations, and that the rotational coupling is a static frictional coupling. Additionally, the bistable friction elements may be switchable between the two configurations by reversing the rotation direction of the plunger driving part in case the first and second coupling parts are not rotationally coupled; and by reversing the rotation direction of the plunger driving part and blocking cylinder rotation in case the first and second coupling parts are rotationally coupled. Further, the cylinder rotation may be blocked on certain angular orientations of the cylinder in regard to the static parts of the dosing unit.

In at least one embodiment of the present disclosure, the bistable elements are ratchet mechanisms that are switchable between two configurations, and that the rotational coupling is given when the ratchet mechanism is locked. The bistable ratchet mechanisms may be switchable between the two states by reversing the rotation direction of the plunger driving part in case the ratchet mechanism is locked; and by reversing the rotation direction of the plunger driving part and additionally actuating the ratchet mechanism in case the ratchet mechanism is not locked. Further, the ratchet mechanism may be actuated by switching elements mounted to or being integral with the static parts of the dosing unit.

In at least one embodiment of the present disclosure, the first coupling parts comprise first ramps provided on the plunger driving rod, and the second coupling parts comprise second ramps provided on a structure pivotably mounted on the plunger shaft. The structure carries portions of the outer thread. The first and second ramps are arranged such that on at least one linear position of the plunger in regard to the cylinder some of the first ramps abut some of the second ramps, and press the outer thread portions radially outwards onto the inner thread of the cylinder, thereby frictionally coupling the cylinder and the plunger.

In at least one embodiment of the present disclosure, the one or more first coupling parts are first friction elements mounted to or being integral with the cylinder, and the one or more second coupling parts are second friction elements mounted to or being integral with the plunger. At certain longitudinal positions of the plunger in regard to the cylinder one of the first friction elements frictionally engages with one of the second friction elements, thereby frictionally coupling the cylinder and the plunger. Additionally, the one or more first friction element may be a hollow cylinder, and the one or more second friction element may be a friction cylinder, which frictionally engages with the hollow cylinder when the friction cylinder is located in the hollow cylinder.

In at least one embodiment of the present disclosure, the one or more first coupling parts are first stopper elements mounted to or being integral with the cylinder, and the one or more second coupling parts are second stopper elements mounted to or being integral with the plunger. At certain longitudinal positions of the plunger in regard to the cylinder one of the first stopper elements abuts with one of the second stopper elements, thereby blocking the further linear displacement of the plunger, and releasably jamming the inner thread of the cylinder and the outer thread of the plunger. In at least one embodiment, the stopper elements are disks.

In at least one embodiment of the present disclosure, the dosing unit has a cylinder coupling part as the first coupling part and a plunger coupling part as the second coupling part. The cylinder coupling part comprises first locking elements and the plunger coupling part comprises second locking elements, which releasably lock the plunger to the cylinder at certain longitudinal positions of the plunger in regard to the cylinder.

In at least one embodiment of the dosing unit, a first coupling part is mounted to or is integral with the cylinder, and a second coupling part is mounted to or is integral with the plunger driving part. The two coupling parts are frictionally coupled. The frictional coupling is releasable by switching elements mounted to or being integral with the static parts of the dosing unit.

In at least one embodiment of the dosing unit of the present disclosure, the metering precision is increased due to the reduction of metering errors due to uncontrolled plunger displacement. Furthermore the separation in time of the valve switching process and the plunger displacement process is more precise, since the thread friction force, adding to the friction force between cylinder valve member and plunger, remains essentially constant when the plunger rotation direction is reversed.

In at least one embodiment of the dosing unit of the present disclosure, a separate bias force element is provided that biases the two threads in regard to each other along the longitudinal axis, such that the threaded engagement of inner thread and outer thread is free of play independent of a direction of a rotational movement and linear displacement of the plunger in regard to the cylinder. In at least one embodiment, the plunger thread is an outer thread and the cylinder thread is an inner thread.

In at least one embodiment of the dosing unit of the present disclosure, the bias force element subjects the plunger shaft to a force perpendicular to the longitudinal axis, thereby pressing a portion of the plunger thread onto a portion of the cylinder thread. The bias force element may comprise a radially biased flat surface that abuts the lateral surface of an outer one of the two threads.

In at least one embodiment of the dosing unit of the present disclosure, one or more portions of the cylinder thread or the plunger thread are pivotably mounted on the cylinder, or on the plunger shaft, respectively. Further, a spring element (such as a tension ring) may be is provided, which radially biases the pivotably mounted thread portions toward the other thread.

In at least one embodiment of the dosing unit of the present disclosure, the bias force element comprises a tensioned segment of wire that is mounted to the cylinder or the plunger and is arranged in such a way that it is located in a groove segment of the outer thread and exercises a bias force perpendicular to the longitudinal axis.

In at least one embodiment of the dosing unit of the present disclosure, the bias force element comprises a threaded element, which is coaxially mounted on the first threaded sleeve or on the plunger shaft, and is longitudinally shiftable in regard to the first threaded sleeve or the plunger shaft, respectively. The threaded element has a thread portion engaging with the plunger thread or the cylinder thread, respectively. Further the threaded element may have a spring element that subjects the threaded element to an axial bias force in regard to the first threaded sleeve or the plunger shaft, respectively.

In at least one embodiment of the dosing unit of the present disclosure, the bias force element comprises one or more spring elements with inner or outer thread segments, such that said inner or outer thread segments are radially biased toward the outer or inner thread. The inner or outer thread segments act as the inner or outer thread, respectively.

In at least one embodiment the bias force element is elastic. Additionally, the bias force element may be made from a material that is different from the material of the cylinder and/or the plunger. Further, the bias force element can be made from metal, and alternatively or in addition the cylinder and/or the plunger can be made from polymer.

In at least one embodiment, an infusion pump device according to the disclosure comprises a dosing unit according to the disclosure.

BRIEF DESCRIPTION OF THE DRAWINGS

The features and advantages of the present disclosure, and the manner of attaining them, will be more apparent and better understood by reference to the following descriptions taken in conjunction with the accompanying figures, wherein:

FIG. 1 schematically shows a possible embodiment of a dosing unit according to at least one embodiment of the disclosure, (A) in a longitudinal section along the cylinder axis, and (B) in a cross section through the plunger shaft and the plunger driving rod along plane A-A.

FIG. 2 schematically shows (A) a detail view of at least one embodiment of a thread lash reducing arrangement as shown in FIG. 1, and (B) a view of one portion of the thread lash reducing arrangement of (A).

FIG. 3 schematically shows at least one embodiment thread lash reducing arrangement in a dosing unit, with (A) one thread interaction and (B) multiple tread interactions according to the present disclosure.

FIG. 5 depicts at least one embodiment of a dosing unit, with a ring-like metal spring element as a radial bias element, (A) in top view, (B) in a longitudinal section along plane A-A, and (C) in a cross-section along plane B-B. The radial bias force element is shown in (D).

FIG. 6 schematically shows a further embodiment of a radial bias force element, (A) in a longitudinal view on the split end of the plunger shaft, and (B) in a side view on the end of the plunger shaft.

FIG. 8 shows at least one embodiment of a thread lash reduction arrangement according to the present disclosure, with four threaded claws at the distal end of the cylinder engaging with a threaded plunger shaft, (A) in a side view with view on the distal end, and (B) in a longitudinal section along plane A-A.

FIG. 11 shows at least one embodiment of a thread lash reduction arrangement according to the present disclosure, with an axially biased threaded sleeve, (A) in a longitudinal section through plunger shaft, threaded sleeve and axial bias force element, and (B) in a schematical detail view of the interacting thread portions. (C) discloses yet a further variant of a thread lash reduction arrangement, with an axially biased threaded plunger shaft, a longitudinal section through plunger shaft, threaded sleeve and axial bias force element.

FIG. 13 schematically shows the plunger of FIG. 12, (A) in a longitudinal section along plane A-A, (B) in a cross-section along plane B-B, and (C) in a cross-section along plane C-C.

FIG. 14 schematically shows the driving rod of FIG. 12, (A) in a side view, (B) in a top view, and (C) in a cross-section along plane D-D.

FIG. 16 schematically shows at least one embodiment of a dosing unit with controlled friction between plunger and cylinder according to the present disclosure, (A) with the plunger in a start position, and (B) with the plunger in a maximum position. A detail of FIG. 16(A) is shown in (C), explaining how the driving rod controls the friction between plunger and cylinder.

FIG. 18 schematically shows at least one embodiment of a dosing unit of the present disclosure with controlled friction between plunger and cylinder, (A) with the plunger in a start position, and (B) with the plunger in a maximum position.

FIG. 20 schematically depicts a longitudinal section of at least one embodiment of a dosing unit of the present disclosure, in which the cylinder is positively locked to the plunger at certain longitudinal positions, (A) with the plunger in a start position, (B) with the plunger in a medium position, and (C) with the plunger in a maximum position.

FIG. 23 schematically shows at least one embodiment of a coupling system of the present disclosure that allows switching the valve of a dosing unit at any longitudinal position of the plunger, (A) in a cross section, and (B) to (E) in detail views of different steps during the valve switching.

FIG. 29 schematically shows at least one embodiment of a controlled coupling between cylinder and driving rod, (A) in a perspective view on the interacting coupling parts, and (B) in a perspective view of the cylinder coupling part alone.

DETAILED DESCRIPTION

Figure 4:
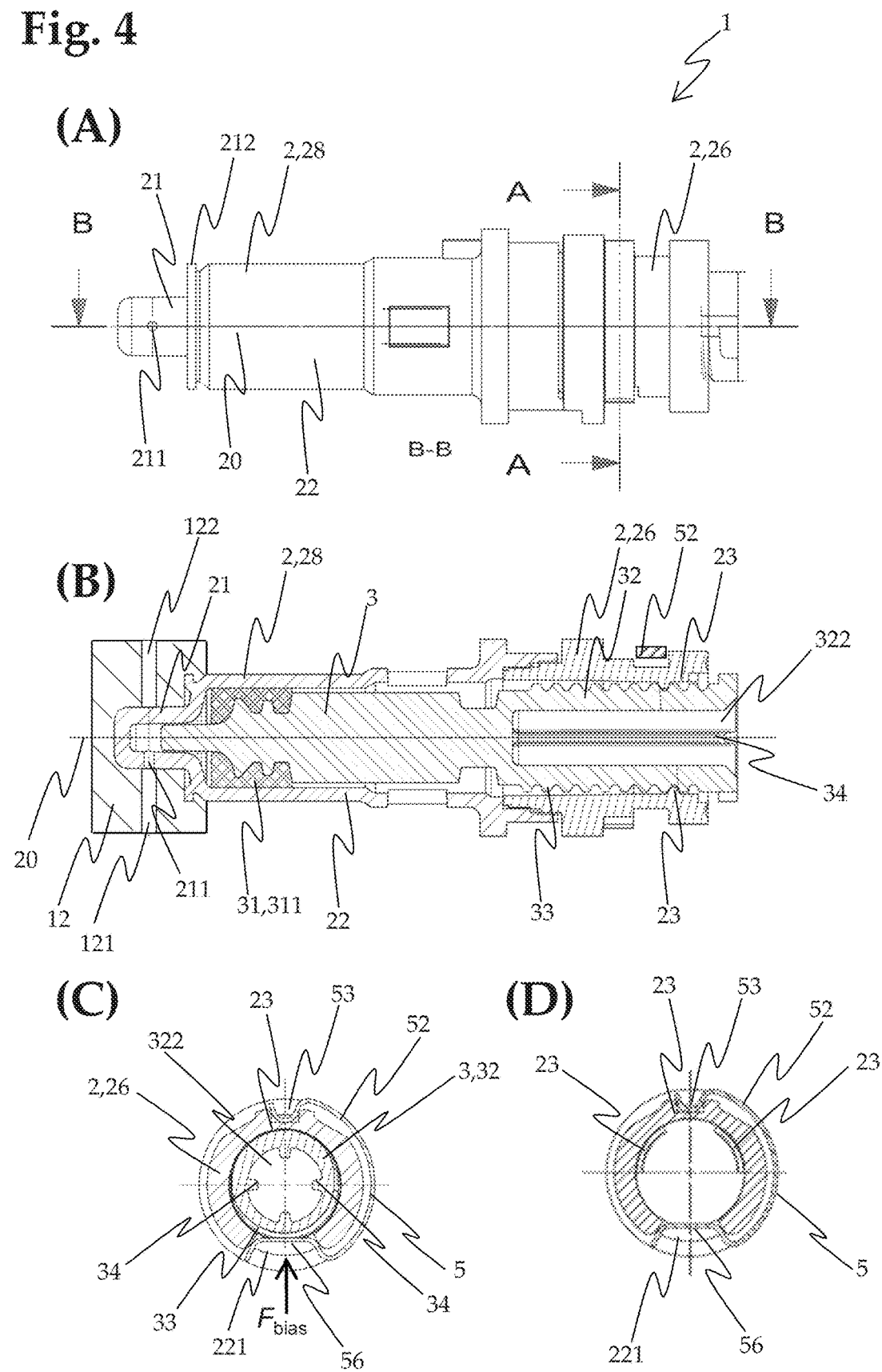
FIG. 4 depicts at least one embodiment of an dosing unit of the present disclosure without thread lash, with a ring-like metal spring element as a radial bias element, (A) in a top view, (B) in a longitudinal section along plane B-B, and in a cross-section along plane A-A, (C) with the plunger shaft, and (D) without the plunger shaft. The plunger is shown (E) without the plug sealing element material in top view, (F) in a cross-section along plane C-C, and (G) in side view with view along the longitudinal axis on the bore. The radial bias force element is shown in (H).
Figure 4:
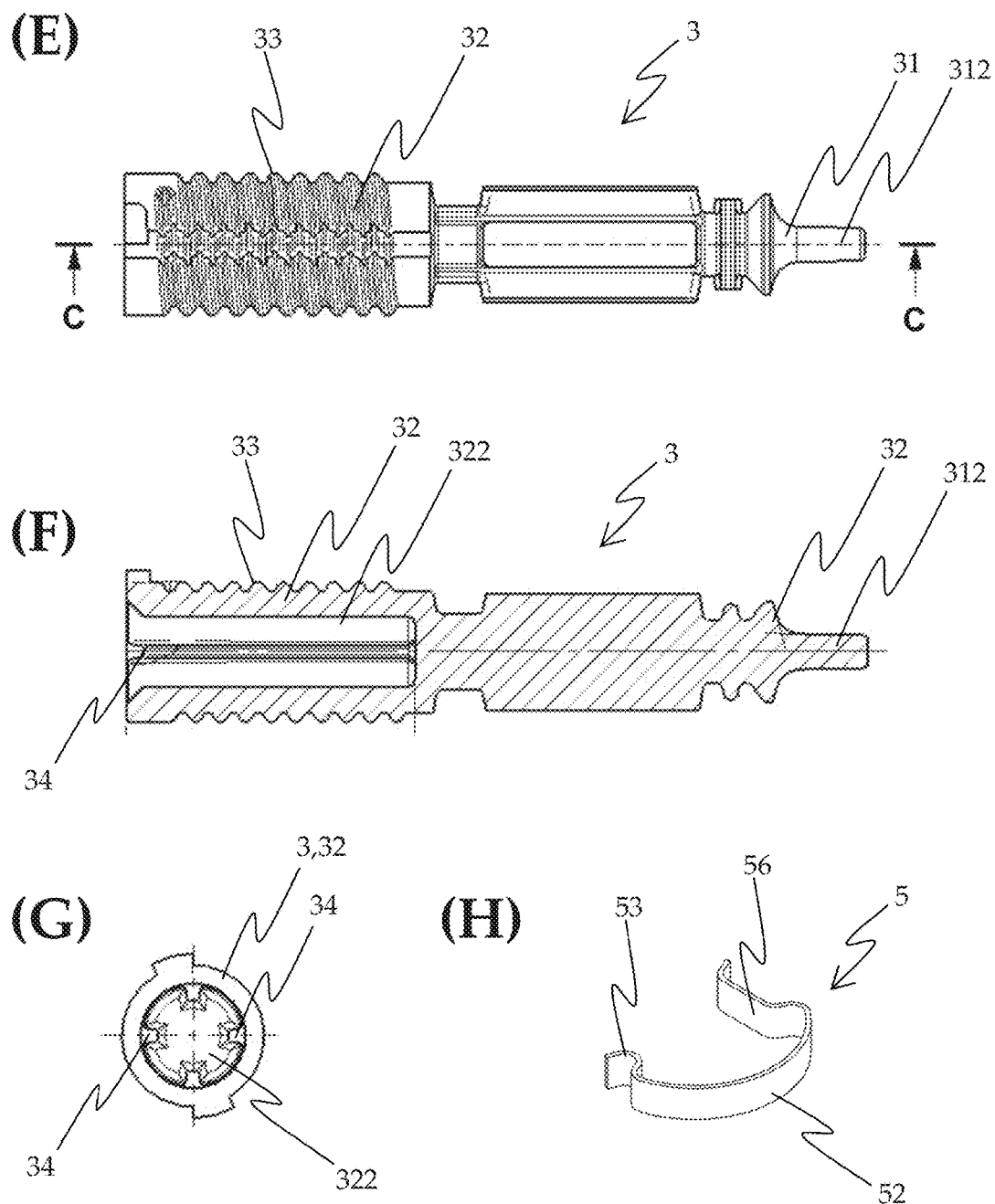

A dosing unit without thread-lash is advantageous for several reasons. The metering precision is increased due to the reduction of metering errors due to uncontrolled plunger displacement. Furthermore the separation in time of the valve switching process and the plunger displacement process is more precise, since the thread friction force, adding to the friction force between cylinder valve member and plunger, remains essentially constant when the plunger rotation direction is reversed.

A self-biasing polymer plunger shaft for thread-lash reduction has the disadvantage that its bias force deteriorates over time in an irreproducible manner, which eventually reduces the acceptable shelf time of a disposable dosing unit prior to first use in an ambulatory infusion pump device. In an advantageous dosing unit according to this disclosure, a separate bias force element is provided, thereby allowing using a plunger without detrimental mechanical stress.

At least one embodiment of a dosing unit 1 according to the present disclosure is schematically depicted in FIG. 1. A cylinder valve member 2 is rotatably mounted in a stationary valve seat 12. A plunger 3 with a plug 31 and a shaft 32 is arranged in the cylinder 2. The plunger plug 31 sealingly closes the cylinder, thereby defining a metering cavity 11 between the cylinder head 21 and the plug. In the figure, the valve formed by the valve seat 12 and the cylinder valve member 2 is in one of its two operational valve states, where an inlet 121 is fluidly connected to the metering cavity 11 through an opening 211 in the cylinder head. The inlet 121 is fluidly connected to a primary reservoir of an infusion pump device (not shown). A downstream outlet 122 toward an infusion set (not shown) is disconnected from the metering cavity 11.

The plunger plug 31 is attached to a plunger shaft 32, which is provided with an outer thread 33 that interacts with an inner thread 23 arranged on the cylinder. The plunger shaft 32 is provided with a longitudinal bore 322 along its axis, having a square cross-section, in which a rod 41 of a plunger driving part 4 is arranged. The plunger driving rod 41 has a square cross-section corresponding to the longitudinal bore 322 of the plunger shaft. Thus the rod 41 can be shifted with only minimum friction in the longitudinal bore 322, while at the same time efficiently transmitting a rotational torque around the axis 20 from the plunger driving part 4 to the plunger 3. Plunger shaft and plunger driving rod are designed such that the bore 322 is vented toward atmosphere.

The plunger shaft 32 and the plunger driving rod 41 together form the plunger spindle of the dosing unit. The plunger driving part 4 is rotationally coupled to a driving unit of the infusion pump device (not shown). In an embodiment of the dosing unit that is designed as a disposable element, which is intended to be replaced in regular intervals, the plunger driving part may be provided with a drive unit coupling 42 for releasably coupling the plunger coupler to the drive unit. During operation, the drive unit (not shown) exerts a rotational force on the plunger driving part 4 via the drive unit coupling 42, and the plunger coupler transmits this rotational torque to the plunger 3. While the plunger driving rod remains stationary along the longitudinal axis, the plunger is linearly displaced along the axis.

Since the frictional coupling between plunger and cylinder is larger than between cylinder and valve seat, the plunger is frictionally coupled to the cylinder member, as long as the cylinder has not yet rotated to a blocking position, corresponding to an operational valve state. In the blocking position of the valve, the now decoupled rotational movement of the plunger is translated into a linear movement of the plunger, by the spindle drive realized by the outer thread 33 of the plunger and the inner thread 23 of the cylinder.

In at least one embodiment shown in FIG. 1, the thread lash is minimized by an advantageous thread lash reduction arrangement. The inner thread of the cylinder is realized as a single thread segment 23 having a segment angle of 180°. or less. A separate radial bias force element 5 is provided on the cylinder wall, on the side opposite to the inner thread segment 23. Said bias force element 5 is realized in the given embodiment with a radially biased flat surface element 56 pressing on the outer thread 33 of the shaft 32, thereby pressing the outer thread 33 on the opposite side of the shaft radially onto the thread segment 23. A defined bias force is generated by a spring element 52 or other suitable resilient element, which in the figure is shown only schematically.

The principle of the applied thread lash reduction arrangement is shown in more detail in FIGS. 2(a) and (b), schematically depicting a longitudinal section through a portion of a plunger shaft 32 with outer trapezoid thread 33, interacting with a trapezoid thread segment 23 on the cylinder wall 22. On the opposite side of the thread segment 23, a radial bias force element 5 is arranged, exerting a radial bias force $F_{bias}$ perpendicular to the cylinder axis 20. The radial bias force element 5 is here realized as a flat element 56, abutting the outer surface 331 of the spindle 32, 33, and biased by a helical spring 52. The bias element exerts a radial force on the outer thread 33 surface and the shaft 32, without directly interacting with the thread 33. As a result, there is a radial force $F_{bias}$ between thread 33 and thread segment 23, resulting to which the two threads closely abut each other, without a thread lash. Thus with at least one exemplary arrangement there will be no undefined plunger motion upon reversal of the rotation direction, or pressure differentials in the metering chamber.

The parameters of at least one exemplary thread as such, namely thread form, flank angle, and helical angle are mainly defined by the intended application, namely a self-locking spindle drive. With a thread having a flank angle α, and neglecting the comparably small helix angle of the thread, an axial force $F_a x$ acting on the plunger shaft 32 will have a force component $F_a = \cos(\alpha) F_{ax}$ parallel to the surface of the thread flank. Similarly there acts a force component $F_b = \sin(\alpha) F_{bias}$ parallel to the flank surface, in the opposite direction. Thus as long as biasing force component $F_b$ is larger than an axial force component $F_a$ exerted on the plunger, or $\sin(\alpha) F_{bias} > \cos(\alpha) F_a x$, the axial force cannot overcome the bias force, and the outer thread flank cannot slide along the flank of the thread segment 23, which would lead to a axial shift of the plunger.

In at least one embodiment, the biasing force should be properly adjusted to avoid increased thread friction, and thus for the battery life time of a corresponding infusion pump device.

The maximum axial force $F_{ax,max}$ that may occur on the plunger during normal operation can be estimated. Based on that upper limit an appropriate minimum radial force of the bias force element is determined, as $F_{bias,min} = \cot(\alpha) F_{ax}$. The smaller the flank angle the smaller is thread friction during operation, which is advantageous in regard to energy consumption. On the other hand it considerably increases the necessary bias force. An advantageous compromise in a dosing unit according to the disclosure is for example a trapezoid thread with flank angle 60° (cot 60°=0.58) and helical angle 3.4°.

In at least one embodiment, the bias force is generated by a spring element, for example a metal helical spring. Other types of resilient elements are possible. The material of the resilient element is chosen such that it does not deteriorate over time in regard to the spring force, thereby allowing a long shelf time prior first use.

The plunger shaft and the cylinder wall including thread segment 23 of at least one embodiment may be manufactured from a thermoplastic polymer material compatible for medicinal applications. It should furthermore provide elasticity parameters suitable for application in self-locking spindle drives. Exemplary materials that may be used in at least one embodiment include for example polyamide (PA), polypropylene (PP), methyl methacrylate butadiene styrene terpolymer (MBS), and polybutylene terephthalate (PBT).

At least one embodiment of a thread lash reducing arrangement is shown in FIG. 3(a), where the bias force element 5 is realized as a biased thread segment 51, interacting with the outer thread 33. A further embodiment is shown in FIG. 3(b), where three parallel thread segments 23 are provided. Such a variant with more than one thread flank interacting is less advantageous than the variants discussed before, since the actual forces acting on the thread can be determined less precisely due to manufacturing tolerances.

At least one embodiment of a dosing unit of the present disclosure is disclosed in FIG. 4. The pump cylinder/valve member 2 comprises two parts 28, 26, and is rotatably arranged in the valve seat 12. The plunger plug 31 is arranged in a proximal (proximal meaning "toward the valve") cavity part 28 of the cylinder, together defining the variable metering cavity. The plug 31 comprises a plug sealing element 311, sealingly closing the metering cavity. The sealing element 311 is advantageously made from an elastic thermoplastic polymer. The plunger can be manufactured e.g. by two component injection moulding of plunger sealing element and plunger rod. In the longitudinal section given in FIG. 4(b), in which the valve seat 12 is shown, the radial opening 211 in the cylinder head wall 21 is fluidly connected to inlet 121, while the outlet 122 is disconnected from the metering cavity.

The threaded 33 plunger shaft 32 is arranged in a distal (distal meaning "away from the valve, toward the drive unit") threaded sleeve part 26 of the cylinder, where the outer thread 33 interacts with two inner thread segments 23 of the threaded sleeve 26. The proximal cylinder part 22 and the distal part/threaded sleeve 26 of the cylinder are attached together with a suitable locking mechanism, for example by ultrasonic welding. Assembling the cylinder from two separate parts has the advantage that the single pieces are easier to manufacture. Furthermore it allows optimising of the materials used. The material of the proximal cylinder part 22 can be chosen in regard to compatibility with medical liquids and the interaction with the material of the plug sealing element 311. The material of the distal threaded sleeve 26 can be chosen in regard to a reliable thread interaction with the plunger shaft 32.

The plunger shaft 32 is provided with a longitudinal bore 322 along its axis, in which a rod of a plunger driving part (not shown) can be arranged. Four longitudinal cams or rips 34 are arranged along the bore 322 of the plunger shaft, intended to interact with corresponding slots on the plunger driving rod. The cams 34 in at least one embodiment allow for efficiently transmitting a rotational torque from the plunger coupler to the plunger. At the same time there is only low friction along the longitudinal axis 20.

The necessary bias force to remove tread lash is provided by a radial bias force element 5 in the form of a half-ring-like metal spring 52, having a flat portion 56 at one end of the spring 52, and a locking structure 53 on the other end. When mounted to the cylinder, the locking structure is arranged in a corresponding recession on the outer cylinder wall. The flat element 56 is arranged in an opening 221 in the threaded sleeve 26, and abuts the thread 33 of the plunger shaft 32.

During assembly, the spring element 52 may be slightly deformed. When the locking structure 53 and the flat portion 56 snap into the corresponding recessions and openings, the spring element is positively locked to the distal cylinder element, with a spring force due to the remaining radial deformation. Due to this remaining spring force the radial bias force element 5 generates a radial biasing force between the two inner thread segments 23 of the threaded sleeve 26 and the outer thread 33.

Since the bias spring element 52 in at least one embodiment has a very simple structure and can be easily mounted to the cylinder, the dosing unit can be manufactured and assembled very efficiently. At the same time the spring element provides a reliable and constant radial bias force $F_{bias}$. The spring element 52 may in at least one embodiment be made from spring band steel, for example spring band steel 1.4310.

The use of two inner thread segments 23 in combination with a single biased flat surface element 56 is particularly advantageous, compared to a single threaded segment as described for FIG. 1. Since said two inner thread segments and the flat surface element provide a three-point mounting (instead of two mounting points), the outer thread of the plunger shaft 32 is more stably mounted.

Figure 26:
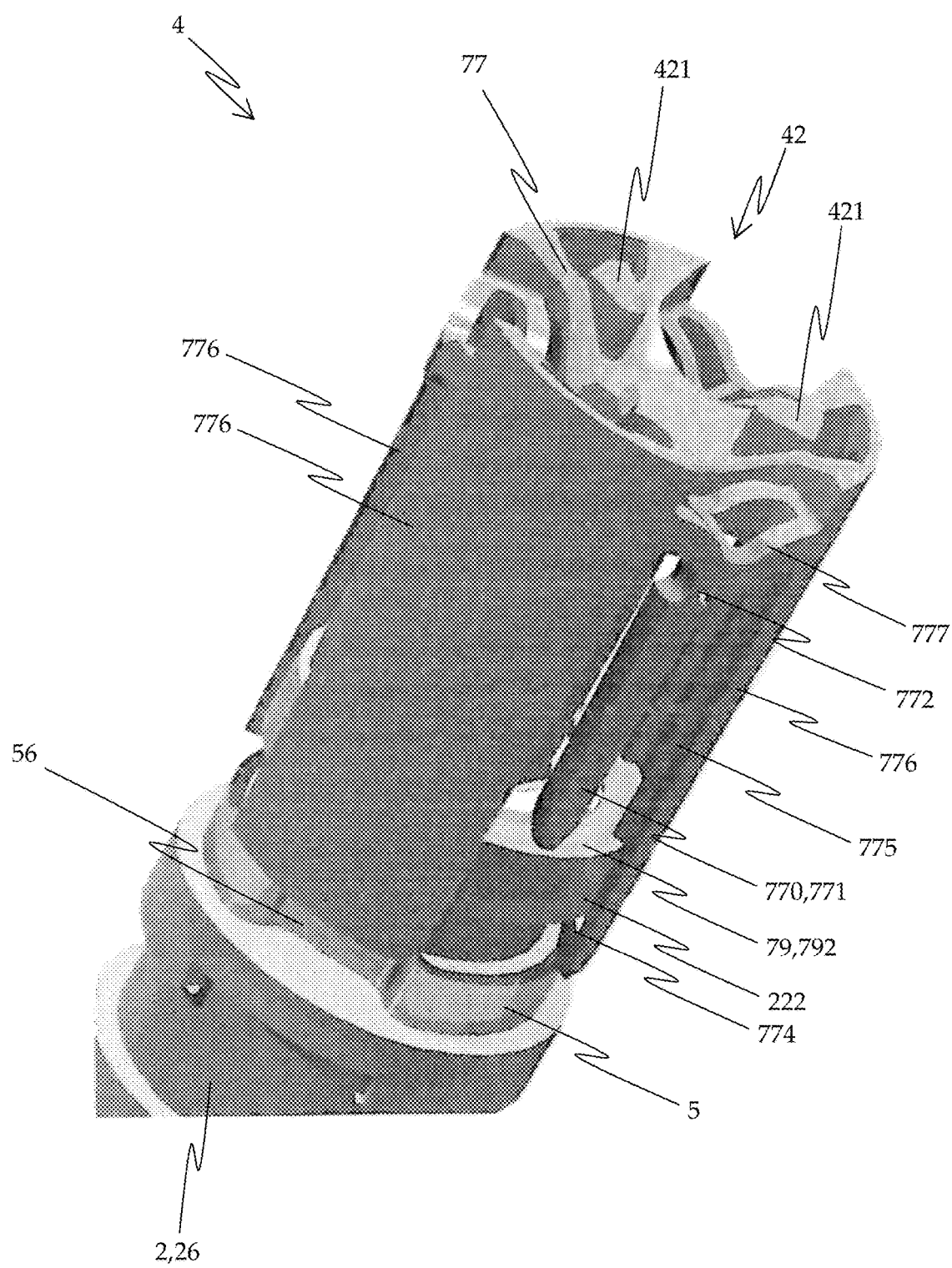
FIG. 26 shows a perspective view of at least one embodiment of a dosing unit with the cylinder/plunger combination with thread lash reduction arrangement as shown in FIG. 5, and with a cylinder/driving rod coupling arrangement similar to FIG. 24.
Figure 27:
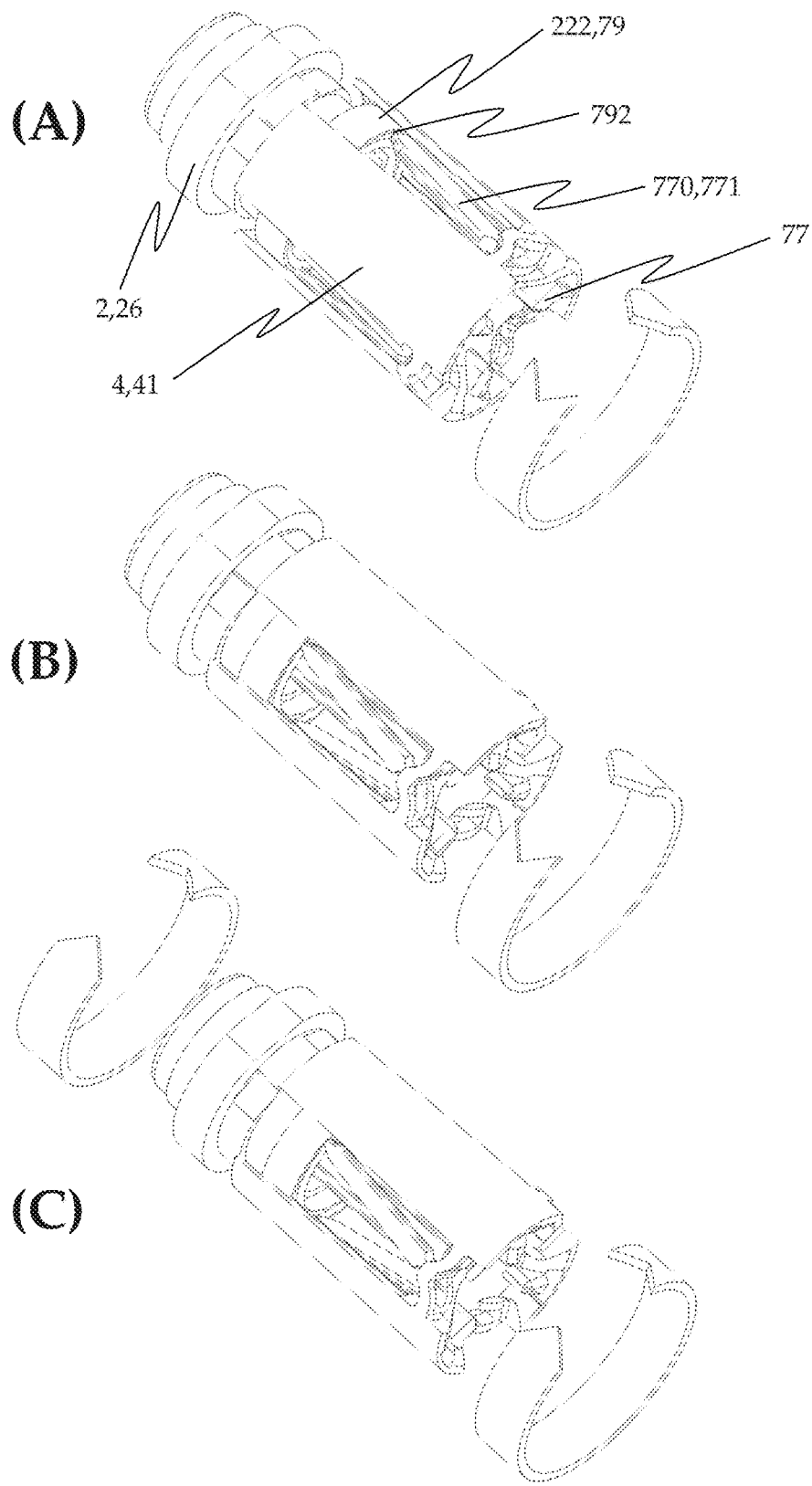
Figure 27:
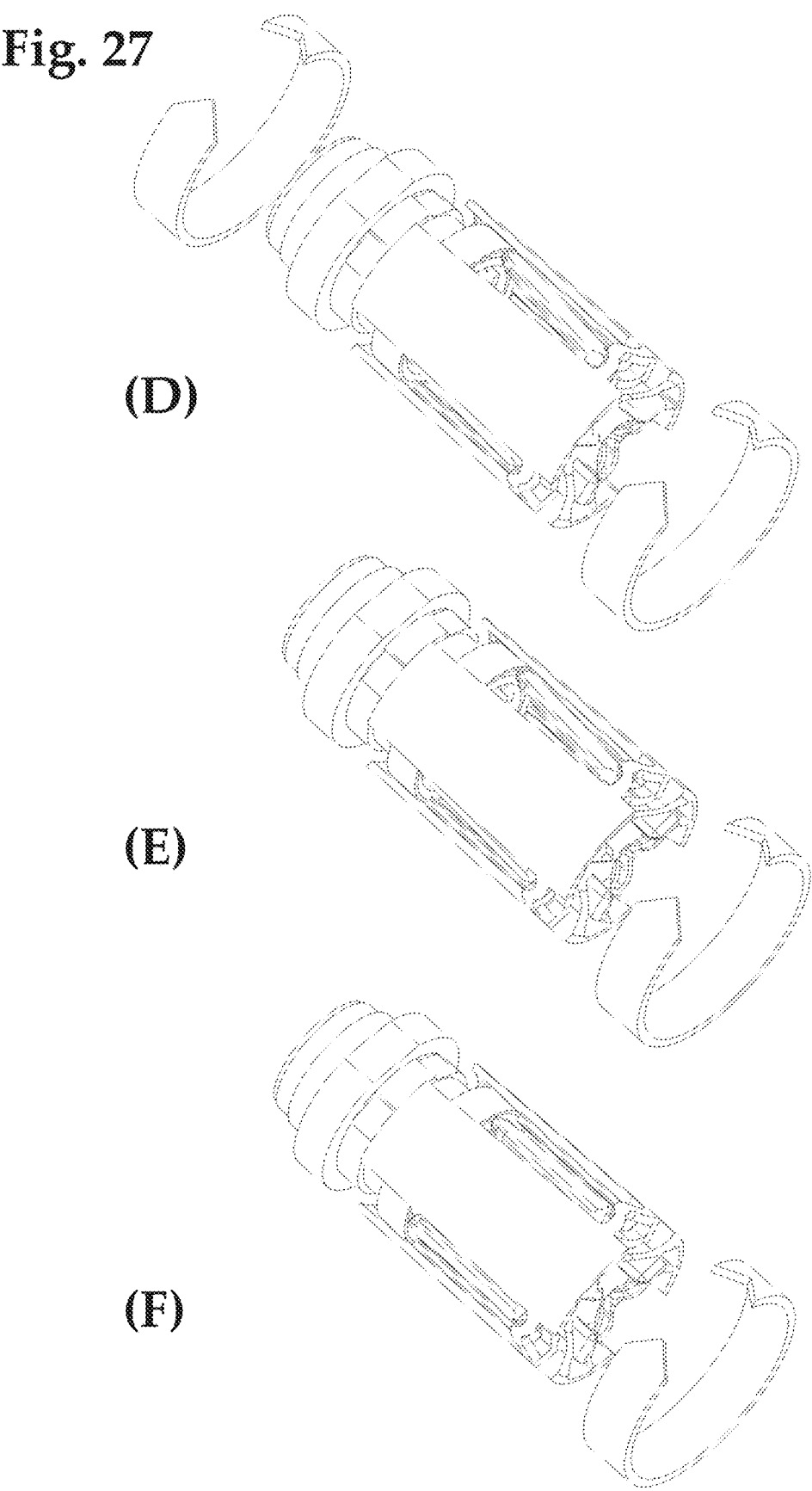
Figure 27:
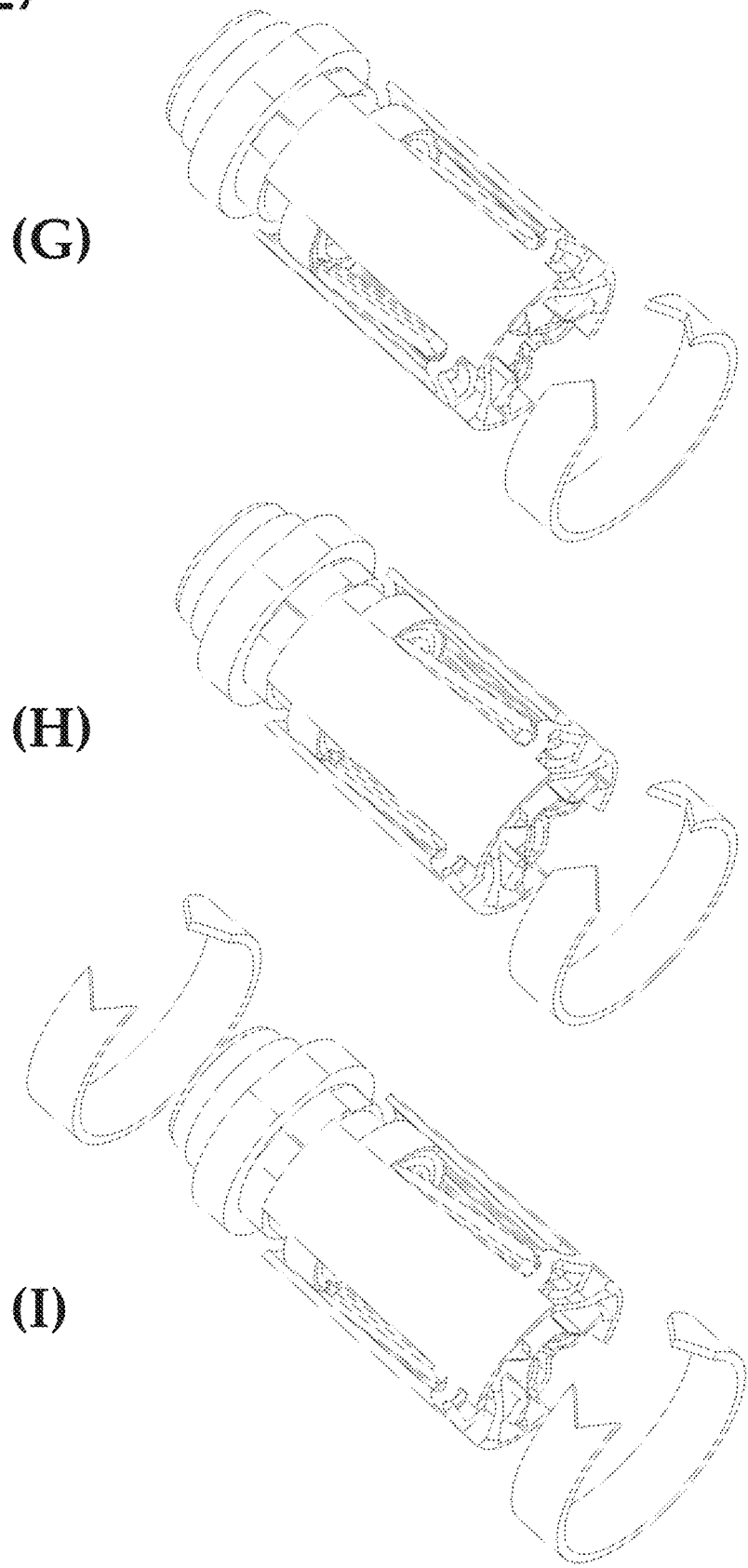
Figure 27:
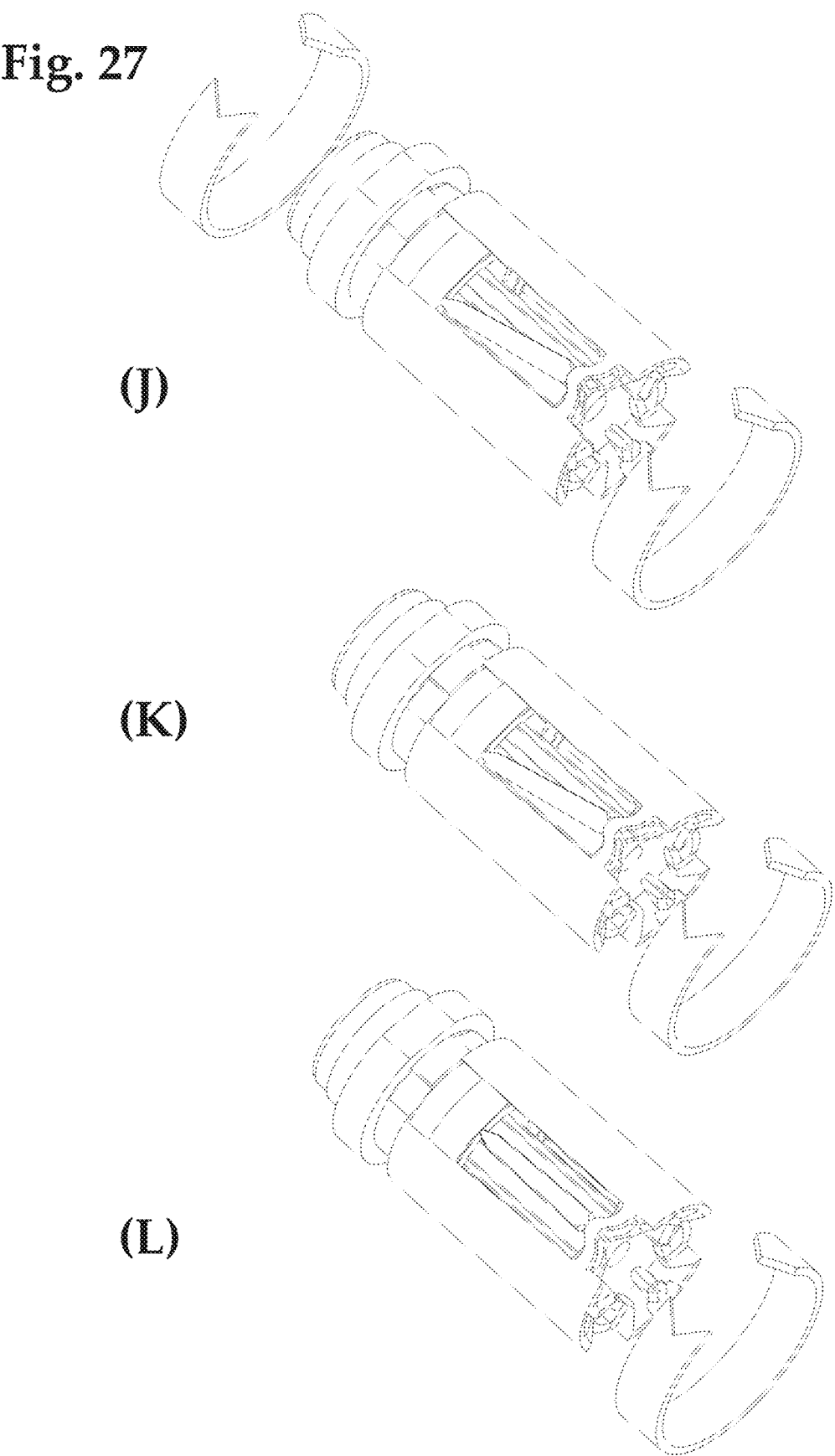

In at least one embodiment of a dosing unit is depicted in FIGS. 5 and 26, where the embodiment has a radial bias force element 5. Here the spring element 52 is a metal spring having the basic shape of an open ring, with two locking structures 53 at the two ends of the open ring, and a straight segment 56 in the middle. When mounted to the cylinder, the locking structures 53 are located in corresponding recessions. The straight segment 56 is located in an opening 221 of the cylinder wall, through which the flat portion 56 abuts the thread 33 of the plunger shaft 32. The two arms of the spring element 52 between the locking structures 53 and the central flat portion 56 remain slightly deformed when mounted to the cylinder, providing a constant radial bias force $F_{bias}$.

In at least one embodiment plunger shaft 32 has been provided with a continuous outer thread, while the inner thread has been reduced to a single segment (FIG. 2) or two segments (FIG. 5). Such a configuration may be advantageous in regard to reproducibility of thread lash reduction (see also discussion of FIGS. 2 and 3). Alternatively it is also possible to provide the shaft 32 with a single outer thread segment 22, and the inner surface of the cylinder with a continuous inner thread 23, as for example shown in FIG. 6. The distal end of the plunger shaft 32 is split into two shaft arms 321, 321'. On one shaft arm 321 a single outer thread segment 33 is arranged, interacting with the inner thread 23 of the cylinder. On the other shaft arm 321' of the plunger shaft, a flat cylinder segment 56 is arranged, abutting the surface of the inner thread 23. A spring element 52 in the form of a single metal leaf spring is arranged between the two shaft arms 321, 321', providing a radial force directed outwards. As a result the outer thread segment 23 is constantly biased against the inner thread 23, thereby removing the thread lash. The two shaft arms 321, 321' of the plunger as such are not biased, since the corresponding force is provided by the spring element 52. Thus such an embodiment does not suffer from creep deformation as in the state of the art.

Figure 7:
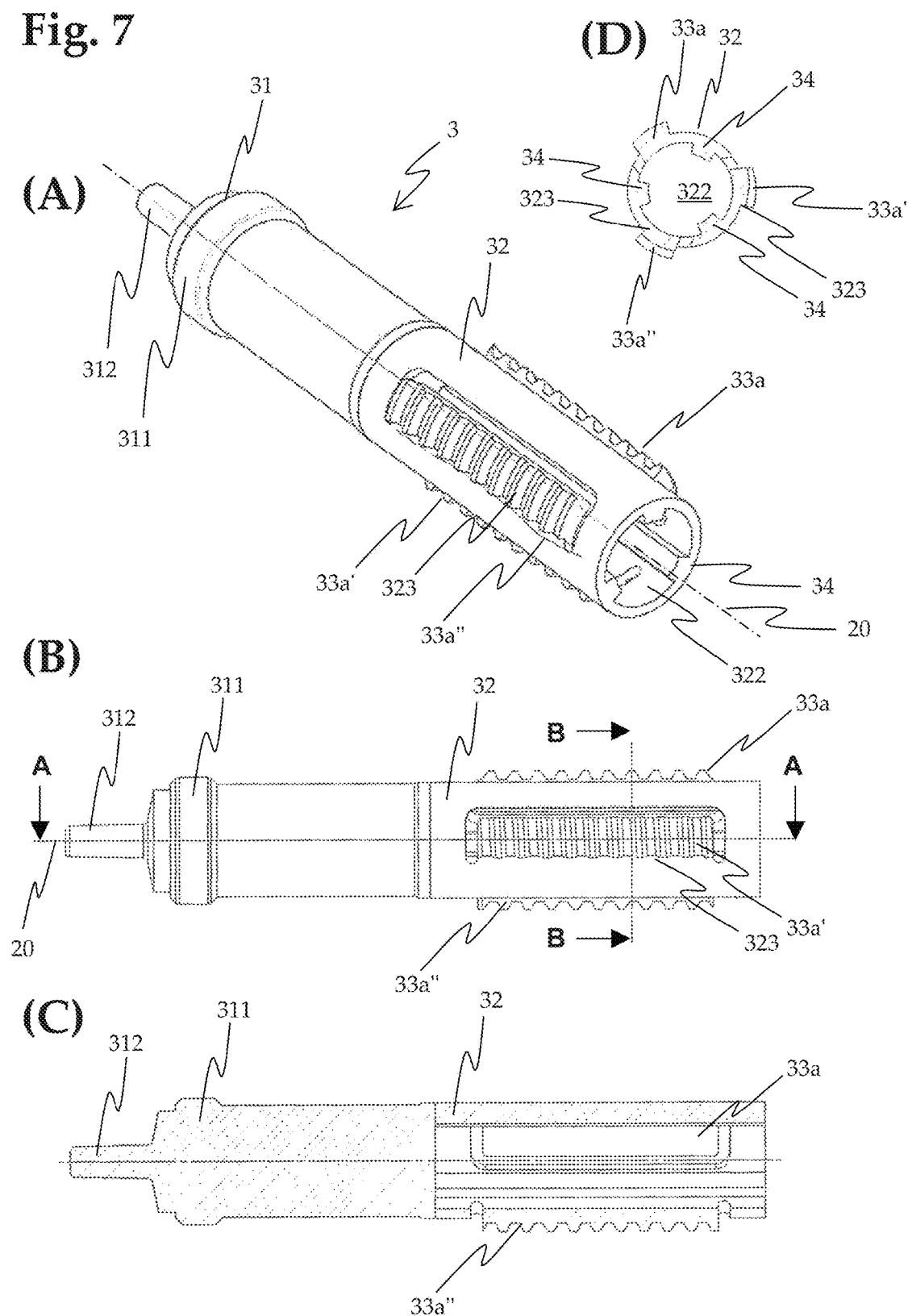
FIG. 7 depicts at least one embodiment of a plunger according to the present disclosure with thread lash reduction, having three pivotably mounted thread portions, (A) in a perspective view, (B) in a longitudinal view, (C) in a longitudinal section along plane A-A, and (D) in a cross-section along plane B-B.

At least one additional embodiment of a plunger with thread lash reduction is given in FIG. 7. The outer thread 33 of the plunger shaft is divided into three rectangular portions 33a, 33a', 33a'', equally distributed on the shaft 32. The threads are provided such that the outer thread is stably arranged and runs smoothly in a continuous inner thread of the cylinder. The thread portions are arranged in corresponding rectangular openings on the shaft, connected to the shaft only by a longitudinal hinge structure 323, e.g. a film hinge or a longitudinal area with reduced wall thickness. The thread portions thus are pivotable along the axis of said hinges, about a small angle. The three outer thread portions are radially biased toward the inner thread, thereby efficiently removing thread lash.

The necessary bias force can be obtained by one or more suitable spring elements, e.g. a slotted metal ring spring (not shown) arranged in a circular groove in the bore 322 of the shaft. A suitable way to manufacture such a plunger is insert injection moulding, where the ring spring is over-moulded with the thermoplastic polymer material of the plunger shaft.

In at least one additional embodiment, the dimensions of the shaft are chosen such that the pivotably mounted thread portions are slightly compressed inwards when introduced into the inner thread. In that case the spring force is generated by the shaft/thread structure itself.

At least one approach is shown in FIG. 8, where a plunger 3 having a shaft 32 with continuous outer thread 33 is arranged in a threaded sleeve 26 with four threaded claws 25, 25', 25'', 25''', separated by slots 251. In the given embodiment a slotted tension ring 27 is arranged as a radial bias force element 5 around the distal end of the claws 26, Said tension ring is dimensioned such that the claws are slightly biased inwards, toward the outer thread 33 of the plunger shaft, the inner and outer thread thereby engaging without thread lash.

Figure 9:
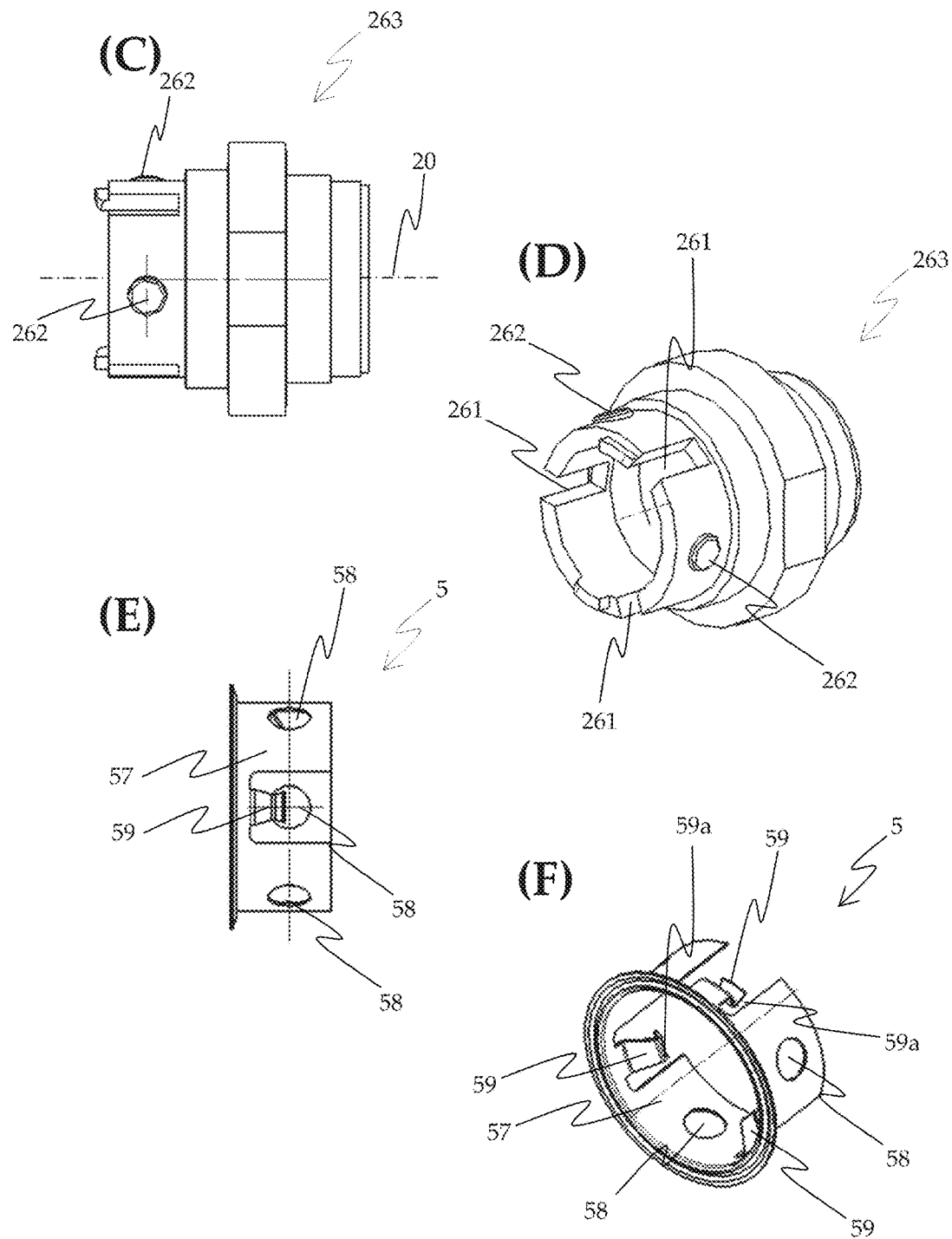
FIG. 9 schematically depicts at least one embodiment of a dosing unit with thread lash reduction arrangement, in which three biased spring elements act as an radially biased outer thread, with the dosing unit (A) in a perspective view, and (B) in a detail view of a longitudinal section, with a distal sleeve (C) in a longitudinal view, and (D) in a perspective view, and with an axial bias force element with three radially biased spring elements (E) in a longitudinal view, and (F) in a perspective view.

At least one embodiment of a thread lash reducing arrangement with radial bias force is shown in FIG. 9. A sleeve element 263 is mounted to the distal end of the cylinder 2. A radial bias force is provided by radial bias force element 5 with three spring biased inner thread segments 59a. The radial bias force element is mounted to the distal end of the sleeve element 263, and comprises a mounting sleeve 57 with three openings 58, and three spring elements 59. Together the sleeve element 263 and the radial bias force element 5 form a threaded sleeve 26, the inner thread segments acting as the inner thread 23 of the threaded sleeve.

Assembling the threaded sleeve 26, the mounting sleeve 57 is put over the sleeve element 263, such that three protrusions 262 lock into the openings 58, thereby positively locking the mounting sleeve 57 on the sleeve element 263. The three spring elements 59 are located in three longitudinal slots 261 of the sleeve element 263.

Sleeve element 263 and bias force element 5 are designed such that the thread segments 59a of the three spring elements 59 engage with the outer thread 33 of a plunger shaft 32 that is engaged with the threaded sleeve 26. The thread segments 59a thus act as short thread segments 23 of the threaded sleeve 26. In the assembled state, the thread segments 59a are radially biased, with a spring force $F_{bias}$ acting radially inwards. The three spring elements are symmetrically arranged around the longitudinal axis. As a result the radial force components acting on the plunger shaft sum to zero.

The flanks of the thread segments 59a of the spring elements 59 of the radial bias force element 5 abut the flanks of the plunger shaft thread 33. Thread lash is removed, similar to FIG. 2, as long as the relation $F_{bias,min}=\cot(\alpha)F_{ax}$ applies for the minimum radial bias force $F_{bias,min}$ and the external axial force $F_{ax}$.

In at least one embodiment, a similar radial bias force element 5 is mounted to the plunger shaft, its spring biased outer thread segments 59b acting as the outer thread 33 of the plunger shaft, engaging with the inner thread 23 of the cylinder without thread lash.

Figure 10:
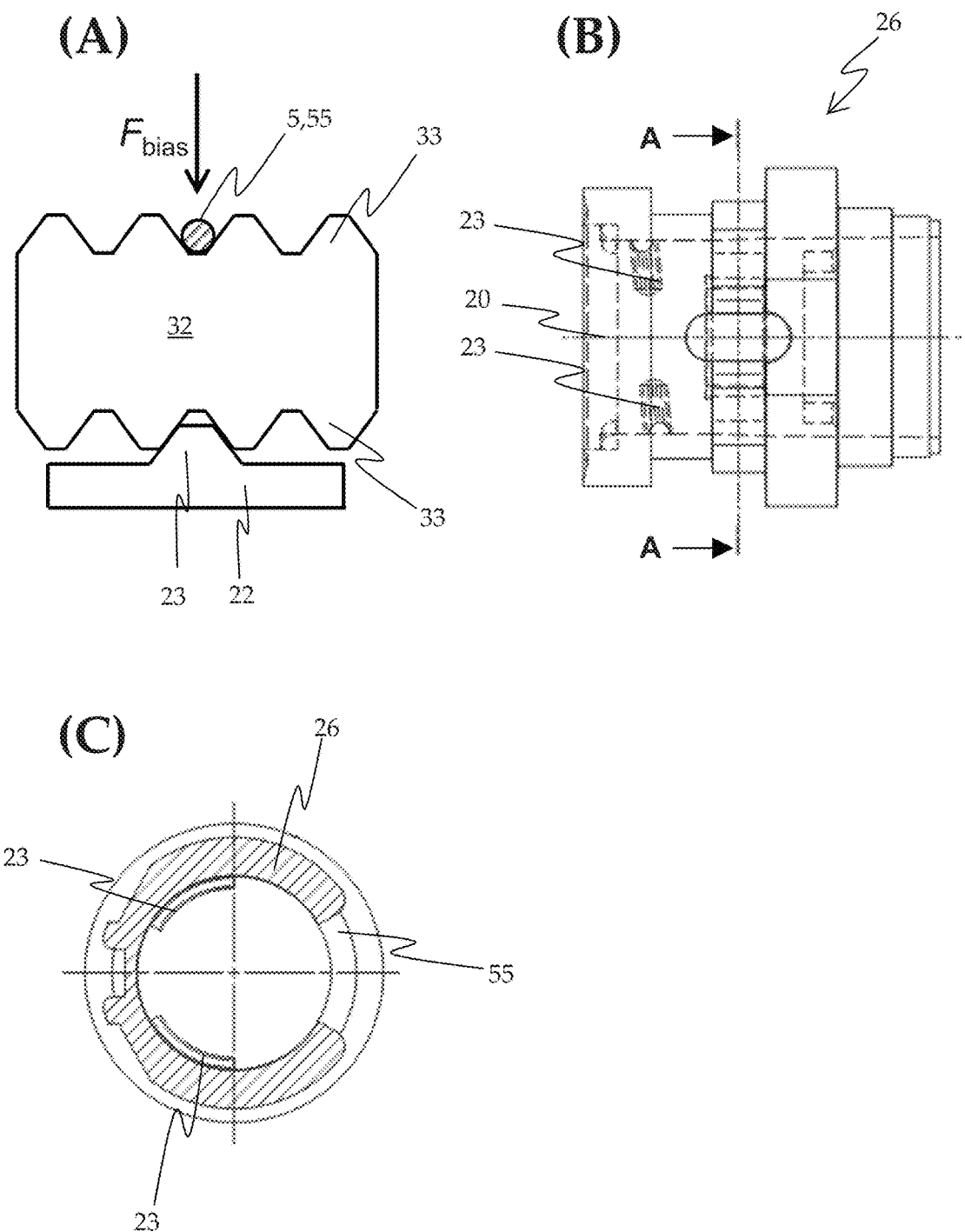
FIG. 10 shows at least one embodiment of a thread lash reduction arrangement according to the present disclosure, in which a biased wire is used as a radial bias force element. The interaction of the biased wire, the threaded plunger shaft, and the thread portion on the cylinder surface is schematically depicted in (A). A distal portion of the cylinder is shown in (B), and a cross-section along plane A-A in (C).

In at least one embodiment of a thread lash reduction arrangement is depicted in FIG. 10. In contrast to the embodiment shown in FIG. 3(a), where a radially biased inner thread segment provides the radial bias force, a short wire segment 55 is used as the radial bias force element 5.

The wire segment 55 is mounted on a threaded sleeve, parallel to the other threads 33 of the plunger. Two inner thread segments 23 are arranged on the sleeve 26 opposite to the wire 55. During operation the bias wire 55 is arranged in a groove of the outer thread 33. The wire is attached on its two ends to the sleeve in such a way that it is strained when the plunger shaft thread 33 is introduced into the threaded sleeve 26. The strained wire exerts a radial bias force on the plunger shaft, resulting in a radial bias force between outer thread 33 and thread segments 23. In the embodiment as shown in FIG. 10(a), the wire abuts the groove of the thread 33.

In at least one embodiment discussed so far the bias force providing the thread lash free engagement of plunger thread and cylinder thread was directed radially. Inner thread and outer thread were subject to a force perpendicular to the longitudinal axis.

In at least one embodiment of the present disclosure, the bias force is directed axially, along the longitudinal axis 20, as for example in FIG. 11. A continuously threaded 33 plunger shaft 32 is arranged in a threaded sleeve 26 at the distal end of a cylinder. A separate threaded element 64 with an inner thread 65 is coaxially mounted behind the threaded sleeve 26, connected to the latter via a helical spring 62.

Together the threaded element 64 and the helical spring 62 act as a spring biased axial bias force element 6. The helical spring 62, arranged coaxially to the plunger 32, provides an axial force $F_{bias}$, pushing the threaded element 64 away from the threaded sleeve 26 along the longitudinal axis 20. As a result, during normal operation the distal flanks of the threaded portion 65 of the threaded element 64 abut the proximal flanks of the plunger shaft thread 33, and the proximal flanks of the static threaded sleeve 26 abut the distal flanks of the plunger shaft thread. Independently from any reversal of the rotation direction of the plunger, or any external axial force due to a pressure differential in the metering chamber, the plunger 3 will be positively locked in the cylinder thread, without thread lash.

In at least one embodiment, the roles of the inner 23 and outer 33 threads are exchanged, as shown in FIG. 11(c). A threaded sleeve 26 comprises a continuous inner thread 23. A plunger shaft 32 is provided with an outer thread 33. A threaded element 64' with an outer thread 66 is shiftably arranged on the plunger shaft 32. A spring element in the form of a helical spring 62 is coaxially arranged between the end of the outer thread portion 33 and the threaded element 64'. Together the threaded element 64' and the helical spring 62 form a spring biased axial bias force element 6. The helical spring 62 provides an axial force $F_{bias}$, pushing the threaded sleeve 64' away from the outer thread portion 33 along the longitudinal axis 20. As a result, during normal operation the proximal flanks of the outer thread portion 66 of the threaded element 64' abut the distal flanks of the cylinder thread 23, and the distal flanks of the outer thread 33 abut the proximal flanks of the cylinder thread 23. Independently from any reversal of the rotation direction of the plunger, or any external axial force, the plunger 3 will be positively locked in the cylinder thread 23, without thread lash.

In the dosing unit as known from prior art EP 2163273 A1, the friction force between cylinder valve member and plunger, which is necessary for reliably switching the valve before the plunger is linearly displaced, is constant. As a result the corresponding rotational torque that is necessary for actuating the plunger is also constant.

Figure 12:
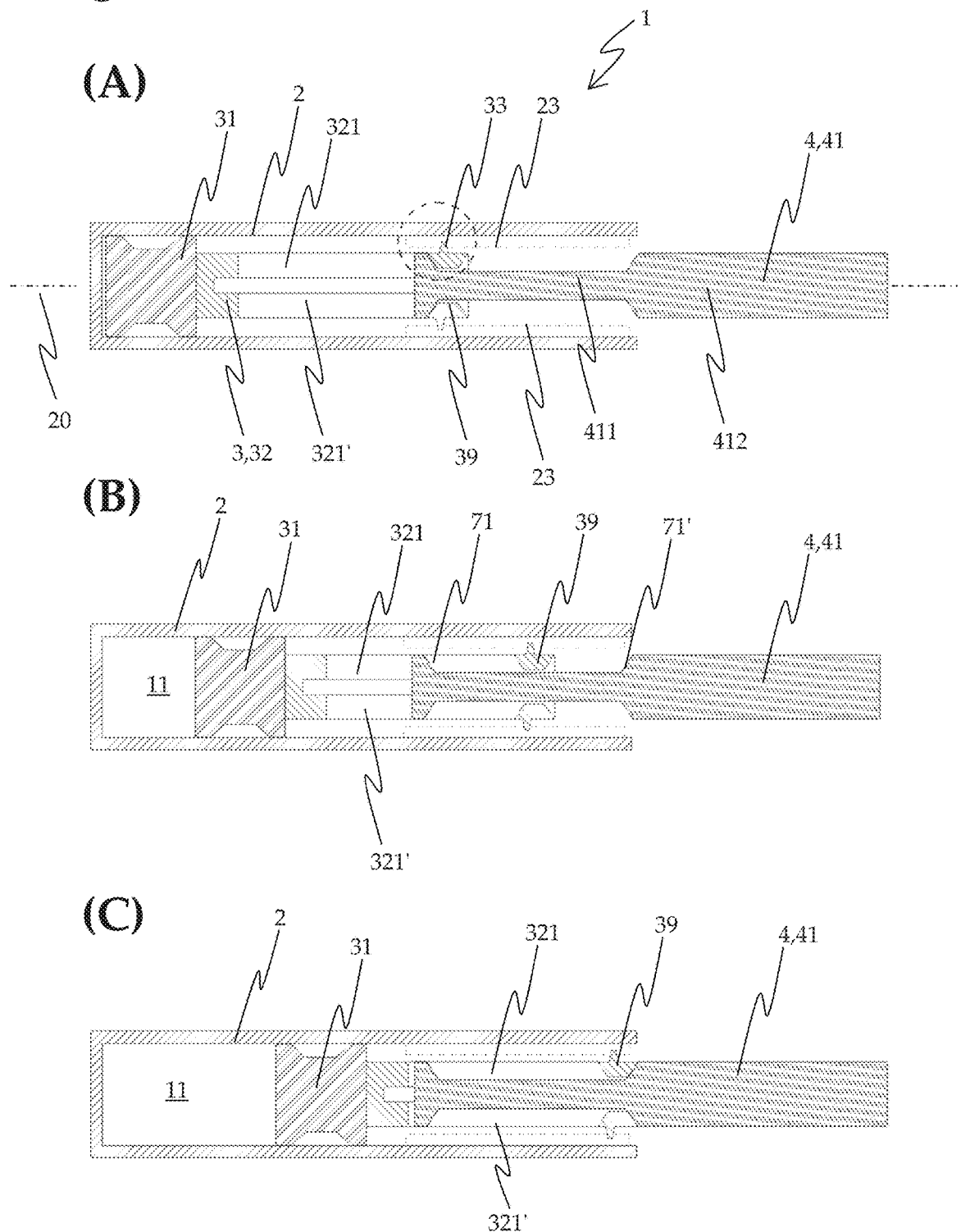
FIG. 12 schematically shows a longitudinal section of at least one embodiment of a dosing unit with controlled friction between plunger and cylinder, (A) with the plunger in a start position, (B) with the plunger in a medium position, and (C) with the plunger in a maximum position. A detail of FIG. 12(A) is shown in (D), explaining how the driving rod controls the friction between plunger and cylinder.

To reduce energy consumption of the drive unit actuating the plunger, the friction force between cylinder valve element and plunger during linear plunger displacement may be reduced, where the valve is in one of its operational states. At least one embodiment of a dosing unit that allows controlling the friction between cylinder valve member 2 and plunger 3 is shown in FIGS. 12, 13, and 14. The valve seat of the dosing unit 1 is not shown for simplicity. The threads 33, 23 are only schematically indicated. The plunger 3 is coaxially arranged in the cylinder valve member 2, defining a metering cavity 11. The plunger 3 comprises a plunger plug 31 and a plunger shaft 32. Said plunger shaft is longitudinally split into two shaft arms 321, 321', pivotably connected to the plunger plug 31 by a hinge region 323. A coupler element 4, releasably coupled to a drive unit (not shown) of an infusion pump device, has a driving rod 41, essentially comprising a distal part stem 412, to be connected to the drive unit, and a proximal part 411 that is arranged in a longitudinal bore 322 of the plunger shaft. The proximal part 411 comprises two cams 43, 43', slidably arranged in the slot 37 that divides the shaft 32 into the two shaft arms 321, 321'. Rotational torque is primarily transferred from the driving rod 41 to the plunger shaft 32 via said cams 43, 43'. Two other cams 44, 44' are arranged perpendicular to the first cams 43, 43', each having a long cut-out 441 that leaves a proximal ramp 71 and a distal ramp 71'.

Along each of the two shaft arms 321, 321' a longitudinal slot 38 is arranged, on the proximal side limited by the hinge region 323 of the shaft 32, and on the other side by a bridge structure 39 bearing an outer thread element 33a, 33a'. The two bridge structures 39 comprise a proximal ramp 72 and a distal ramp 72'. When assembled the bridge structures are arranged in the cut-out 441 of the coupling rid 41, between the two ramps 71, 71'. During operation the linear orientation of the driving rod 41 in regard to the cylinder valve member 2, as well as the rotational orientation of the driving rod 41 in regard to the plunger 3, remain constant.

As will be shown, the elements of the plunger shaft 32 and the driving rod 41 engage in such a way that friction between plunger and cylinder valve element is increased to a high value when the plunger shaft and the driving rod are in certain positions to each other, thereby frictionally coupling cylinder and plunger. In the other positions friction is on a lower level. This functional principle is explained in more detail in FIG. 12, and Table 1.

TABLE 1

| Plunger rotation direction | Valve State | Metering cavity | Frictional coupling between Cylinder valve member and plunger | Figure |
|---|---|---|---|---|
| Pump direction | Pump state | Partially filled | None | 12(b) |
| Pump direction | Pump state | Empty | Yes | 12(a) |

TABLE 1-continued

| Plunger rotation direction | Valve State | Metering cavity | Frictional coupling between Cylinder valve member and plunger | Figure |
|---|---|---|---|---|
| Refill direction | Undefined, valve rotates until the other stopper is reached. | Empty | Yes | 12(a) |
| Refill direction | Refill state | Partially filled | None | 12(b) |
| Refill direction | Refill state | Maximum capacity | Yes | 12(c) |
| Pump direction | Undefined, valve rotates until the other stopper is reached. | Maximum capacity | Yes | 12(a) |
| Pump direction | Pump state | Partially filled | None | 12(b) |

Assuming that the valve of the dosing unit is in the pump state, the valve member abutting a corresponding stopper of the valve seat, and the outlet being connected to an infusion set, and that the metering cavity is partially filled (see the situation in FIG. 12(b)), the drive unit will rotate the plunger such that it is linearly shifted to the left, thereby conveying liquid medicament toward the infusion set. The friction between plunger 3 and cylinder 2, namely thread friction and friction between plunger plug and cylinder wall, is chosen such that is as small as possible, in order to minimize energy consumption of the drive.

When the plunger reaches the cylinder head, and the metering cavity is completely emptied (see FIG. 12(a)), the proximal ramp 72 of the bridge structure 39 of the plunger shaft 32, shifting to the left, engages with the proximal ramp 71 of the driving rod 41 and forces the bridge structure 39 radially outward toward the cylinder wall. As a result the thread segment 33a on the bridge structure is radially pressed onto the inner thread 23, which increases thread friction until finally the outer thread is jammed in the inner thread.

To continue the administration of liquid medicament it will be necessary to retrieve new liquid medicament from the primary reservoir of the infusion pump. For that the valve has to be switched from the pump state to the refill state, which requires a reversal of the rotation direction of the plunger and a frictional coupling between cylinder valve member and plunger. Since the inner and outer threads are jammed, friction between cylinder and plunger is considerably larger than friction between cylinder and valve seat. The rotating plunger grips and rotates the cylinder in the valve seat until it reaches the stopper that defines the valve's refill state, where the inlet conduit is connected to the primary reservoir. Since cylinder rotation is now mechanically blocked, the drive unit can overcome the thread jamming. The proximal ramp 72 of the bridge structure 39, now shifting to the right, disengages from the proximal ramp 71 of the driving rod, until thread friction and thus energy consumption is minimal again.

During the following refill mode, the plunger is displaced to the right and the metering cavity is refilled (see FIG. 12(b)), until finally maximum filling capacity is reached (see FIG. 12(c)). When the plunger reaches this maximum position at the right, the distal ramp 72' of the bridge structure 39 engages with the distal ramp 71' of the driving rod, forcing the bridge structure and the outer thread segment radially outwards toward the inner thread 23, until the thread is jammed. The valve has now to be switched back to the pump position, disconnecting the primary reservoir and connecting the infusion set. Since cylinder and plunger are again temporarily frictionally coupled, rotating the plunger in the reversed direction (pump direction) will rotate the cylinder in the valve seat until the stopper is reached that defines the pump state of the valve. Further rotation of the plunger disengages the ramps 71', 72' and removes the thread jam, and the plunger can be moved again to the left with minimum friction.

As can be seen, at least one embodiment of the dosing unit allows controlling the friction between plunger and cylinder valve member. The interaction between the ramps 72, 72' of the bridge structures 39 and the ramps 71, 71' of the driving rod 41 provides the possibility of temporarily radially biasing the outer thread segments toward the inner thread 23, thereby increasing thread friction. Thus a dosing unit optimizes energy consumption by restricting friction to a minimum level during pumping and refilling. Although this increase may go up to an actual temporary jamming of the thread, it is also possible just to increase friction to a value that is sufficient for the valve switching.

Figure 15:
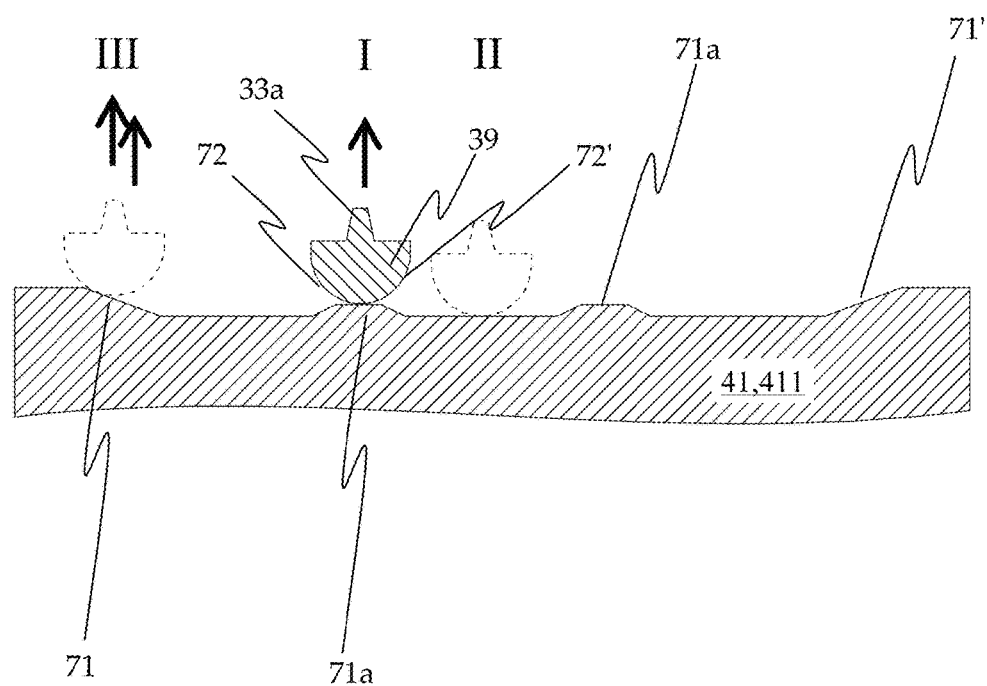
FIG. 15 schematically shows a longitudinal section of at least one embodiment of a plunger shaft and driving rod that allows valve switching in intermediate positions according to the present disclosure.

The example discussed above provides opportunities to switch the valve at two distinct positions, namely when the metering cavity is either completely empty or completely full. An advantageous variant that allows the switching of the valve also in intermediate positions is explained in FIG. 15. In addition to the two ramps 71, 71' at the proximal and distal end of the driving rod 41, two elevations 71a arranged on the driving rod between the ramps provide two other positions where bridge structures 39 and thread segments 33a, 33a' are radially biased (see position I). The height of the elevations is chosen such that although friction is increased, no jamming takes place. Thus the dosing unit may continue in the mode it currently is in, for example pumping. The only effect will be a temporary increase of energy consumption until the end of the elevation is reached, due to the temporary increase of thread friction. If on the other hand the valve should be switched at this intermediate position, the dosing unit may do so by reversing the plunger rotation and rotating the frictionally coupled cylinder in the valve seat until the stopper is reached, and frictional coupling is released. Between the elevations and/or ramps, the bridge structure is not biased (see position II). When the bridge structure reaches one of the outer ramps (see position III), the friction can be increased up to thread jamming, although this is not actually necessary.

The exemplary dosing units discussed in FIGS. 12 to 15 may also be combined with thread lash reduction. For example may the two shaft arms of the plunger shaft be pre-biased, due to radial dimensions that are slightly larger than the dimensions of the inner thread, or a radial bias force element as shown for example in the embodiments in FIG. 6 or 7 can be applied.

At least one embodiment of a dosing unit 1 with controlled friction is shown in FIG. 16, with the valve seat not shown for simplicity. The cylinder valve member comprises a cavity part 28 and a threaded sleeve part 26, mounted together. The threaded sleeve part 26 has an inner thread 23, which may be some few windings, or even only a thread segment, particularly if one of the thread-lash reduction schemes is applied that have been discussed further above.

The plunger 3 with plunger plug 31 and plunger shaft 32 is coaxially arranged in the cylinder 2. The plunger shaft 32 comprises a continuous outer thread 33, engaging with the inner thread 23 of the threaded sleeve 26. In the figure the threads are only schematically indicated for simplicity. The plunger shaft comprises a longitudinal bore 322, in which a driving rod 41 of a plunger driving part 4 is shiftably arranged.

The plunger and the cylinder are realized in such a way that friction is minimal during the pump mode and refill mode, in order to restrict energy consumption by the drive unit (not shown). In order to temporarily increase friction and thereby enabling the valve switching functionality by the drive unit, two friction cylinders 74, 74' are arranged on the proximal and the distal end of the plunger shaft 32. Said two friction cylinders may frictionally engage with two corresponding hollow friction cylinders 74a, 74a' that are arranged on the proximal and the distal side of the inner thread 23 of the threaded sleeve 26. When the plunger is in the position where the metering cavity 11 is completely empty (FIG. 16(a)) or completely filled (FIG. 16(b)), the abutting cylinder surfaces of the engaging friction cylinders cause increased friction. This provides the necessary additional friction between plunger and cylinder to reliably actuating the valve and rotating the cylinder valve member in the valve seat upon reversal of the plunger rotation direction. This can be seen in more detail in FIG. 16(c). When the spindle drive rotates the plunger toward the maximum distal position, the friction cylinder 74 continuously shifts to the right into the cavity of the hollow friction cylinder 74a, thereby linearly increasing friction. The dimensions of the interacting elements and the materials used are chosen such that latest when the plunger is in the maximum filling position, the friction between cylinder valve member and plunger, namely between the friction between the engaging friction cylinders and the constant friction due to the thread and the plunger plug, are sufficiently large to actuate the cylinder valve member in the valve seat when the plunger rotation direction is reversed.

When the plunger rotation direction is reversed, the plunger grips the cylinder and rotates it in the valve seat, until the cylinder abuts the stopper of the valve set. The static friction force is overcome, and the plunger starts again to rotate and to displace in the cylinder. The overlapping area of the friction cylinders, and thus the additional friction force, decreases linearly to zero.

As in the example discussed before, the friction between cylinder and plunger is mechanically controlled, depending on the relative position of the plunger in the cylinder. However, the element controlling the additional friction (the hollow friction cylinders 74a, 74a') are in this case located on the cylinder, while in FIG. 12 the cams as the controlling element are located on the driving rod. In both cases the relative position of the linearly static elements (cylinder and driving rod) in regard to the displaceable element (the plunger) is the parameter used to control the amount of friction between plunger and cylinder.

Figure 17:
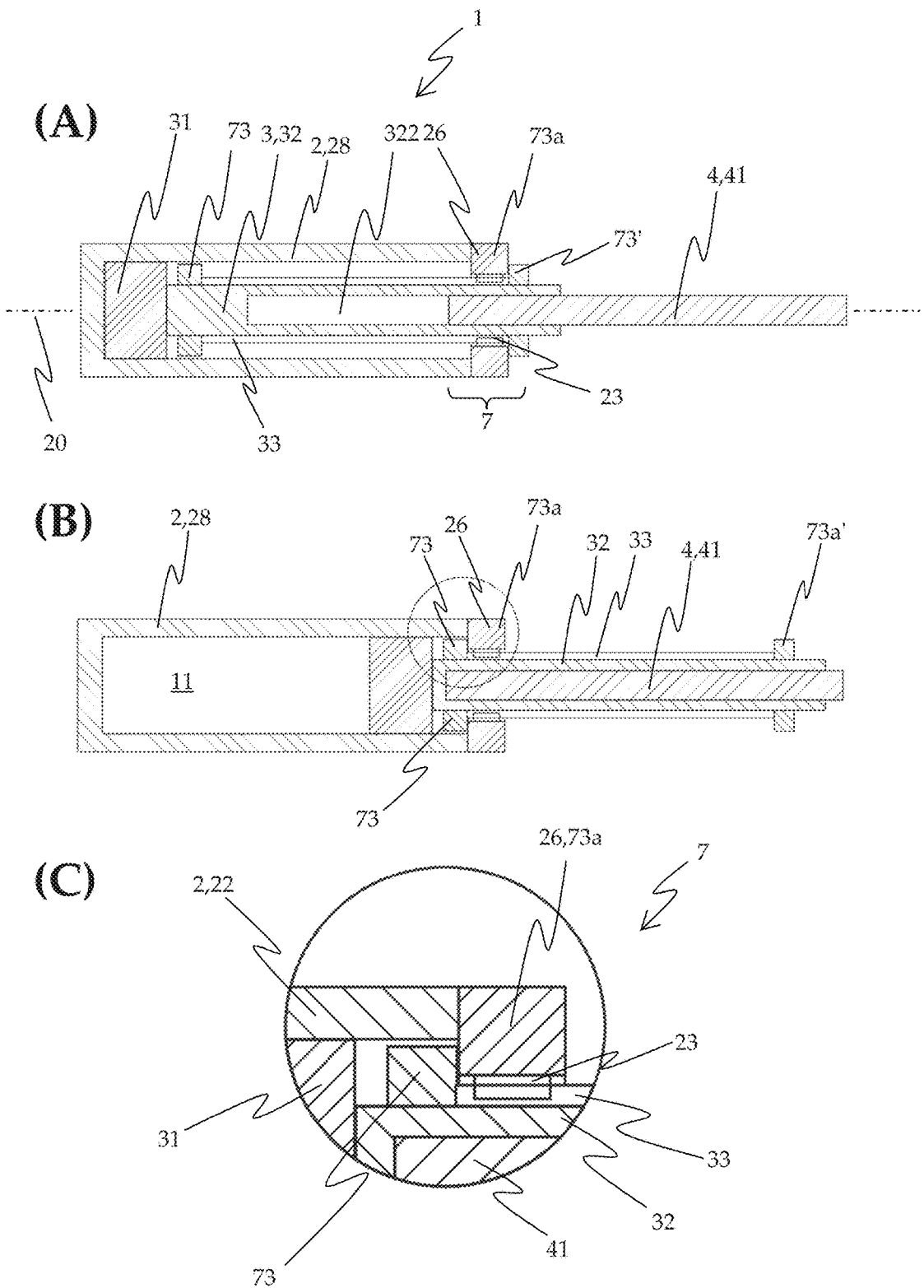
FIG. 17 schematically shows at least one embodiment of a dosing unit with controlled friction between plunger and cylinder, (A) with the plunger in a start position, and (B) with the plunger in a maximum position. A detail of FIG. 17(A) is shown in (C), explaining how the driving rod controls the friction between plunger and cylinder.

At least one embodiment of dosing unit 1, using a similar principle for controlling the friction, is described in FIG. 17. Again the valve seat is not shown for simplicity. Two stopper disks 73, 73' are mounted on the plunger shaft 32, on a proximal and a distal end of the continuous outer thread 33. The threaded sleeve 26 comprising the inner thread 23 is also realized as a stopper disk 73a.

The additional friction that is necessary for switching the valve in the end positions of the plunger is generated when one of the two stopper disks, e.g. the proximal stopper disk 73 as shown in FIGS. 17(a) and (c), abuts the stopper disk 73a mounted to the cylinder. Since the plunger is actually mechanically blocked from a further linear displacement, the thread friction force exponentially increases with any further rotation, immediately jamming the plunger thread 33 in the cylinder thread 23 and frictionally coupling the plunger and the cylinder. When now the plunger rotation direction is reversed, the static friction between cylinder and plunger is large enough to actuate and rotate the cylinder in the valve seat (not shown) of the dosing unit. When the cylinder abuts the stopper of the valve seat, the thread jamming is removed and frictional coupling is released. Thread friction is back to a minimum level. A dosing unit embodiment as discussed in the example above is very robust and reliable.

A further variant of such a dosing unit is shown in FIG. 18, having two stopper disks 73a, 73a' mounted in the cylinder 2, while one stopper disk 73 is mounted on the plunger shaft 32 on a distal end of the continuous outer thread 33, and located between the two other stopper disks 73a, 73a'. The inner thread 23 of the cylinder is arranged on the proximal stopper disk 73a. Similar to the example above, the spindle thread 23, 33 jams when the central stopper disk 73 reaches one of the peripheral stopper disks 73a, 73a'. The resulting frictional coupling between plunger and cylinder then allows rotating the cylinder and switching the valve when the rotation direction is reversed.

The inner thread 23 of the cylinder may also be arranged on the distal stopper disk 73a', when the outer thread 33 is arranged on the other side of the central stopper disk 73. In such a case, however, the necessary length of the plunger shaft and the driving rod, and thus the overall length of the dosing unit, is increased.

Figure 19:
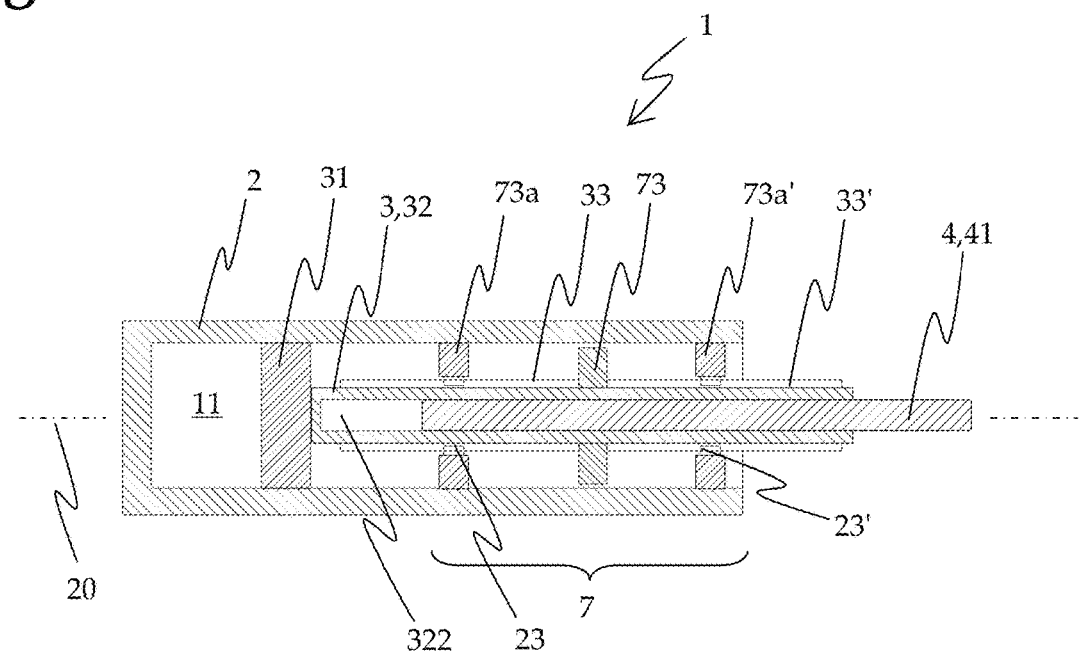
FIG. 19 schematically shows at least one embodiment of a dosing unit of the present disclosure with controlled friction between plunger and cylinder, and thread lash reduction, with the plunger in an intermediate position.

Such a dosing unit can be further modified by arranging an outer thread 33, 33' on both sides of the central stopper disk, each engaging with an inner thread 23, 23' on a stopper disk 73a, 73a', as disclosed in FIG. 19. The linear and angular orientation of the engaging threads is advantageously realized in such a way that the two thread sets longitudinally bias each other, thereby effectively removing thread lash.

Instead of achieving the temporary locking of cylinder and plunger via jamming the spindle threads, as discussed above, it is also possible to positively lock the plunger and the cylinder at certain longitudinal positions, as for example shown in the dosing unit in FIG. 20. The cylinder 2 of the depicted embodiment comprises a cylinder part 28 and a threaded sleeve 26. The valve seat of the dosing unit, in which the cylinder valve member 2 is rotatably arranged, is not shown.

An embodiment of the threaded sleeve comprises a cylinder coupling part 75 in the form of a circumferential ring with a multitude of locking holes 751. Attached to a distal end of the plunger shaft 32, a plunger coupling part 76 is provided, having locking elements 761, 761' in the form of spring biased balls, arranged on both sides of the cylinder locking element 75. The plunger locking element 76 can be realized as a cylinder-like element, having a multitude of circumferentially distributed locking elements 761, 761', or as two or more arms bearing the locking elements.

During pumping and refilling the position of the cylinder coupling part with the multitude of locking holes 751 remains in a fixed position, since the cylinder remains in a fixed position. The plunger coupling part 76 rotates and linearly shifts together with the plunger 3, to which it is attached. When the plunger 3 arrives at one of its two terminal positions, the spring-biased balls of one end of the plunger locking structure start to slide and roll over the ring 75 surface, with minimum friction. However, when they finally arrive at their corresponding locking holes 751, the balls 761, 761' snap into the holes and positively lock the cylinder to the plunger. When now the plunger rotation direction is reversed, the plunger 3 actuates and rotates the cylinder valve member 2 in the valve seat, until the cylinder abuts the stopper of the valve seat. The valve has switched. Due to continuing rotation, the ball overcomes the spring force and slides under the ring 65, and the temporary locking of cylinder and plunger is released.

Figure 21:
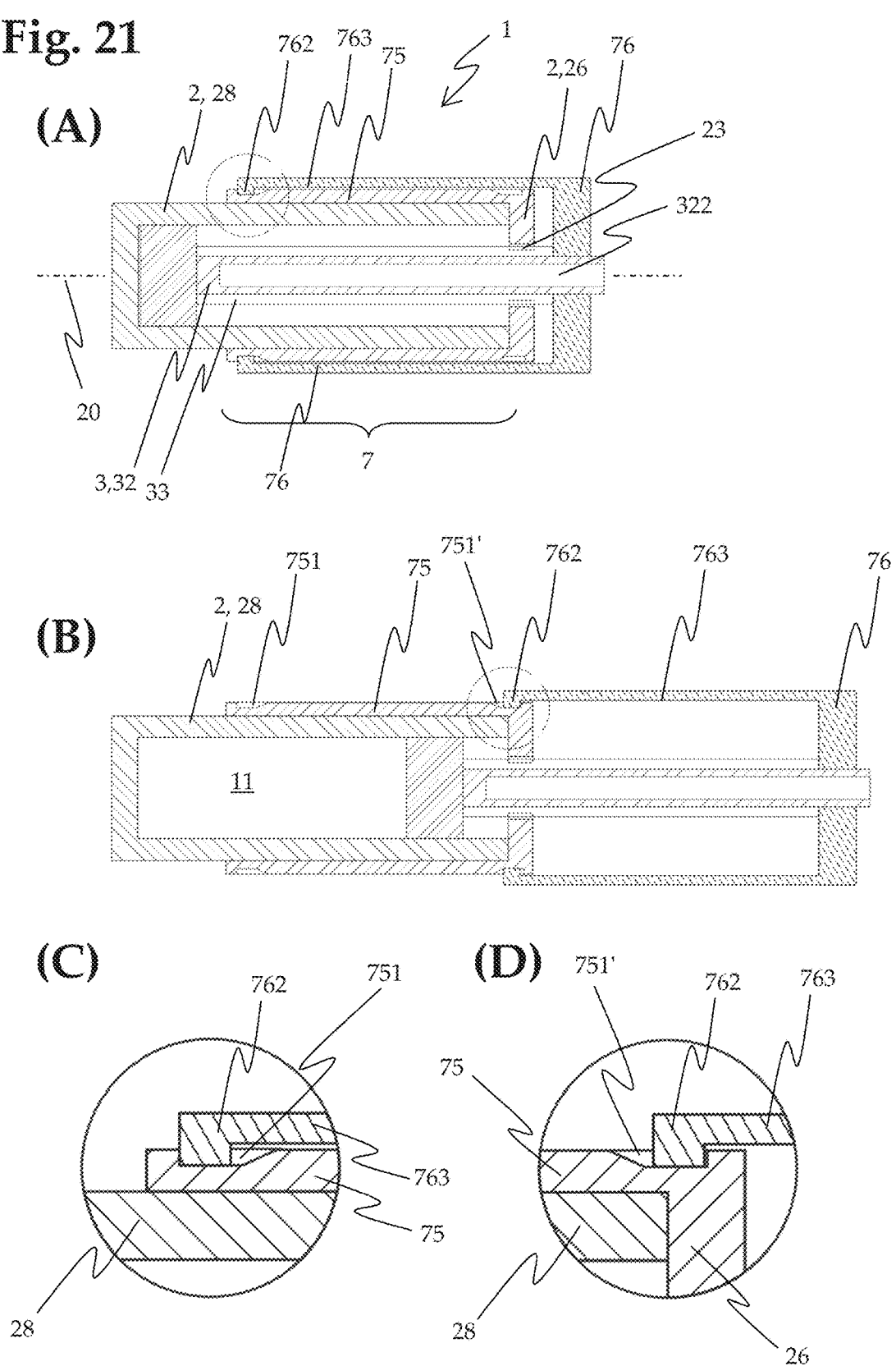
FIG. 21 schematically depicts at least one embodiment of a dosing unit of the present disclosure: (A) in a longitudinal section with the plunger in a start position, (B) in a longitudinal section perpendicular with the plunger in a maximum position, (C) in a detail view of (A), and (D) in a detail view of (B).

FIG. 21 discloses another advantageous variant of a dosing unit 1, in which a cylinder coupling part in the form of a cylindrical sleeve 75 is coaxially arranged on the cylinder part 28 and attached to the threaded sleeve 26. Alternatively said cylinder coupling part may also be realized as an integral part of the cylinder 28, or as a separate part. A plunger locking structure 76 that is attached to a distal end of the plunger shaft 32 comprises cams 762 that are pivotably mounted on the locking structure 76, by pivot arms 763. Two sets of depressions 751, 751' are located on a proximal and a distal end of the cylinder coupling part 75. The two coupling parts 75, 76 are realized in such a way that the cams 762 slide on the surface of the cylinder coupling part 75 when the cams are located between the two depressions 751, 751', and snap into the depressions when the plunger arrives at a terminal position, corresponding to an empty metering cavity 11 (FIG. 21(*a*)) or a completely filled metering cavity (FIG. 21(*b*)). The cams are radially biased inwards, since the pivot arms 763 are deformed outwards when the cams slide on the surface during operation.

The depressions 751, 751' are formed such that a perpendicular wall on the outer side (toward the end of the dosing unit) provides a clearly defined stopping position for the cam 762, thereby mechanically blocking the further linear displacement of the cam and the attached plunger, which as a results leads to a thread jam. Plunger and cylinder are now coupled by static friction. Upon reversal of the plunger rotation direction, the plunger rotates the cylinder and switches the valve. When the valve has been switched and the further rotation of the cylinder valve member is blocked by a stopper of the valve seat, the thread jam is released, and plunger and cylinder are decoupled. An embodiment of the ramp, on the opposite side of the stopper wall of the depression, forces the pivotably mounted cam outwards, until it slides on the surface. The plunger can now move to the other terminal position, with minimal friction.

Figure 22:
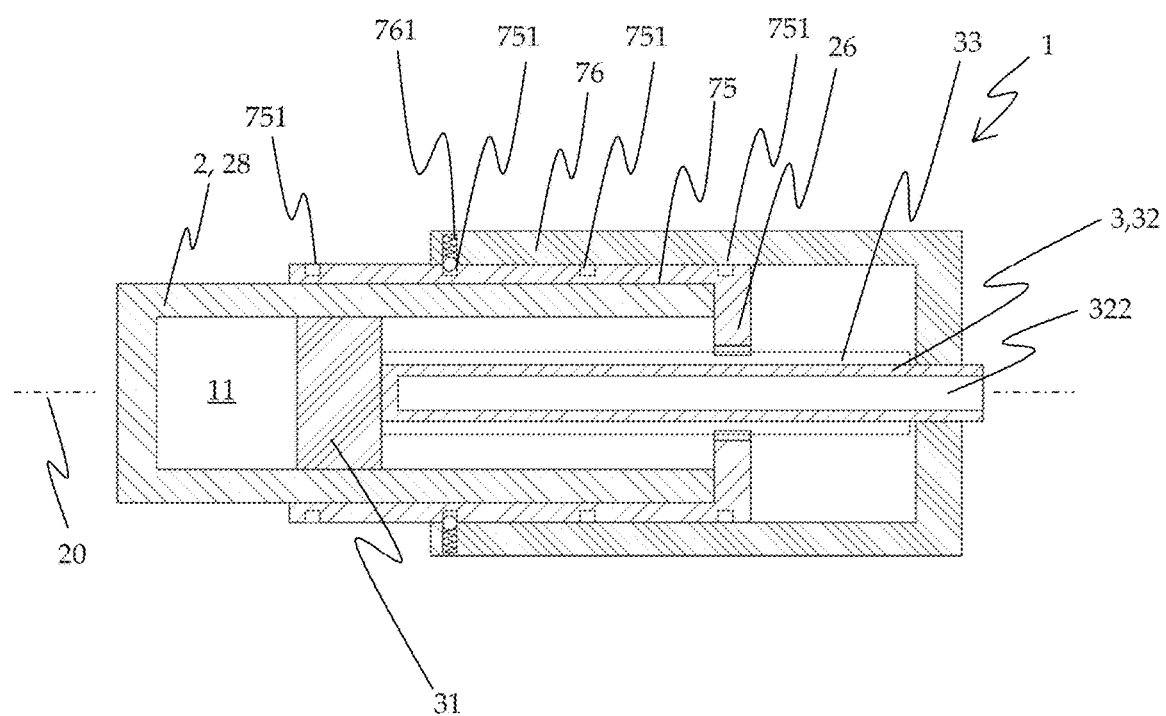
FIG. 22 schematically depicts a longitudinal section of at least one embodiment of a dosing unit of the present disclosure with the plunger in the start position, in which the cylinder can be releasably positively locked to the plunger at certain longitudinal positions.

At least one embodiment of a dosing unit is given in FIG. 22, where the pivotably mounted cam is replaced by a spring-biased ball as the locking element 761, mounted on the plunger locking structure 76. A number of locking holes 751 are distributed on the cylinder coupling part 75 in the form of a sleeve attached to the threaded part 26 of the cylinder.

During normal operation, in the pump mode or the refill mode, the plunger is linearly displaced along the axis, at the same time rotating about the axis. The spring-biased ball rolls and slides on the surface of the sleeve 75, providing minimum friction. At certain positions, the spring ball 761 snaps into a locking hole 751, positively locking plunger and cylinder. However, since the valve is in a switched state, the cylinder being mechanically blocked from further rotation, the ball is immediately forced out of the hole upon further rotation of the plunger, and rolls and slides on the surface of the sleeve 75, providing minimum friction.

If on the other hand in such a position the rotation direction is reversed, the positive locking of cylinder and plunger is strong enough to rotate the cylinder valve member in the valve seat, until the other stopper is reached and further cylinder rotation is mechanically blocked. Again the ball is forced out of the hole upon further rotation of the plunger, and rolls and slides on the surface of the sleeve.

At least one advantage of such an embodiment is the possibility to define intermediate positions on which the friction between plunger and cylinder is increased, and the valve can be switched. At these positions of positive locking, the drive unit may or may not reverse the plunger rotation direction and thereby switching the valve.

In the embodiments of dosing units discussed so far the friction between plunger and cylinder valve member is may be controlled based on the linear position of the plunger. Thus valve switching is enabled at certain relative linear positions of the plunger within the cylinder.

At least one embodiment of a dosing unit achieves cylinder valve member actuation by temporary frictional coupling between the cylinder and the driving rod, upon each reversal of the rotation direction of the driving rod. The coupling friction is not controlled by the position of the plunger in the cylinder, but by the change of the driving rod rotation direction and the relative angular orientation of cylinder and static valve seat. Such an embodiment may allow switching the valve at any longitudinal position of the plunger.

An example of such an embodiment is given by the dosing unit schematically disclosed in FIG. 23. As can be seen in the schematic cross-section, a cylindrically shaped driving rod coupling part 77 is arranged coaxially to a cylindrically shaped cylinder coupling part 79. The driving rod coupling part 77 is attached to the driving rod (not shown) of the dosing unit, while the cylinder coupling part 79 is attached to the cylinder of the dosing unit (not shown). Thus during operation of the dosing unit, the two coupling parts 79, 77 rotate in regard to each other, while at the same time being fixed in regard to each other in the longitudinal direction.

The coupling parts 79, 77 are coupled to each other by three friction elements 770 attached to the driving rod coupling part 77, symmetrically distributed along its circumference. The friction elements 770 have an O-like cross-section and are made from a flexible, elastic material. The materials of the friction elements 770 and the cylinder coupling elements 79 are advantageously chosen such that they provide a large static friction force.

The functional principle of the disclosed embodiment is that during normal operation of the dosing unit, where the plunger is either advanced or retreated within the cylinder, the inner driving rod coupling part 77 (attached to the rotating driving rod) rotates counter-clockwise in regard to the cylinder coupling part 79 (attached to the cylinder valve member), as shown in FIGS. 23(*a*) and (*b*). The cylinder valve member is mechanically blocked from counter-clockwise rotation in the static valve seat, which is schematically shown by a cam 29 of the cylinder abutting a stopper 123 of the valve seat. The elastic friction elements 770 are deformed and are dragged along by the inner coupling part 77, sliding on the inner surface 792 of the outer cylinder coupling part 79, which results in a minimum sliding friction force.

For switching the valve, the rotation direction of the driving rod is reversed to clockwise. The deformed friction elements 770 are now oriented opposite in regard to the rotation direction (FIG. 23(*c*)). The cylinder coupling part 79 is not mechanically blocked from clockwise rotation. The rotating driving rod coupling part 77 presses the friction elements into the surface 792 of the coupling part 79 and jams them in regard to the coupling part 79. The resulting static friction force between surface 792 and frictions elements 770 allows the inner coupling part 77 gripping the outer coupling part 79 and rotating it clockwise in the valve seat, until the cam 29 reaches the other stopper 123' of the valve seat, and is mechanically blocked again.

Since the cylinder coupling part cannot rotate any longer, the still frictionally coupled friction elements 770 of the inner coupling part 77 are deformed, and flip via an intermediate state (FIG. 23(d)) to an opposite conformation (FIG. 23(e)). In this conformation the friction elements again slide over the surface 792, with minimum sliding friction.

To achieve high static friction, the materials of the friction elements 770 and the surface 792 are chosen accordingly. For example may at least one of said two elements be made or covered by a rubber-like material. Furthermore the elastic friction element is realized such that the force necessary to deform and flip the friction element is larger than the force due to the torque between the inner and outer coupling parts 77, 79. To adjust the friction forces in the given setup, the different elements may be further modified. For example may the outer cylinder 79 be provided with a roughened or teethed surface. The friction elements can also be arranged on the cylinder coupling part 79 instead of the driving rod coupling part 77, or on both parts.

Figure 24:
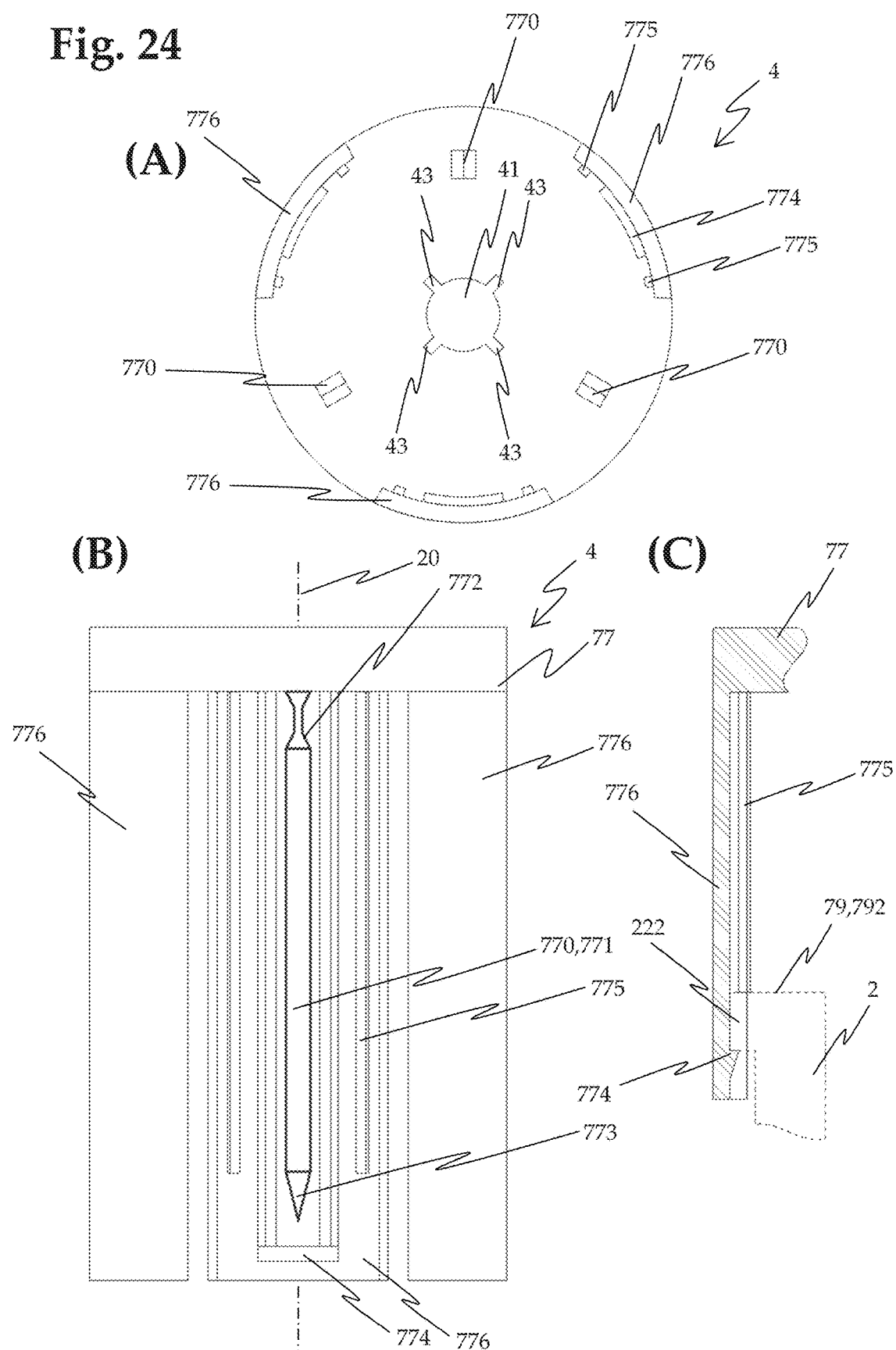
FIG. 24 schematically shows at least one embodiment of a coupling system of the present disclosure that allows switching the valve of a dosing unit at any longitudinal position of the plunger, (A) in a bottom view of the driving rod, (B) in a side view of the driving rod, and (C) in a detail of a cross-section of the coupling part of the driving rod coupled to the cylinder wall. (D) to (G) show detail views of different steps during the valve switching.

At least one embodiment of a dosing unit having dynamic friction control is disclosed in FIG. 24. Shown is the plunger driving part 4 of the dosing unit, having a driving rod 41 with four longitudinal cams 43. On a distal end of the driving rod, opposite to the end that is to be located in the longitudinal bore of a plunger shaft (not shown) of the dosing unit, a driving rod coupling part 77 is arranged, having the form of a disk. On the circumference of said disk 77, three mounting arms 776 are provided, for attaching the plunger driving part 4 to a cylinder in such a way that it is remains freely rotatable along the longitudinal axis 20. The mounting arms 776 are provided with two distance rips 775 and a cam 774.

During assembly the driving rod 41 is inserted into the plunger shaft bore. Forced by the ramp of the cam 774, the three mounting arms 776 are forced outwards, until a distal rim 222 of the cylinder wall snaps into the gap provided between the cam 774 and the two distance rips 775. The dimensions of the gap are chosen such that the rim and thus also the cylinder 2 is positively locked in regard to the plunger driving part 4 with minimum play, but can be rotated around axis 20 with minimum friction. The distal surface 792 of the cylinder rim also acts as the cylinder coupling part 79.

On the surface of disk 77 facing the cylinder, three friction elements 770 are arranged, comprising a pivoting arm 771 that is connected to the driving rod coupling part 77 by a hinge 772, and that has a tip 775 facing the cylinder. The length of the friction element 770 is chosen such that in the assembled state, during normal operation of the dosing unit, the arm 771 is tilted to one side away from the direction of rotation, as shown in FIG. 24(d). The disk 77 rotates together with the driving rod 41, symbolized by the arrow to the left. The cylinder 79 is mechanically blocked in the valve seat, symbolized by the crossed-out arrow to the left. During rotation of the driving rod, the tip 775 of the friction element 770 is dragged along and slides on the distal surface 792 of the cylinder coupling part 79 with minimum friction.

In order to turn the cylinder valve member 2 in the valve seat and to switch the valve, the rotation direction of the driving rod 41 is reversed. In this direction the cylinder 2 is not mechanically blocked in the valve seat. The friction element is now tilted toward the direction of rotation (arrow to the right). Upon rotation of the driving rod 41, the tip 775 of the friction element is pressed into the surface 792 of the cylinder coupling part 79, jamming the frictional element 770 (high static friction, gripping the cylinder and pushing it in the same rotation direction (FIG. 24(e)).

When the cylinder has rotated in the static valve seat for a certain rotation angle to the second stopper that corresponds to the other valve state, further rotation of the cylinder is mechanically blocked. Forced by the continuingly rotating driving rod 41 and disk 77, the hinge region 772 of the friction element 77 is compressed (FIG. 24(f)), allowing the pivoting arm to flip to the other side (FIG. 24(g)). The friction element 770 is now again dragged along by the driving rod coupling part, with minimum sliding friction.

Also in this embodiment of a dosing unit, the friction elements can be arranged on the cylinder coupling part 79 instead on the driving rod coupling part 77, or on both parts. To increase friction, the interacting elements 770, 792 may be modified. For example can the surface 792 be provided with teeth that allow a stronger grip of the tip 773 of the friction element 770, or the surface 792 can be provided with an adhesive or compressible coating. The use of teeth makes the coupling parts unsusceptible to contamination of the surfaces by oil or similar substances. At the same time the teeth define discrete steps of the rotation angle.

In at least one embodiment shown in FIGS. 23 and 24, the driving rod, and not the plunger, actuates the cylinder valve member in the valve seat. To avoid that the plunger already gets linearly displaced during the valve switching process, the coupling between plunger shaft and driving rod is advantageously temporarily released during valve switching. This is achieved by realizing the longitudinal bore 322 and the driving rod 41 with a certain predefined play. In such an embodiment there is a reduction of friction between driving rod and plunger shaft during linear displacement.

Figure 25:
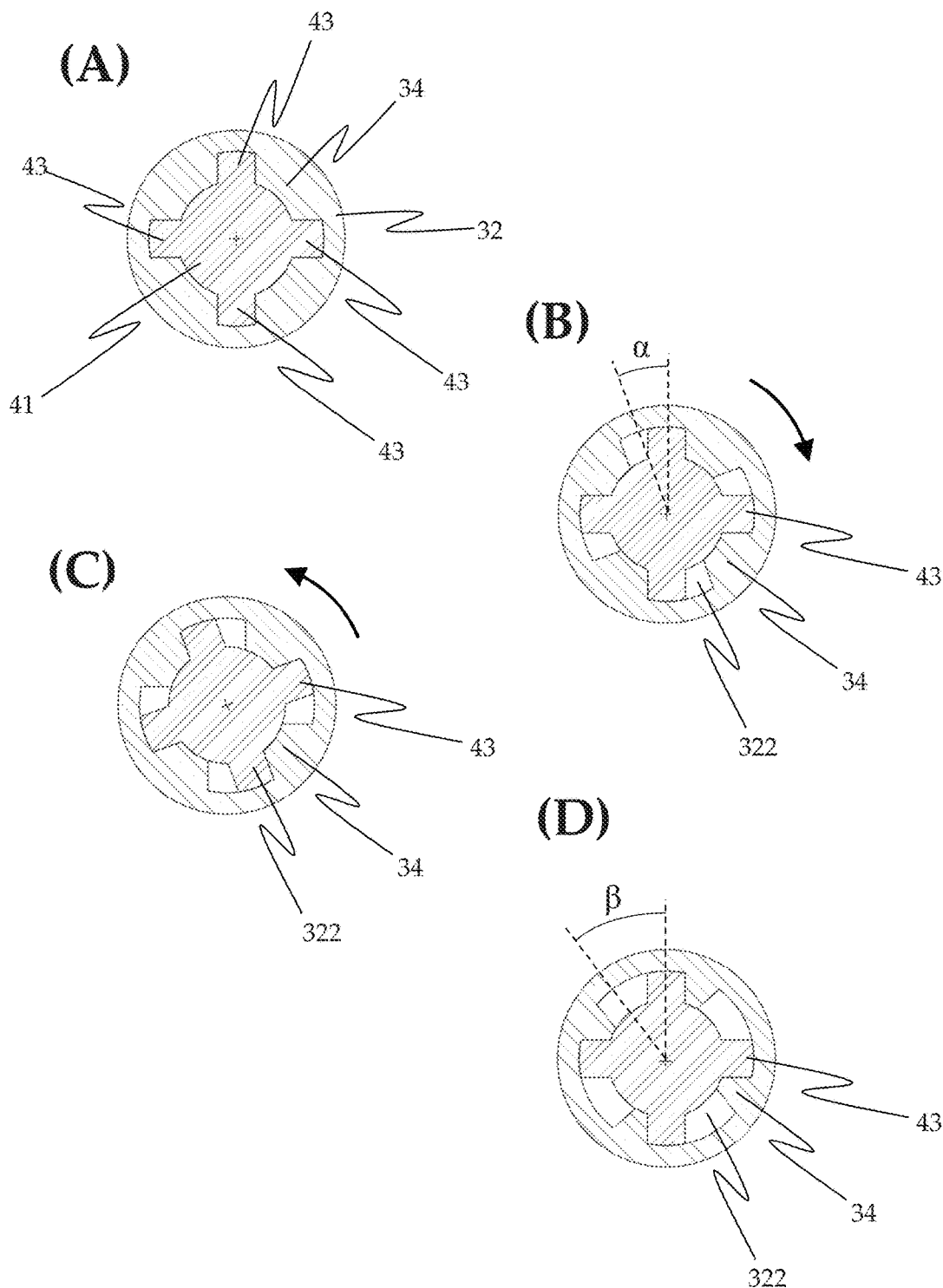
FIG. 25 schematically shows cross-sections of at least one embodiment of plunger shafts and driving rods, (A) without and (B) to (D) with rotational play.

FIG. 25 depicts in a cross-sectional view different variants of interacting plunger shafts 32 and driving rods 41. In FIG. 25(a), the longitudinal bore of the plunger shaft 32 has essentially the shape of the driving rod 41, the four longitudinal cams 43 of the driving rod being slidably arranged in corresponding slots of the longitudinal bore. Such an embodiment provides essentially no rotational play between driving rod and plunger shaft, and is advantageously used for dosing units as for example shown in FIGS. 14 to 22.

In FIG. 25(b), the longitudinal bore of the plunger shaft 32 provides rotational play. The slots between the cams 34 of the plunger shaft are designed such that upon reversal of the rotation direction of the driving rod, in the given Figure from clockwise to counter-clockwise, for a certain predefined rotation play angle α, the cams 43 do not rotationally engage with the cams 34 of the plunger rod, until the cams 43 have reached the cams 34 on the other side of the slot (FIG. 25(c)). The angle α is chosen such that the friction elements 770 of FIG. 23 or 24 can completely switch before the driving rod 41 and the plunger shaft 32 rotationally engage again. This ensures that in a dosing unit as for example shown in FIGS. 23 and 24, the friction element does not remain for a longer time in an intermediate state (FIGS. 23(d), 24(f)), which could lead to irreversible deformation.

In at least one embodiment, as shown in FIG. 25(d), the predefined rotation angle .beta. is chosen larger than the angle that is necessary for switching the valve. This ensures that it is geometrically impossible to resume plunger displacement before the valve has been switched.

At least one embodiment of dosing unit 1 is disclosed in FIG. 26. The cylinder 2 and the plunger (not visible) are identical to the embodiment shown in FIG. 5. Visible is the threaded sleeve part 26 of the cylinder 2, with the radial bias force element 5 mounted to the threaded sleeve part. A plunger driving part 4 similar to the one shown in FIG. 5 is attached to the distal end of the threaded sleeve part 26 with three mounting arms 776. The driving rod coupling part 77, to which the driving rod (not visible) and the friction elements 77 are mounted, provides additional functionality.

The friction elements 770/pivoting arms 771 are attached to the driving rod coupling part 77 by hinge structures 772, which are mounted to spring element structures 777. Said spring element structures 777 provide certain elasticity and flexibility n the longitudinal and radial direction.

The distal end of the coupling part 77, opposite to the driving rod and facing toward the driving unit (not shown), is realized as a concave, self-centering drive unit coupling 42, with three protruding cams 421 that are intended to engage with corresponding elements of the drive unit.

Figure 27:
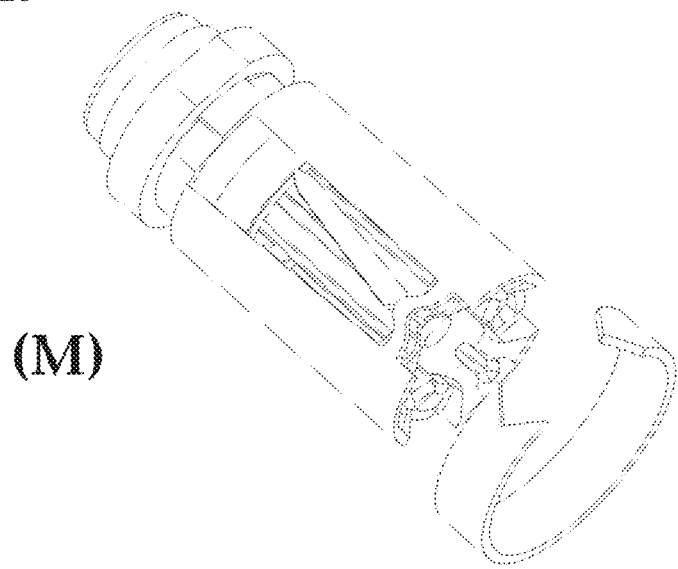
FIG. 27 shows the different steps (A-M) during valve switching with the dosing unit of FIG. 26.

In FIG. 26 the friction elements 770 are shown in the intermediate state, as shown in FIG. 24(*f*). FIG. 27 shows the different steps during valve switching. Only the most distal end of the cylinder 2 is shown. The depicted different steps are as follows:

I: The valve is in a first valve state. The driving rod coupling part 77 with the piston rod (not visible) is in the counter-clockwise freewheel mode, and the friction elements 770 are dragged along the surface 792 of the rim 222. The plunger (not shown) is linearly displaced, driven by the rotating driving rod.

II: The plunger (not visible) has reached a stop position (completely empty or completely full), or the control system of the dosing unit decides to switch the valve for another reason.

III: The valve switching process begins. The rotation direction is reversed from counter-clockwise to clockwise. The friction elements jam with the surface of the rim of the cylinder, and actuate the cylinder clockwise in the valve seat.

IV: The cylinder valve member, rotating in the valve seat (not shown) reaches the stopper (not shown) that defines the second valve position. The valve has been switched to its second state.

V: The cylinder valve member is blocked from further rotation.

VI: Upon further rotation of the driving rod, the friction elements flips over, and the jamming between driving rod and cylinder valve member is released.

VII: The valve is in the second valve state. The driving rod coupling part with the piston rod (not visible) is in the clockwise freewheel mode. The friction elements are dragged along the surface of the rim. The plunger (not shown) is linearly displaced upon rotation of the driving rod.

VIII: The plunger (not visible) has reached the other stop position (completely full or completely empty), or the control system of the dosing unit decides to switch the valve for another reason.

IX: The valve switching process begins. The rotation direction is reversed from clockwise to counter-clockwise. The friction elements jam with the surface of the rim of the cylinder, and actuate the cylinder clockwise in the valve seat.

X: The cylinder valve member, rotating in the valve seat (not shown) reaches the stopper (not shown) that defines the first valve position. The valve has been switched to its first state.

XI: The cylinder valve member is blocked from further rotation.

XII: Upon further rotation of the driving rod, the friction elements flips over, and the jamming between driving rod and cylinder valve member is released.

XIII: The valve is in the first valve state again. The driving rod coupling part with the piston rod (not visible) is in the counter-clockwise freewheel mode. The friction elements are dragged along the surface of the rim. The plunger (not shown) is linearly displaced upon rotation of the driving rod. Step XIII is essentially identical to step I, except for the angular orientation of the driving rod.

Figure 28:
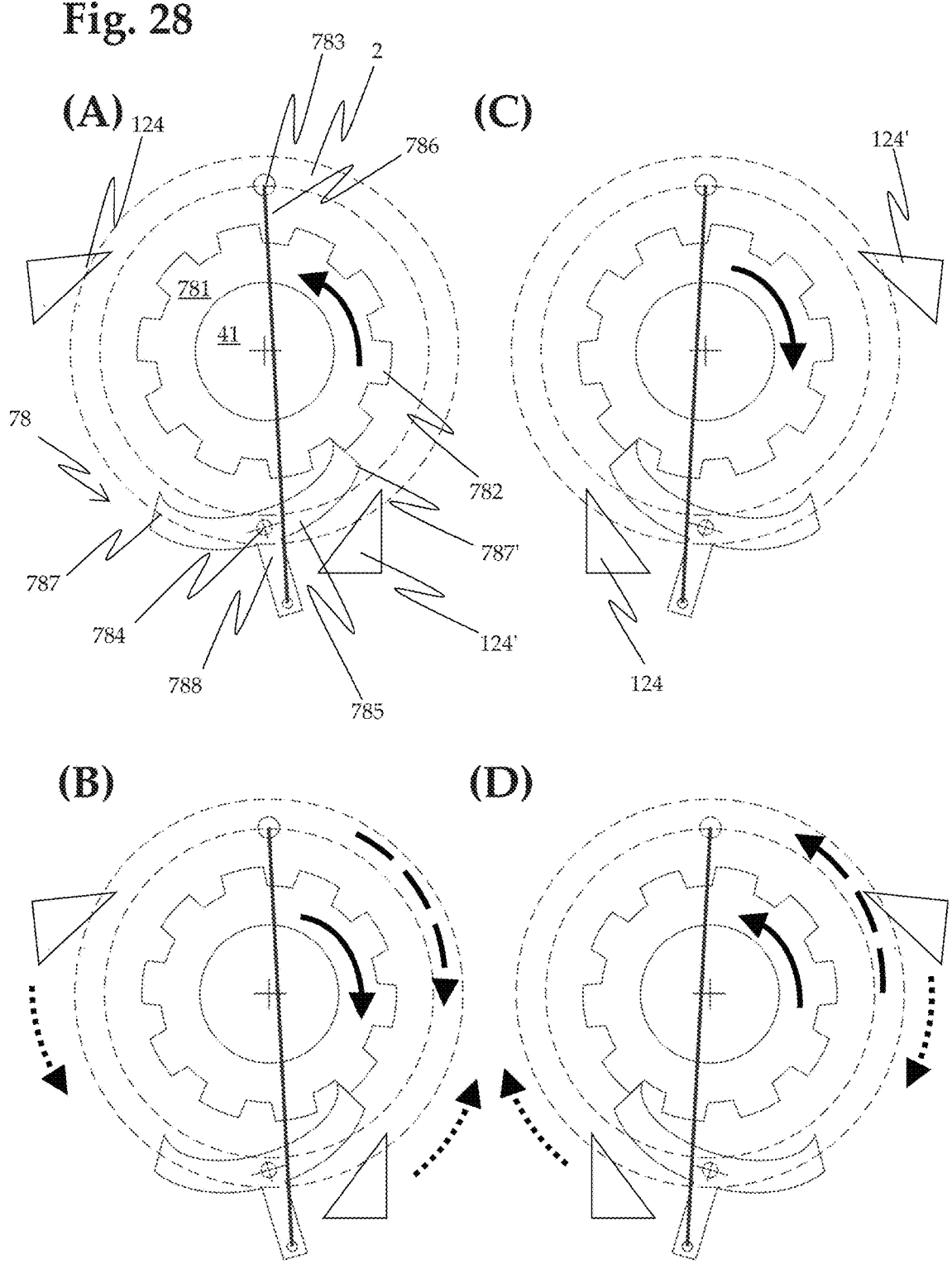
FIG. 28 schematically shows subsequent steps (A-D) of at least one approach to realize a controlled coupling between cylinder and driving rod, based on a bistable ratchet mechanism.

In at least one dosing unit is schematically depicted in FIG. 28, where a controlled coupling between cylinder 2 and driving rod 41 is realized with a bistable ratchet mechanism 78. All figures are shown with the cylinder valve member remaining static, and the driving rod 41 and valve seat moving in relation to the cylinder valve member.

A cog wheel 781 is mounted on the driving rod 41 at a distal end. A double pawl element 785 with two opposite pawls 787, 787' is pivotably mounted on an axis bearing 784, which itself is mounted on the cylinder valve member 2. The double pawl element 785 is provided with an arm 788. A tension spring 786 is arranged between a first suspension point at the end of the arm and a second suspension point 783. To provide symmetrical operational conditions, said second suspension point 783 has to be located somewhere on a straight line through the driving rod's rotation axis and the pivotal axis 784 of the double pawl element 785.

In FIG. 28(*a*) the driving rod 41 is in the counter-clockwise freewheel mode (symbolized by an arrow). The plunger can be linearly displaced in the corresponding direction. The bistable ratchet mechanism is in one of its stable states, driven by the spring force of the tension spring 786. The teeth 782 of the cog wheel 781, rotating counter-clockwise together with the driving rod, can pass the pawl 787' without switching the ratchet mechanism.

For switching the valve, the rotation direction of the driving rod 41 is reversed, in the given case from counter-clockwise to clockwise (FIG. 28(*b*). The tooth right of the pawl 787' abuts the pawl, and the ratchet is jammed. The driving rod 41 and the cylinder valve member 2 are now rotationally coupled via the pawl 787 and the bearing axis 784, and the rotating driving rod rotates the cylinder valve member clockwise (dashed arrow).

The rotation of the cylinder is stopped when a first switching element 124 mounted to the valve seat (dotted arrow) reaches the bistable ratchet mechanism, as shown FIG. 28(*c*). The switching element 124 pushes the first pawl 787 toward the cogwheel. The double pawl element 785 pivots around the axis bearing 784, the tension spring 786 is expanded, and when the arm 788 passes the line defined by suspension point 783 and axis bearing 784, the bistable ratchet switches to the other state. The cylinder valve member 2 is now rotationally decoupled from the driving rod 41. The driving rod 41 is in the clockwise freewheel mode again. The teeth of the cogwheel can pass the ratchet mechanism without engaging, and the plunger is linearly displaced in the opposite direction.

To switch the valve back to the first state, the process is repeated (FIG. 28(*d*)), by reversing the rotation direction from clockwise to counter-clockwise. The ratchet and the cogwheel jam, rotationally coupling the cylinder valve member and the driving rod. The driving rod rotates the cylinder valve member counter-clockwise, until the second switching element 124' mounted to the valve seat reaches the ratchet mechanism, and flips over the double pawl element to its first state, as shown in FIG. 28(a), thereby decoupling again the cylinder valve member and the driving rod.

The angular position of the switching elements 124, 124' is chosen such that the ratchet switching positions correspond to the two valve positions. Thus no additional stopper elements are necessary, delimiting the rotation of the cylinder valve member in the valve seat. Advantageously they are nevertheless provided, to define clear valve end positions.

Instead of using a separate cogwheel the driving rod itself may be used as the cogwheel, with its cams 43 acting as the teeth, if a sufficient number of cams 43 are provided to realize the ratchet mechanism.

At least one embodiment of a controllable coupling between driving rod 41 and cylinder valve member 2 is disclosed in FIG. 29. A driving rod 41 is arranged within the cylinder 2, operationally engaging with the plunger shaft (not visible). Only the distal end 412 of the driving rod is visible in FIG. 29(a). The driving rod is provided with a driving rod coupling part 77, in the form of a hollow cylinder 778. The distal end of the cylinder is provided with a cylinder coupling part 79, intended to be arranged in the hollow cylinder 778. The cylinder coupling part 79 comprises two clamp arms 793, 793' that are pivotably connected to the cylinder 2 via hinges 794, 794'. One clamp arm 793 has one clamp finger 795, having a radial protrusion on the outside toward the inner side of the hollow cylinder 778. The other clamp arm 794' has two clamp fingers 795' with a radial protrusion. Alternatively both clamp arms may be provided with an equal number of clamp fingers.

The dimensions of the two coupling parts 79, 77 are chosen such that in the assembled state of the dosing unit the clamp fingers 795, 795' are radially biased against the inner surface of the hollow cylinder 778. As a result the driving rod 41 and the cylinder valve member 2 are frictionally coupled, the rotating driving rod being able to actuate the cylinder valve member.

To minimize friction during the linear displacement of the plunger within the cylinder, the cylinder coupling part 79 is provided with means 796, 796' to rotationally decouple the two coupling parts 79, 77. Each of the two clamp arms is provided with a release element arranged 796, 796' outside of the hollow cylinder 778. Two switching elements (not visible) mounted on the valve seat are arranged on such angular positions that in each of the two valve states, one of the switching elements engages with one of the decoupling elements 796, 796'. The resulting force presses the corresponding clamp arm 793, 793' inwards, thereby decoupling the two coupling parts 79, 77, and thus the driving rod 41 and the cylinder valve member 2. Upon further rotation of the driving rod in the same direction, friction is minimal, and the cylinder valve member remains on place.

To switch the valve, the rotation direction of the driving rod is reversed. The switching element disengages the release element, and the clamp arms engage again with the hollow cylinder. The frictionally coupled cylinder valve member rotates together with the driving rod, until the second switching element reaches the second release element, and coupling element and driving rod are decoupled again.

Instead of coupling arms engaging with a hollow cylinder, another embodiment of such a controllable coupling can be realised with a coiled spring, connected to the cylinder. The coil spring is looped around a cylindrical portion of the driving rod, and frictionally couples the cylinder and the driving rod. Switching elements of the valve seat can engage with the ends of the coil spring, increasing the radius of the coil spring and temporarily decoupling cylinder and driving rod.

While various embodiments of dosing units and methods for their use have been described in considerable detail herein, the embodiments are merely offered by way of non-limiting examples of the disclosure described herein. It will therefore be understood that various changes and modifications may be made, and equivalents may be substituted for elements thereof, without departing from the scope of the disclosure. Indeed, this disclosure is not intended to be exhaustive or to limit the scope of the disclosure.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. Other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

LIST OF REFERENCE NUMERALS

1 dosing unit
11 metering cavity
12 valve seat
21 inlet
22 outlet
123, 123' stopper elements
124, 124' switching element
2 pump cylinder/cylinder valve member
20 cylinder axis
21 cylinder head
211 opening
212 guide ring
22 cylinder wall
221 opening in the cylinder wall
222 rim
23, 23' threaded portion of the cylinder, cylinder thread
25, 25', 25", 25''' threaded claw
251 slot
26 threaded sleeve part
261 slot
262 protrusion
263 sleeve element
27 tension ring
271 slot
28 cavity part
29 cam
3 plunger
31 plunger plug
311 plug sealing element
312 plug protrusion 32 plunger shaft
321, 321' shaft arm, split portion of plunger shaft
323 hinge
322 longitudinal bore
33, 33' threaded portion of the plunger, plunger thread
33a, 33a', 33a" portions of the thread
331 lateral surface of the thread
34 cam
35 plunger coupling element
37 slot
38 slot
39 bridge structure
4 plunger driving part
41 plunger driving rod
411 proximal part
412 distal part
42 drive unit coupling
421 cam
43, 43' cam
44, 44' cam
441 cut-out
45 radial bias force element
451 threaded element
452 spring element
453 locking structure
455 wire
56 flat surface element
57 mounting sleeve
58 opening
59 spring element
59a inner thread segment
59b outer thread segment
6 axial bias force element
62 spring element
64, 64' threaded element
65 inner thread portion of threaded element
66 outer thread portion of threaded element
7 friction control element
71, 71' ramp
71a elevation
72, 72' ramp
73, 73' stopper disk
73a, 73a' stopper disk
74, 74' friction cylinder
74a, 74a' friction cylinder
75 cylinder coupling part
751 locking hole
76 plunger coupling part
761, 761' spring-biased ball, locking element
762 cam, locking element
763 pivot arm
77 driving rod coupling part
770 friction element
771 pivoting arm
772 hinge
773 tip
774 snap lock cam
775 distance rip
776 mounting arm
777 spring element
778 hollow cylinder
78 bistable ratchet mechanism
781 cog wheel
782 tooth
783 suspension point
784 axis bearing
785 double pawl element
787, 787' pawl
786 tension spring
788 arm
79 cylinder coupling part
792 surface
793, 793' clamp arm
794, 794' hinge
795, 795' clamp finger
796, 796' release element
$F_{bias}$ bias force
$F_{bias,ax}$ axial component of the bias force
$F_{ax}$ axial force acting on the plunger

The invention claimed is:

1. A dosing unit for an infusion pump device, the dosing unit comprising a piston pump with a pump cylinder, a plunger arranged within the pump cylinder, and a plunger driving part provided for transmitting rotational torque to the plunger without itself being linearly displaced, the cylinder, the plunger and the plunger driving part being coaxially arranged along a longitudinal axis and rotatable around said axis in regard to static parts of the dosing unit;
   wherein the plunger has a plunger shaft with a plunger thread and the cylinder has a threaded sleeve part with a cylinder thread;
   wherein one of plunger thread or cylinder thread is an outer thread and the other one is an inner thread, the inner thread and outer thread engaging with each other in such a way that a rotational movement of the plunger around the longitudinal axis results in an additional linear displacement of the plunger along said longitudinal axis;
   wherein the plunger driving part has a driving rod that is arranged in a longitudinal bore of the plunger shaft, the driving rod being linearly displaceable within the longitudinal bore along the longitudinal axis, and being rotationally engaged with the plunger shaft;
   the dosing unit further comprising one or more first coupling parts mounted to or being integral with the cylinder, and one or more second coupling parts mounted to or being integral with the plunger driving part and/or the plunger; wherein the first and second coupling parts interact in such a way that
   a. the first and second coupling parts are bidirectionally switchable between a first state and a second state, by reversing the rotation direction of the plunger driving part;
   b. the first and second coupling parts are unidirectionally switchable from the first state to the second state, by mechanically blocking cylinder rotation or actuating the first coupling part; and
   c. the cylinder is rotationally coupled to the plunger driving part in the first state of the first and second coupling parts; and not rotationally coupled in the second state;
   the first and second coupling parts interacting in such a way that the cylinder is rotationally coupled to the plunger on at least one linear position of the plunger in regard to the cylinder and is not rotationally coupled to the plunger on the other positions; and
   wherein the one or more first coupling part is mounted to or is integral with the cylinder, and the one or more second coupling part is mounted to or is integral with the plunger driving part; wherein the first and/or the second coupling part comprise one or more bistable elements that are configured to be in a first configuration where the one or more bistable elements rotationally couple the first and second coupling parts by static friction or positive locking when the plunger driving part rotates clockwise, and do not rotationally couple the first and second coupling parts when the plunger driving part rotates counter-clockwise; and in a second configuration where the bistable elements rotationally couple the first and second coupling parts by static friction or positive locking when the plunger driving part rotates counter-clockwise, and do not rotationally couple the first and second coupling parts when the plunger driving part rotates clockwise.

2. The dosing unit of claim 1, wherein the one or more bistable elements are friction elements that are switchable between two configurations, and that the rotational coupling is a static frictional coupling.

3. The dosing unit of claim 2, wherein the one or more bistable friction elements are switchable between the two configurations by reversing the rotation direction of the plunger driving part in case the first and second coupling parts are not rotationally coupled; and by reversing the rotation direction of the plunger driving part and blocking cylinder rotation in case the first and second coupling parts are rotationally coupled.

4. The dosing unit of claim 3, wherein that cylinder rotation is blocked on at least one angular orientation of the cylinder in regard to the static parts of the dosing unit.

5. The dosing unit of claim 1, wherein the one or more bistable elements are ratchet mechanisms that are switchable between two configurations, and that the rotational coupling is active when the ratchet mechanism is locked.

6. The dosing unit of claim 5, wherein the ratchet mechanism are switchable between the two states by reversing the rotation direction of the plunger driving part where the ratchet mechanism is locked; and by reversing the rotation direction of the plunger driving part and additionally actuating the ratchet mechanism where the ratchet mechanism is not locked.

7. The dosing unit of claim 6, wherein the ratchet mechanism is actuated by switching elements mounted to or being integral with the static parts of the dosing unit.

8. The dosing unit of claim 1, wherein the one or more first coupling parts comprise first ramps provided on the plunger driving rod, and the one or more second coupling parts comprise second ramps provided on a structure pivotably mounted on the plunger shaft, the structure carrying portions of the outer thread; wherein the first and second ramps are arranged such that on at least one linear positions of the plunger, in regard to the cylinder, some of the first ramps abut some of the second ramps, and press the outer thread portions radially outwards onto the inner thread of the cylinder, thereby frictionally coupling the cylinder and the plunger.

9. The dosing unit of claim 1, wherein the one or more first coupling parts are first friction elements mounted to or being integral with the cylinder, and the one or more second coupling parts are second friction elements mounted to or being integral with the plunger, wherein in at least one longitudinal position of the plunger in regard to the cylinder one of the first friction elements frictionally engages with one of the second friction elements, thereby frictionally coupling the cylinder and the plunger.

10. The dosing unit of claim 9, wherein the one or more first friction element is a hollow cylinder, and the one or more second friction element is a friction cylinder, wherein the friction cylinder frictionally engages with the hollow cylinder when the friction cylinder is located in the hollow cylinder.

11. The dosing unit of claim 1, wherein the one or more first coupling parts are first stopper elements mounted to or being integral with the cylinder, and the one or more second coupling parts are second stopper elements mounted to or being integral with the plunger, wherein at certain longitudinal positions of the plunger in regard to the cylinder one of the first stopper elements abuts with one of the second stopper elements, thereby blocking the further linear displacement of the plunger, and releasably jamming the inner thread of the cylinder and the outer thread of the plunger.

12. The dosing unit of claim 11, wherein the stopper elements are disks.

13. The dosing unit of claim 1, wherein the first coupling part is a cylinder coupling part and the second coupling part is a plunger coupling part, wherein the cylinder coupling part comprises a first locking element and the plunger coupling part comprises a second locking element, which releasably lock the plunger to the cylinder with at least one longitudinal positions of the plunger in regard to the cylinder.

14. The dosing unit of claim 1, wherein the first coupling part and the second coupling part are frictionally coupled, and wherein the frictional coupling is releasable by switching elements mounted to or being integral with the static parts of the dosing unit.

15. The dosing unit of claim 1, further comprising a separate bias force element that biases the inner thread and the outer thread in regard to each other along the longitudinal axis, such that the threaded engagement of inner thread and outer thread is free of play independent of a direction of a rotational movement and linear displacement of the plunger in regard to the cylinder.

16. The dosing unit of claim 15, wherein the plunger thread is the outer thread and the cylinder thread is the inner thread.

17. The dosing unit of claim 15, wherein the bias force element subjects the plunger shaft to a force perpendicular to the longitudinal axis, thereby pressing a portion of the plunger thread onto a portion of the cylinder thread.

18. The dosing unit of claim 17, wherein the bias force element comprises a radially biased flat surface that abuts the lateral surface of an outer one of the two threads.

19. The dosing unit of claim 15, wherein one or more portions of the cylinder thread or the plunger thread are pivotably mounted on the cylinder, or on the plunger shaft, respectively.

20. The dosing unit of claim 19, further comprising a spring element, the spring element radially biases the pivotably mounted thread portions toward the other thread.

21. The dosing unit of claim 15, wherein the bias force element comprises a tensioned segment of wire that is mounted to the cylinder or the plunger and is arranged in such a way that it is located in a groove segment of the outer thread and exercises a bias force perpendicular to the longitudinal axis.

22. The dosing unit of claim 15, wherein the bias force element comprises a threaded element, which is coaxially mounted on the first threaded sleeve or on the plunger shaft, and is longitudinally shiftable in regard to the first threaded sleeve or the plunger shaft, respectively; which has an thread portion engaging with the plunger thread or the cylinder thread, respectively; and which has a spring element that subjects the threaded element to an axial bias force in regard to the first threaded sleeve or the plunger shaft, respectively.

23. The dosing unit of claim 15, wherein the bias force element comprises one or more spring elements with inner or outer thread segments, such that said inner or outer thread segments are radially biased toward the outer or inner thread, and wherein the inner or outer thread segments act as the inner or outer thread, respectively.

24. The dosing unit of claim 15, wherein the bias force element is elastic.

25. The dosing unit of claim 15, wherein the bias force element is made from a material that is different from the material of the cylinder and/or the plunger.

26. The dosing unit of claim 15, characterized in that the bias force element is made from metal, and/or the cylinder and/or the plunger is made from polymer.

\* \* \* \* \*